US008288417B2

(12) United States Patent
Yao et al.

(10) Patent No.: US 8,288,417 B2
(45) Date of Patent: Oct. 16, 2012

(54) N-SUBSTITUTED PIPERIDINES AND THEIR USE AS PHARMACEUTICALS

(75) Inventors: Wenqing Yao, Kennett Square, PA (US); Meizhong Xu, Hockessin, DE (US); Colin Zhang, Ambler, PA (US); Yanlong Li, Newark, DE (US); Jincong Zhuo, Garnet Valley, PA (US); Brian W. Metcalf, Moraga, CA (US)

(73) Assignee: Incyte Corporation, Wilmington, DE (US)

( * ) Notice: Subject to any disclaimer, the term of this patent is extended or adjusted under 35 U.S.C. 154(b) by 0 days.

(21) Appl. No.: 13/279,700

(22) Filed: Oct. 24, 2011

(65) Prior Publication Data

US 2012/0040964 A1    Feb. 16, 2012

Related U.S. Application Data

(62) Division of application No. 11/159,448, filed on Jun. 23, 2005, now Pat. No. 8,071,624.

(60) Provisional application No. 60/582,557, filed on Jun. 24, 2004, provisional application No. 60/614,570, filed on Sep. 30, 2004, provisional application No. 60/686,840, filed on Jun. 2, 2005.

(51) Int. Cl.
*A61K 31/4523* (2006.01)
*C07D 211/00* (2006.01)

(52) U.S. Cl. ........................................ 514/330; 546/189
(58) Field of Classification Search .................. 514/330; 546/189
See application file for complete search history.

(56) References Cited

U.S. PATENT DOCUMENTS

| | | |
|---|---|---|
| 3,097,209 A | 7/1963 | Janssen et al. |
| 3,328,156 A | 6/1967 | Hopkins |
| 3,770,748 A | 11/1973 | Borck et al. |
| 3,849,403 A | 11/1974 | Yardley et al. |
| 3,923,350 A | 12/1975 | Berry et al. |
| 3,933,829 A | 1/1976 | Archibald et al. |
| 4,001,422 A | 1/1977 | Danilewicz et al. |
| 4,013,445 A | 3/1977 | Bellus et al. |
| 4,076,819 A | 2/1978 | Maffrand |
| 4,145,435 A | 3/1979 | Szmuszkovicz |
| 4,439,606 A | 3/1984 | Du et al. |
| 4,701,459 A | 10/1987 | Meanwell et al. |
| 5,244,894 A | 9/1993 | George et al. |
| 5,292,745 A | 3/1994 | Haulme |
| 5,442,064 A | 8/1995 | Pieper et al. |
| 5,567,060 A | 10/1996 | Steinberger et al. |
| 5,614,534 A | 3/1997 | Binet et al. |
| 5,633,247 A | 5/1997 | Baldwin et al. |
| 5,668,138 A | 9/1997 | Baziard-Mouysset et al. |
| 5,693,567 A | 12/1997 | Weisfield et al. |
| 5,817,678 A | 10/1998 | Kim et al. |
| 5,852,029 A | 12/1998 | Fisher et al. |
| 5,981,754 A | 11/1999 | Badone et al. |
| 6,087,379 A | 7/2000 | Asai et al. |
| 6,242,438 B1 | 6/2001 | MacKenzie et al. |
| 6,288,085 B1 | 9/2001 | Rae et al. |
| 6,547,958 B1 | 4/2003 | Elomari et al. |
| 6,610,708 B1 | 8/2003 | Asai et al. |
| 6,683,096 B2 | 1/2004 | Pages Santacana et al. |
| 7,074,788 B2 | 7/2006 | Kurz et al. |
| 7,119,091 B2 | 10/2006 | Habashita et al. |
| 7,122,532 B2 | 10/2006 | Walker et al. |
| 7,304,081 B2 | 12/2007 | Yao et al. |
| 8,071,624 B2 | 12/2011 | Yao et al. |
| 2003/0203922 A1 | 10/2003 | Patel et al. |
| 2003/0229119 A1 | 12/2003 | Kym et al. |
| 2003/0236286 A1 | 12/2003 | Deorazio et al. |
| 2004/0072802 A1 | 4/2004 | Duan et al. |
| 2004/0188324 A1 | 9/2004 | Elomari |
| 2005/0020645 A1 | 1/2005 | Ohta et al. |
| 2005/0080078 A1 | 4/2005 | Aquila et al. |
| 2005/0282858 A1 | 12/2005 | Yao et al. |
| 2005/0288317 A1 | 12/2005 | Yao et al. |
| 2005/0288329 A1 | 12/2005 | Yao et al. |
| 2005/0288338 A1 | 12/2005 | Yao et al. |
| 2006/0004049 A1 | 1/2006 | Yao et al. |
| 2006/0009471 A1 | 1/2006 | Yao et al. |
| 2006/0009491 A1 | 1/2006 | Yao et al. |
| 2006/0019977 A1 | 1/2006 | Habashita et al. |
| 2006/0106045 A1 | 5/2006 | Hughes et al. |
| 2006/0116382 A1 | 6/2006 | Yao et al. |
| 2006/0122197 A1 | 6/2006 | Yao et al. |
| 2006/0122210 A1 | 6/2006 | Yao et al. |
| 2006/0149070 A1 | 7/2006 | Rohde et al. |
| 2006/0199816 A1 | 9/2006 | Gillespie et al. |
| 2007/0066584 A1 | 3/2007 | Yao et al. |
| 2007/0129345 A1 | 6/2007 | Zhuo et al. |
| 2007/0179142 A1 | 8/2007 | Yao et al. |
| 2007/0197506 A1 | 8/2007 | Yao et al. |
| 2007/0197530 A1 | 8/2007 | Li et al. |

(Continued)

FOREIGN PATENT DOCUMENTS

CH    676846    3/1991

(Continued)

OTHER PUBLICATIONS

Alberts et al. Endocrinology (2003) 144: 4755-4762.

(Continued)

*Primary Examiner* — Taofiq A Solola
(74) *Attorney, Agent, or Firm* — Fish & Richardson P.C.

(57) ABSTRACT

The present invention relates to inhibitors of 11-β hydroxyl steroid dehydrogenase type 1, antagonists of the mineralocorticoid receptor (MR), and pharmaceutical compositions thereof. The compounds of the invention can be useful in the treatment of various diseases associated with expression or activity of 11-β hydroxyl steroid dehydrogenase type 1 and/or diseases associated with aldosterone excess.

21 Claims, No Drawings

U.S. PATENT DOCUMENTS

| | | | |
|---|---|---|---|
| 2007/0208001 A1 | 9/2007 | Zhuo et al. |
| 2007/0213311 A1 | 9/2007 | Li et al. |
| 2007/0270424 A1 | 11/2007 | Li et al. |
| 2007/0275990 A1 | 11/2007 | Ohmoto et al. |
| 2007/0293529 A1 | 12/2007 | Li et al. |
| 2008/0255154 A1 | 10/2008 | Yao et al. |
| 2008/0318991 A1 | 12/2008 | Yao et al. |

FOREIGN PATENT DOCUMENTS

| | | |
|---|---|---|
| DE | 2623567 | 12/1976 |
| DE | 39 11 670 | 10/1990 |
| EP | 0 141 419 | 5/1985 |
| EP | 0273659 | 7/1988 |
| EP | 0 404 039 | 12/1990 |
| EP | 0 498 718 | 8/1992 |
| EP | 0 743 312 | 11/1996 |
| EP | 0 520 883 | 7/2005 |
| EP | 1683797 | 7/2006 |
| ES | 427 013 | 7/1976 |
| FR | 1 600 908 | 8/1970 |
| FR | 2289498 | 5/1976 |
| GB | 2327609 | 2/1999 |
| GE | 2187 | 7/2000 |
| GE | 3710 | 12/2005 |
| JP | 48-6469 | 2/1973 |
| JP | 57-156450 | 9/1982 |
| JP | 60149562 | 8/1985 |
| JP | 4-275271 | 9/1992 |
| JP | 04-334357 | 11/1992 |
| RU | 97107464 | 5/1999 |
| RU | 98114667 | 5/2000 |
| RU | 2183624 | 6/2002 |
| RU | 99104152 | 9/2002 |
| RU | 2000122434 | 9/2002 |
| RU | 2002100073 | 1/2004 |
| RU | 2002117652 | 1/2004 |
| RU | 2001128769 | 5/2004 |
| WO | WO9610027 | 4/1996 |
| WO | WO9711940 | 4/1997 |
| WO | WO9741102 | 11/1997 |
| WO | WO9811098 | 3/1998 |
| WO | WO9964004 | 12/1999 |
| WO | WO0001702 | 1/2000 |
| WO | WO0023076 | 4/2000 |
| WO | WO0058305 | 10/2000 |
| WO | WO0059874 | 10/2000 |
| WO | WO0105790 | 1/2001 |
| WO | WO0130780 | 5/2001 |
| WO | WO0170673 | 9/2001 |
| WO | WO0204425 | 1/2002 |
| WO | WO0204465 | 1/2002 |
| WO | WO0206868 | 1/2002 |
| WO | WO0222572 | 3/2002 |
| WO | WO0246156 | 6/2002 |
| WO | WO02058690 | 8/2002 |
| WO | WO02069973 | 9/2002 |
| WO | WO02078641 | 10/2002 |
| WO | WO02092585 | 11/2002 |
| WO | WO03010138 | 2/2003 |
| WO | WO03022809 | 3/2003 |
| WO | WO03037271 | 5/2003 |
| WO | WO03037847 | 5/2003 |
| WO | WO03041641 | 5/2003 |
| WO | WO03045912 | 6/2003 |
| WO | WO03049736 | 6/2003 |
| WO | WO03051840 | 6/2003 |
| WO | WO03053915 | 7/2003 |
| WO | WO03057698 | 7/2003 |
| WO | WO03072197 | 9/2003 |
| WO | WO03077847 | 9/2003 |
| WO | WO03099821 | 12/2003 |
| WO | WO03104207 | 12/2003 |
| WO | WO2004000789 | 12/2003 |
| WO | WO2004005295 | 1/2004 |
| WO | WO2004017961 | 3/2004 |
| WO | WO2004018479 | 3/2004 |
| WO | WO2004022554 | 3/2004 |
| WO | WO2004033427 | 4/2004 |
| WO | WO2004033440 | 4/2004 |
| WO | WO2004056745 | 7/2004 |
| WO | WO2004058715 | 7/2004 |
| WO | WO2004058727 | 7/2004 |
| WO | WO2004065351 | 8/2004 |
| WO | WO2004076418 | 9/2004 |
| WO | WO2004082687 | 9/2004 |
| WO | WO2004089470 | 10/2004 |
| WO | WO2004089896 | 10/2004 |
| WO | WO2004096139 | 11/2004 |
| WO | WO2004098589 | 11/2004 |
| WO | WO2004103995 | 12/2004 |
| WO | WO2005032472 | 4/2005 |
| WO | WO2005037814 | 4/2005 |
| WO | 2005047286 | 5/2005 |
| WO | WO2005044797 | 5/2005 |
| WO | WO2005060963 | 7/2005 |
| WO | WO2005061499 | 7/2005 |
| WO | WO2005063745 | 7/2005 |
| WO | WO2005068460 | 7/2005 |
| WO | WO2005070407 | 8/2005 |
| WO | WO2005108359 | 11/2005 |
| WO | WO2005110992 | 11/2005 |
| WO | WO2006002349 | 1/2006 |
| WO | WO2006002350 | 1/2006 |
| WO | WO2006002361 | 1/2006 |
| WO | WO2006012173 | 2/2006 |
| WO | WO2006012226 | 2/2006 |
| WO | WO2006012227 | 2/2006 |
| WO | WO2006020598 | 2/2006 |
| WO | WO2006047176 | 5/2006 |
| WO | WO2006053024 | 5/2006 |
| WO | WO2006053120 | 5/2006 |
| WO | WO2006055752 | 5/2006 |
| WO | WO2006094633 | 9/2006 |
| WO | WO2006138512 | 12/2006 |
| WO | WO2007038138 | 4/2007 |
| WO | WO2007051810 | 5/2007 |
| WO | WO2007067504 | 6/2007 |
| WO | WO2007084314 | 7/2007 |
| WO | WO2007089683 | 8/2007 |
| WO | WO2007101270 | 9/2007 |
| WO | WO2007103719 | 9/2007 |

OTHER PUBLICATIONS

Albiston et al. (1994) Mol. Cell. Endocrin. 105: R11-R17.
Ammar et al., "Synthesis of 7,7-dimethylaporphine alkaloids", Heterocycles, (1983), 20(3), 451-4, Database CA [Online], Chemical Abstracts Service, Ohio, US; retrieved from STN Database Accession No. 1983:198499 (1983).
Atwell et al., "Relationships between structure and kinetics of cyclization of 2-aminoaryl amides: potential prodrugs of cyclization-activated aromatic mustards", Journal of Medicinal Chemistry, (1994), 37(3), 371-80, Database CA [Online], Chemical Abstracts Service, Ohio, US; retrieved from STN Database Accession No. 1994:216381 (1994).
Banker, G.S. et al., "Modern Pharmaceutics, 3ed.", Marcel Dekker, New York, 1996, pp. 451 and 596.
Barf et al. (2002) J. Med. Chem. 45: 3813-3815.
Bellows et al. (1998) Bone 23: 119-125.
Ben et al., "Synthesis of Optically Active α-Amino Esters via Dynamic Kinetic Resolution: A Mechanistic Study," J. Org. Chem. 64: 7700-7706 (1999).
Bhargava et al., (2001), Endo 142: 1587-1594.
Billaudel and Sutter (1979) Horm. Metab. Res. 11: 555-560.
Binet et al., "Structure activity relationships of new inhibitors of mammalian 2,3-oxidosqualene cyclase", Chemical and Pharmaceutical Bulletin, vol. 50, No. 3, 2002, pp. 316-329.
Blum, et al., (2003) Prog. Nucl. Acid Res. Mol. Biol. 75:173-216.
Bolm, C. et al., J. Org. Chem., 2005, 70, 2346.
Borthwick, A.D. et al., J. Med. Chem., 2003, 46, 4428.
Bujalska et al. (1997) Lancet 349: 1210-1213.
Burke et al., Org. Lett., 2004, 6(3), 405-407.
Bursavich et al., Org. Lett., 2001, 3, 2625.

Buzas, A. et al., *Chimica Therapeutica, Eur. J. Med. Chem.*, 1972, 7(5), pp. 361-426.
Bydal et. al. "Inhibition of type 2 17b-hydroxysteroid dehydrogenase by estradiol derivatives bearing a lactone on the D-ring: structure-activity relationships" Steroids 2004, 69, 325-342.
Canalis (1996) J. Clin. Endocrinol. Metab. 81: 3441-3447.
Chem. Abs. 79:31890 abstracting Japanese Patent No. JP 48-6469 dated Feb. 26, 1973.
Chem. Abs. 82:156099 abstracting Japanese Patent No. JP 49039678 dated Oct. 28, 1974.
Chem. Abs. 118:254748 abstracting Japanese Patent No. JP-4-275271 dated Sep. 30, 1992.
Chem. Abs. 129:148842 abstracting Miyabe et al.,*J. Org. Chem.*, 1998, 63(13), 4397-407.
Cheng et al., *Eur. J. Med. Chem.*, 1991, 26(2), pp. 125-128.
Combs, et al., *J. Comb. Chem.* 2002, 4, 179.
Conn, (1955), J. Lab. Clin. Med. 45: 6-17.
Conroy, et al., "Using the electrostatic field effect to design a new class of inhibitors for cysteine proteases", *J. Am. Chem. Soc.*, 1997, vol. 119, pp. 4285-4291.
Cooper et al. (2000) Bone 27: 375-381.
Coutts et al., *J. Chem. Soc. Pekin. Trans. I*, 1990, (3), 767-771.
Coutts et al., "The conversion of phenols to primary and secondary aromatic amines via a Smiles rearrangement", J. Chem. Soc., Perkin Trans. 1, 1990, 767-771; Chem. Abs. AN 1990:514704 (1990).
Cuiban., "Reductive cyclization .alpha.- and .beta.-(o-nitrophenyl)-substituted amides", Revue Roumaine de Chimie, (1972), 17(5), 897-903, abstracted in Database CA [Online], Chemical Abstracts Service, Columbus, Ohio, US, Database Accession No. 1972:539925 (1972).
Dankwardt, et al., *Tetrahedron Lett.* 1995, 36, 4923.
Database CAPLUS on STN (Columbus, OH, USA) No. 126:317635, "Alpha-amino acids derived from ornithine as building blocks for peptide synthesis" abstract, Gescrinier et al. *J. Pep. Res.* 49(2):183-189 (1997).
Database CAPLUS on STN (Columbus, OH, USA) No. 143:78479, "Preparation of amino acid derivatives as novel M3 muscarinic acetylcholine receptor antagonists" abstract, Busch et al. (2005), see RN 902149-23-9 and 854750-92-8.
Database CAPLUS on STN (Columbus, OH, USA) No. 143:7612, "Preparation of Heterocyclic Spiro Compounds for Treatment of Stress Related Diseases", RN 64097-78-5, (2005).
Database CAPLUS on STN (Columbus, OH, USA) No. 135:257227, "Preparation of pyrrolidinone derivatives having .sigma.-receptor affinity", RN-362518-14-7, RN 362518-16-9, RN 362518-15-8, RN 363518-17-0; (2001).
Database CAPLUS on STN (Columbus, OH, USA) No. 55:87498, "Synthetic drugs. VI. A new type of spirosusccinimade", RN-64097-71-8; RN-102654-82-0; RN-113251-47-1, RN-113687-61-9, RN-114509-25-0; (1961).
Database CAPLUS ACS on STN, 2006, Caplus English Abstract US 2005288317, Dec. 29, 2005; see: RN 872412-08-3 structure, abstract, and patent family details (2 pages).
Database CAPLUS ACS on STN, 2006, DN 144:6815,See RN869970-58-1, 2005 structure, abstract, and patent family (1 pages).
Database CA (Online) Chemical Abstracts Service, Columbus, Ohio, US; "Amides of 2-(p-chlorophenoxy)-2-acid" retrieved from STN Database accession No. 1977:72243 abstracting Spanish Patent No. ES 427 013 A1 dated Jul. 16, 1976.
Database CAPLUS on STN (Columbus, OH, USA) No. 108:131815, Preparation and testing of f7-amino-1,3-dihydro-2H-imidazo[4,5-b]quinolin-2-ones as phosphodiesterase and bloodplatelet aggregation inhibitors, abstract, Meanwell, et al. (1988) see RN 113288-90-7.
Database CAPLUS on STN (Columbus, OH, USA) No. 118:255342, "Preparation of N-(heterocyclylcarbonyl)amino acids and analogs as prolyl endopeptidase inhibitors", abstract, Hosoda et al. (1993) see RN 147635-61-8.
Database CAPLUS on STN (Columbus, OH, USA) No. 1983: 107002, "1-(4-chlorophenyl)-1-cyclopentanecarboxylic acid derivatives", abstract, XP002514476. Abstract of Klomari, US Pat. Appl. Publ. 2004188324. Published 1983. 1 page.

Database CAPLUS on STN (Columbus, OH, USA) No. 2004:802077, "Zeolite SSZ-65 synthesis, properties, and use as petroleum and hydrocarbon refining catalysts", abstract, XP00251447. Abstract of Jpn. Pat. No. JP57156450 (Ihara Chemical Industry Co., Ltd.) Published 2004. 2 pages.
Davani et al. (2000) J. Biol. Chem. 275: 34841-34844.
De Costa et al., *J. Med. Chem.*, (1990), vol. 33(11), pp. 3100-3110.
Dorwald, Side Reactions in Organic Synthesis, 2005, Wiley: VCH, Weinheim p. IX of Preface pp. 1-15.
Draper et al. (2003) Nat. Genet. 34: 434-439.
Edwards et al. (1988) Lancet 2: 986-989.
Engeli, et al., (2004) Obes. Res. 12: 9-17.
Funder et al. (1988), Science 242: 583-585.
von Geldern et al., Biorg. Med. Chem. Lett., 2005, 15, 195.
Gomez-Monterrey., et al. "Stereospecific synthesis of (2lt, 3S)-3-amino-2-piperidineacetic acid derivatives for use as a conformational constraint in peptides" Tetrahedron Lett., 1993, 34, 3593-3594.
Greene, et al., Protective Groups in Organic Synthesis, 2d. Ed., Wiley & Sons, 1991*.
Grundy et al., Diagnosis and Management of the Metabolic Syndrome, *Circulation*, 2005, 112, 2735-2752.
Gu et al., "Discovery of 4-heteroarylbicyclo[2.2.2]oetyltriazoles as potent and selective inhibitors of 11β-HSD1: Novel therapeutic agents for the treatment of metabolic syndrome," *Bioorg. Med. Chem. Lett.*, 2005, 15, 5266-5269.
Hermanowski-Vosatka et al. *J. Exp. Med.*, 2005, 202, 517-527.
Higuchi and Stella, "Pro-drugs as Novel Delivery Systems," vol. 14 of the ACS Symposium Series, and in Bioreversible Carriers in Drug Design, ed. Edward B. Roche, American Pharmaceutical Association and Pergamon Press, 1987*.
Higuchi and Stella, "Pro-drugs as Novel Delivery Systems," vol. 14 of the ACS Symposium Series. Published Sep. 10, 1974, 251 pages.
Hosoda et al., "Preparation of N-(heterocyclylcarbonyl)amino acids and analogs as prolyl endopeptidase inhibitors", Database CAPLUS on STN (Columbus, OH, USA) No. 118:255342, Abstract, (1993) see RN 147635-61-8.
Huber, "11βHSD1 Inhibitors for Type 2 Diabetes: A Systematic Development Strategy to Assess Pharmacodynamic Activity and Obtain Proof-of-Concept in Man," IBC's 5$^{th}$ Annual Targeting Metabolic Disorders Conference, Feb. 26-27, 2007.
Huber, R. "11☐HSD1 Inhibition as an Entrée to Cardio-Metabolic Benefit in Type 2 Diabetes," presentation at Discovery on Target: Targeting Diabetes with Novel Therapeutics. Boston, MA, Oct. 22, 2008.
Huber, R. "Proof-of-Concept for llbeta-HSD1 Inhibition in Man: Evidence for Metabolic Improvements in Type 2 Diabetic Subjects after Short-Term INCB013739 Therapy." Presentation at Targeting Metabolic Disorders, Chapel Hill, NC Mar. 18, 2008.
Huber, R. "INCB013739, a Selective Inhibitor of 11b-Hydroxysteroid Dehydrogenase Type 1 (11☐HSD1), Improves Insulin Sensitivity and Lowers Plasma Cholesterol Over 28 Days in Patients with Type 2 Diabetes Mellitus." American Diabetes Association 68th Scientific Sessions, San Francisco, CA Jun. 9, 2008.
Huber, R. "Incyte 11☐HSD1 Inhibitor Program in Type 2, Diabetes Mellitus." 2008 Therapeutic Area Partnerships Conference. Philadelphia, PA Nov. 4, 2008.
Hughes, et al., "The Total Synthesis of (−)-Amathaspiramide F**," *Angew. Chem. Int. Ed*., 2002, 41(23) 4556-4559.
Irikura et al., "New antiulcer agents. I. Synthesis and biological activities of 1-acyl-2-, -3-, and -4-substituted benzamidopiperidines." *J. Med. Chem.* 1971, 14, pp. 357-361. (Chem. Abs. 92:174158).
Jausons-Loffreda et al. J. Biolumin and Chemilumin, 9:217-221 (1994).
Journal of Pharmaceutical Science, 66, 2 (1977).
Knochel et al. Angew. Chem. Int. Ed. 2003, 42, 4302-4320.
Knoops et al., "Generation of 3-piperidine(methan)amines and cyclic 3-piperidine-methanamines as potential substance P antagonists", *Tetrahedron*, (1997), vol. 53, pp. 12699-12716.
Known 2-iodomethylbenzoates, 168 pages. Results of a Chemical Abstracts Search cited in an Office Action dated Jul. 31, 2007 for U.S. Appl. No. 11/281,648. (2007).
Kotelevstev et al. (1997) Proc. Natl. Acad. Sci. 94: 14924-14929.

Kurukulasuriya, et al., (2003) Curr. Med. Chem. 10: 123-53.
Leonardi, A. et al., "Synthesis, Pharmacological Evaluation, and Structure—Activity Relationship and Qunatitative Structure—Activity Relationship Studies on Novel Derivatives of 2,4-Diamino-6,7-dimethoxyquinazoline alpha1-Adrenoceptor Antagonists" *J. Med. Chem.*, 1999, 42(3):427-437.
Lewis et al. *J. Chem. Soc. Perkin Trans.* 2, 1991, vol. 10. pp. 1625-1630.
Li et al. Syntheses and SAR of piperidin-3-yl ureas as potent and selective 11β-HSD-1 inhibitors, MEDI 54 Abstract of Presentation at the 233rd ACS National Meeting, Chicago, IL, Mar. 25-29, 2007.
Li et al. Syntheses and SAR of Piperidin-3-yl Ureas as Potent and Selective 11β-HSD-1 inhibitors, Presentation at the 233rd ACS National Meeting, Chicago, IL, Mar. 25-29, 2007.
Li, Y. et al. Syntheses and SAR of piperidin-3-yl ureas as potent and selective 11☐-HSD-1 inhibitors, MEDI 54 Abstract of Presentation at the 234th ACS National Meeting, Boston, MA Aug. 19-23, 2007.
Li, Y. et al. Syntheses and SAR of Piperidin-3-yl Ureas as Potent and Selective 11☐-HSD-1 inhibitors, Presentation at the 234th ACS National Meeting, Boston, MA Aug. 19-23, 2007.
Lindsay et al. (2003) J. Clin. Endocrinol. Metab. 88: 2738-2744.
Livingstone et al. (2000) Endocrinology 131: 560-563.
Louie, et al., Tetrahedron Lett., 1995, 36, 3609.
Low et al. (1994) J. Mol. Endocrin. 13: 167-174.
Lupien et al. (1998) Nat. Neurosci. 1: 69-73.
Mallams, et al., "Inhibitors of Farnesyl Protein Transferase, 4-Amido, 4-Carbamoyl, and 4-Carboxamido Derivatives of 1-(8-Chloro-6,11-dihydro-5H-benzo[5,6]-cyclohepta[1,2-b]pyridin-11-yl)piperazine and 1-(3-Bromo-8-chloro-6,11-dihydro-5H-benzo[5,6]cyclohepta[1,2-b]pyridin-11-yl)piperazine" *J. Med. Chem.*, 1998, 41(6):877-893.
Manthorpe et al., *Angew. Chem., Int. Ed.*, 2002, 41(13), 2338-2341.
Markees et al., *J. Am. Chem. Soc.*, 1949, vol. 71, pp. 2031-2035.
Martin-Martinez et al., "Synthesis and stereochemical structure-activity relationships of 1,3-dioxoperhydropyrido[1,2-c]pyrimidine derivatives: Potent and selective cholecystokinin-A receptor antagonists", *J. Med. Chem.*, 1997, vol. 40, pp. 3402-3407.
Martin, et al. "Do Structurally Similar Molecules Have Similar Biological Activity?", *J. Med. Chem.*, 2002, 45, 4350-4358.
Masuzaki et al. (2001) Science 294: 2166-2170.
Masuzaki et al. (2003) J. Clinical Invest. 112: 83-90.
Masuzaki, et al., (2003) Curr. Drug Targets Immune Endocr. Metabol. Disord. 3: 255-62.
Matsumoto et al., "Direkte Aminolyse von nicht aktivierten Estern bei hohm Druck," Angew. Chem., 1996, 98, 569-570.
Matsuzawa et al. (1999) Ann. N.Y. Acad. Sci. 892: 146-154.
McEwen and Sapolsky (1995) Curr. Opin. Neurobiol. 5: 205-216.
Meanwell, et al., "Preparation and testing of 7-amino-1,3-dihydro-2H-imidazo[4,5-b]quinolin-2-ones as phosphodiesterase and blood platelet aggregation inhibitors", Database CAPLUS on STN (Columbus, OH, USA) No. 108:131815, Abstract, (1988) see RN 113288-90-7.
Mehrotra et al., "Discovery of Novel 2,8-Diazaspiro[4,5]decanes as orally Active Glycoprotein IIb-IIIa Antagonist", J. Med. Chem., 2004, 47, pp. 2037-2061.
Messinger et al., "New inhibitors of 17b-hydroxysteroid dehydrogenasse type 1", Molecular and Cellular Endocrinology, 2006, 248, 192-198.
Miller and Chrousos (2001) Endocrinology and Metabolism, eds. Felig and Frohman (McGraw-Hill, New York), 4th Ed.: 387-524.
Miller et al., "The Adrenal Cortex" in Endocrinology and Metabolism 4th Edition, edited by Felig et al., McGraw-Hill, New York, pp. 387-524, (2001).
Mishani, et al. *Tetrahedron Lett.*, 1996, 37, 319.
Miyabe et al., "The total synthesis of (−)-balanol", *Synlett.*, 1997, pp. 580-582 (Chem. Abs. 130:38227).
Moeller et al., "Anodic Amide Oxidations in the Presence of Electron-Rich Phenyl Rings: Evidence for an Intramolecular Electron-Transfer Mechanism", *J. Org. Chem.*, 1991, 56(3):1058-1067.
Morris, et al., "Amathaspiramides A-F, Novel Brominated Alkaloids from the Marine Bryozoan," *J. Nat. Prod*, 1999, 62, 688-693.
Morton et al., *J. Biol. Chem.*, 2001, 276, 41293-41300.
Morton et al., *Diabetes*, 2004, 53, 931-938.

Moya et al., "Synthesis and Biological Evaluation of New Analogies of the Active Fungal Metabolites N-(2-Methyl-3-oxodecanoyl)-2-pyrroline and N-(2-Methyl-3-oxodec-8-enoyl)-2-pyrroline," *J. Agric. Food Chem.*, 1999, 47, 3866-3871.
Nojima, et al., Spiro Compounds Formation by the Reaction of Cycloalkene with Friedel-Crafts Catalyst. I. Reaction of Cyclohexene with Aluminum Chloride. The Rearrangement of Cyclohexylcyclohexene, *J. Org. Chem.*, 1966, 31 (12), pp. 3966-3969.
Ogawa et al. (1992) J. Clin. Invest. 90: 497-504.
Ogura, et al., "[1,4] Addition of (Methylthio p-Tolyl Sulfone to α,β-Unaturated Carbonyl Compounds", *J. Org. Chem.*, 1986, 51, pp. 508-512.
Ohta et al., "Preparation of heterocyclyl moiety-containing diamine derivatives as factor Xa inhibitors"; Chem. Abs. 141:106461 abstracting WO2004058715 dated Jul. 15, 2004.
Olivier et al., "Binding to albumin of spin-labeled derivatives of clofibric acid", European Journal of Medicinal Chemistry, 1985, 20(4), 302-8, abstract in Chemical Abstracts, STN Database Accession No. 1986:45271 (1986).
Pekala et al., "Synthesis of N-acyl derivatives of DL-trans-1,2-—cyclohexanol", *Acta Poloniae Pharmaceutical*, (1994), 51(4-5), 339-42, abstract in Chemical Abstracts, STN, Database Accession No. 1995:459419 (1995).
Pitt et al., New England J. Med. (1999), 341: 709-719.
Pitt et al., New England J. Med. (2003), 348: 1309-1321.
Poirier et al. "Inhibitors of type II 17b-hydroxysteroid dehydrogenase" Molecular and Cellular Endocrinology 2001, 171, 119-128.
Rajan et al. (1996) J. Neurosci. 16: 65-70.
Rask et al. (2001) J. Clin. Endocrinol. Metab. 86: 1418-1421.
Rauz et al. (2001) Invest. Ophthalmol. Vis. Sci. 42: 2037-2042.
Reaven (1993) Ann. Rev. Med. 44: 121-131.
Remington's Pharmaceutical Sciences, 17th ed., Mack Publishing Company, Easton, Pa., 1985, p. 1418.
RN 147635-61-8 structure, abstract, and patent family details (3 pages) abstracting Japanese Patent No. JP 04334357 dated Nov. 20, 1992.
RN 113288-90-7 structure, abstract, and patent family details (3 pages) abstracting Swiss Patent No. CH 676846 dated Mar. 15, 1991.
Roche (ed.) Bioreversible Carriers in Drug Design, American Pharmaceutical Association and Pergamon Press, Table of Contents and Chapter 1 by Higuchi, pp. i-vii and 1-12, (1987).
Sandeep et al., *Proc. Natl. Acad. Sci. USA*, 2004, 101, 6734-6739.
Schelsinger et al., "N-Substituted-Amides," *J. Am. Chem. Soc.*, 1956, 78: 6123-6127.
Shridhar et al., "Synthesis of new 3-methoxy-4-(acylamino)phenyl isothiocyanates and 4'-(isothiocyanatophenoxy)acetamides/isobutyramides as possible anthelmintic agents", *Indian Journal of Chemistry*, (1986), 25B(12), 1277-80, abstract retrieved from STN, Database Accession No. 1987:554038 (1987).
Stokes et al. (2000) Invest. Ophthalmol. Vis. Sci. 41: 1629-1683.
Suess, R. *Helvetica Chimica Acta*, 1977, 60(5), pp. 1650-1656 (English Abstract included).
Tanner et al., "Total synthesis of balanol. Part 2. Completion of the synthesis and investigation of the structure and reactivity of two key heterocyclic intermediates", *Tetrahedron*, 1997, vol. 53, pp. 4857-4858 (Chem. Abs. 126:277320).
Taylor et al., "On the Ritter reaction of cyclic hydroxyamines: synthesis of conformationally-restricted reduced amide dipeptide isosteres", *Tetrahedron Letters*, (1996), vol. 37, pp. 1297-1300.
Wajchenberg, *Endocr. Rev.*, 2000, 21: 697-738.
Wake et al. (2003) J. Clin. Endocrinol. Metab. 88: 3983-3988.
Walker et al. (1979) Hypertension 1: 287-291.
Wheatley et al., "Basic Ethers Derived from β-Hydroxyphenethylamines," J. Org. Chem., 1958, 23, 1360-1363.
Wilson et al. (1998) Proc. Natl. Acad. Sci. 95: 10200-10205.
Wojcik et al., "Catalytic Hydrogenation of Amides to Amines," *J. Am. Chem. Soc.*, 1934, 56, 2419-2424.
Wolff, "Burger's Medicinal Chemistry, 5ed, Part I", John Wiley & Sons, 1995, pp. 975-977.
Woolven et al. *J. Med. Chem.*, 2003, 46, 4428.

Xu, et al., "Synthesis of Aza/Oxaspiro-γ-lactams by Radical Translocation Cyclization Reastions," Synlett, 2005, 12, 1865-1868.
Yao, et al. Discovery of potent and selective 11β-HSD-1 Inhibitors, MEDI 228 Abstract of Presentation at the 233rd ACS National Meeting, Chicago, IL, Mar. 25-29, 2007.
Yao, Discovery of Potent and Orally Active Inhibitors of 11β-Hydroxysteroid Dehydrogenase I, presentation at the 233rd ACS National Meeting, Chicago, IL, Mar. 27, 2007.
Yao et al., "Preparation of cycloalkylcarbonylammes and heteroeyeloalkylcarbonylammes as 11β hydroxysteroid dchydrogenase type I inhibitors and mineraloeorticoid receptor antagonist and their use as pharmaceutical", Caplus English Abstract DN 144.6815, Nov. 2005.
Yau et al. (2001) Proc. Natl. Acad. Sci. 98: 4716-4721.
Yeh et al., "Discovery of orally active butyrolactam 11β-HSD1 inhibitors," Bioorg. Med. Chem. Lett., 2006, 16:5555-5560.
Yeh et al., "Synthesis and biological evaluation of heterocycle containing adamantine 11β-HSD1 inhibitors," Bioorg. Med. Chem. Lett., 16:5414-5419 (2006).
Yokoyama et al., "The First Effective Syntheses of Cyanoflurormethylated Amides, Thioamides, and Phosphorus Compounds Using 2-Cyano-2-fluoro-2-phenylacetonitrile and $ET_3GeNa$," Synthesis, 8: 1319-1324 (1999).
Zhuo. et al. Discovery and synthesis of nipecotic amide as novel, potent and selective 11β-HSD-1-inhibitors MEDI 48 Abstract, 233rd ACS National Meeting, Chicago, IL, Mar. 25-29, 2007.
Zhuo, J. et al. Discovery and synthesis of nipecotic amide as novel, potent and selective 11β-HSD-1-inhibitors MEDI 48 Abstract, 234th ACS National Meeting, Boston, MA Aug. 19-23, 2007.
Zhuo, J. et al. Discovery of Nipecotic Amides as Novel, Potent and Selective 11☐HSD1 Inhibitors, poster at the 234$^{th}$ ACS National Meeting, Boston, MA Aug. 19-23, 2007.
Zhuo et al. Discovery of Nipecotic Amides as Novel, Potent and Selective 11βHSD1 Inhibitors, poster at the 233rd ACS National Meeting, Chicago, IL, Mar. 25-29, 2007.
Amendment and Response in Reply to Office Action of Mar. 29, 2007 submitted Jun. 28, 2007—U.S. Appl. No. 11/281,648 (US20060122210A1).
Amendment in Reply to Action of Jul. 31, 2007 submitted Oct. 30, 2007—U.S. Appl. No. 11/281,648 (US20060122210A1).
Ex Parte Quayle Action—U.S. Appl. No. 11/122,309 (U.S. Publication No. 2005-0282858) dated Dec. 14, 2006.
Final Office Action dated Dec. 31, 2007 for U.S. Appl. No. 11/281,648.
Int'l Preliminary Report on Patentability—Int'l App. No. PCT/US05/041763 (WO2006/055752), (2006).
Int'l Preliminary Report on Patentability—Int'l App. No. PCT/US05/15559 (WO2005/110992) dated Nov. 7, 2006.
Int'l Preliminary Report on Patentability—Int'l App. No. PCT/US05/22411 (WO2006/002349) dated Dec. 28, 2006.
Int'l Preliminary Report on Patentability—Int'l App. No. PCT/US05/22412 (WO2006/002350) dated Dec. 28, 2006.
Int'l Preliminary Report on Patentability—Int'l App. No. PCT/US05/22307 (WO2006/012226) dated Dec. 28, 2006.
Int'l Preliminary Report on Patentability—Int'l App. No. PCT/US06/036652 (WO2007/038138) dated Mar. 28, 2008.
Int'l Preliminary Report on Patentability—Int'l App. No. PCT/US07/02360 (WO2007/089683) dated Aug. 5, 2008.
Int'l Preliminary Report on Patentability—Int'l App. No. PCT/US06/46309 (WO2007/067504) dated Jun. 11, 2008.
Int'l Preliminary Report on Patentability—Int'l App. No. PCT/US07/00695 (WO2007/084314) dated Jul. 15, 2008.
Int'l Preliminary Report on Patentability—Int'l App. No. PCT/US05/22170 (WO2006/012173) dated Jan. 11, 2007.
Int'l Preliminary Report on Patentability—Int'l App. No. PCT/US05/022434 (WO2006/002361) dated Dec. 28, 2006.
Int'l Preliminary Report on Patentability—Int'l App. No. PCT/US05/028201 (WO2006/020598) dated Feb. 13, 2007.
Int'l Preliminary Report on Patentability—Int'l App. No. PCT/US05/040550 dated May 30, 2007.
Int'l Search Report—Int'l App. No. PCT/US05/040550 (WO2006/053024) dated Jul. 17, 2007.
Int'l Search Report—Int'l App. No. PCT/US05/041763 (WO2006/055752) dated Apr. 24, 2007.
Int'l Search Report—Int'l App. No. PCT/US05/022434 (WO2006/002361) dated Mar. 31, 2006.
Int'l Search Report—Int'l App. No. PCT/US05/028201 (WO2006/020598) dated Nov. 6, 2006.
Int'l Search Report—Int'l App. No. PCT/US05/15559 (WO2005/110992) dated Aug. 15, 2005.
Int'l Search Report—Int'l App. No. PCT/US05/22411 (WO2006/002349) dated Oct. 20, 2005.
Int'l Search Report—Int'l App. No. PCT/US05/22412 (WO2006/002350) dated Nov. 2, 2005.
Int'l Search Report—Int'l App. No. PCT/US05/22307 (WO2006/012226) dated Apr. 5, 2006.
Int'l Search Report—Int'l App. No. PCT/US05/22170 (WO2006/012173) dated Oct. 18, 2005.
Int'l Search Report—Int'l App. No. PCT/US06/036652 (WO2007/038138) dated Feb. 4, 2007.
Int'l Search Report—Int'l App. No. PCT/US06/12227 dated Jul. 17, 2006.
Int'l Search Report—Int'l App. No. PCT/US06/46309 (WO2007/067504) dated Jul. 9, 2007.
Int'l Search Report—Int'l App. No. PCT/US07/02360 (WO2007/089683) dated Jun. 19, 2007.
Int'l Search Report for PCT/US05/22308 (WO2006/012227), dated Dec. 2, 2005.
Int'l Search Report for PCT/US2006/046309 (WO2007/067504) dated Aug. 28, 2007.
Int'l Search Report—Int'l App. No. PCT/US07/00695 (WO2007/084314) dated Jan. 31, 2008.
Int'l Search Report—Int'l App. No. PCT/US07/063050 (WO2007/101270) dated Sep. 7, 2007.
Int'l Search Report—Int'l App. No. PCT/US07/063055 (WO2007/103719) dated Oct. 22, 2007.
Int'l Search Report—Int'l App. No. PCT/US07/067753 (WO2007/130898) dated Oct. 2, 2007.
Int'l Search Report—Int'l App. No. PCT/US07/069033 (WO2007/137066) dated Apr. 28, 2008.
Interview Summary—U.S. Appl. No. 11/784,450 (U.S. Publication No. 2007-0179142) dated Jul. 14, 2008.
Notification of the Results of Substantive Examination dated Mar. 6, 2009 for Vietnamese Appin. 1-2007-00135.
Office Action—Chilean App. No. 3389-2006 dated Aug. 8, 2008.
Office Action—Eurasian App. No. 200602062/2006120048 dated Dec. 20, 2007.
Office Action—Eurasian App. No. 200700117 dated Mar. 27, 2008.
Office Action—Eurasian Pat. App. No. 200700118 dated Mar. 20, 2008.
Office Action—Georgian App. No. AP2005 009823 dated Nov. 22, 2007.
Office Action—Georgian App. No. AP2005010125 dated Feb. 11, 2008.
Office Action—Georgian Pat. App. No. AP2005009824 dated Nov. 22, 2007.
Office Action—U.S. Appl. No. 11/159,724 (U.S. Publication No. 2006-0009471) dated Mar. 24, 2008.
Office Action—U.S. Appl. No. 11/159,862 (U.S. Publication No. 2005-0288338) dated May 6, 2008.
Office Action—U.S. Appl. No. 11/159,865 (U.S. Publication No. 2005-0288329) dated Apr. 6, 2008.
Office Action—U.S. Appl. No. 11/281,648 (U.S. Publication No. 2006-0122210) dated Jul. 31, 2007.
Office Action—U.S. Appl. No. 11/281,648 (U.S. Publication No. 2006-0122210) dated Mar. 29, 2007.
Office Action—U.S. Appl. No. 11/784,450 (U.S. Publication No. 2007-0179142) dated Dec. 13, 2007.
Office Action mailed Mar. 4, 2008—U.S. Appl. No. 11/199,763 (20060122197A1).
Opposition—Costa Rican App. No. 8793 dated Aug. 5, 2008.
Opposition—Ecuadorian App. No. SP-06-7114 dated May 23, 2007.
Partial European Search Report—European App. No. 05762543.6 dated Nov. 30, 2007.

Preliminary Examination Results—Vietnamese App. No. 1-2006-02007 dated Apr. 27, 2007.

Search Report—Eurasian App. 200701036 dated Dec. 10, 2007.

Search Report—Georgian App. No. AP2005009920 dated Apr. 21, 2008.

Search Report dated Dec. 29, 2008 for Georgian Appln. No. AP2005 009823.

Search Report—Singapore App. No. 200700845-1 dated May 19, 2008.

Search Report—Singapore App. No. SG200607426 dated Dec. 14, 2007.

Supplementary European Search Report—European App. No. 05763245.7 dated Apr. 9, 2008.

Supplementary European Search Report—European App. No. 05763380.2 dated Dec. 6, 2007.

Supplementary Partial EP Search Report—European App. No. 05763383.6 dated Dec. 3, 2007.

Supplementary Partial European Search Report dated Feb. 11, 2009 in connection with EP App. No. 05745656.8.

N-SUBSTITUTED PIPERIDINES AND THEIR USE AS PHARMACEUTICALS

CROSS REFERENCE TO RELATED APPLICATIONS

This application is a divisional of U.S. application Ser. No. 11/159,448, filed Jun. 23, 2005, which is pending, and claims the benefit of U.S. Ser. Nos. 60/582,557, filed Jun. 24, 2004; 60/614,570, filed Sep. 30, 2004; and 60/686,840, filed Jun. 2, 2005, the disclosures of which are incorporated herein by reference in their entireties.

FIELD OF THE INVENTION

The present invention relates to modulators of 11-β hydroxyl steroid dehydrogenase type 1 (11βHSD1) and/or mineralocorticoid receptor (MR), compositions thereof and methods of using the same.

BACKGROUND OF THE INVENTION

Glucocorticoids are steroid hormones that regulate fat metabolism, function and distribution. In vertebrates, glucocorticoids also have profound and diverse physiological effects on development, neurobiology, inflammation, blood pressure, metabolism and programmed cell death. In humans, the primary endogenously-produced glucocorticoid is cortisol. Cortisol is synthesized in the zona fasciculate of the adrenal cortex under the control of a short-term neuroendocrine feedback circuit called the hypothalamic-pituitary-adrenal (HPA) axis. Adrenal production of cortisol proceeds under the control of adrenocorticotrophic hormone (ACTH), a factor produced and secreted by the anterior pituitary. Production of ACTH in the anterior pituitary is itself highly regulated, driven by corticotropin releasing hormone (CRH) produced by the paraventricular nucleus of the hypothalamus. The HPA axis maintains circulating cortisol concentrations within restricted limits, with forward drive at the diurnal maximum or during periods of stress, and is rapidly attenuated by a negative feedback loop resulting from the ability of cortisol to suppress ACTH production in the anterior pituitary and CRH production in the hypothalamus.

Aldosterone is another hormone produced by the adrenal cortex; aldosterone regulates sodium and potassium homeostasis. Fifty years ago, a role for aldosterone excess in human disease was reported in a description of the syndrome of primary aldosteronism (Conn, (1955), J. Lab. Clin. Med. 45: 6-17). It is now clear that elevated levels of aldosterone are associated with deleterious effects on the heart and kidneys, and are a major contributing factor to morbidity and mortality in both heart failure and hypertension.

Two members of the nuclear hormone receptor superfamily, glucocorticoid receptor (GR) and mineralocorticoid receptor (MR), mediate cortisol function in vivo, while the primary intracellular receptor for aldosterone is the MR. These receptors are also referred to as 'ligand-dependent transcription factors,' because their functionality is dependent on the receptor being bound to its ligand (for example, cortisol); upon ligand-binding these receptors directly modulate transcription via DNA-binding zinc finger domains and transcriptional activation domains.

Historically, the major determinants of glucocorticoid action were attributed to three primary factors: 1) circulating levels of glucocorticoid (driven primarily by the HPA axis), 2) protein binding of glucocorticoids in circulation, and 3) intracellular receptor density inside target tissues. Recently, a fourth determinant of glucocorticoid function was identified: tissue-specific pre-receptor metabolism by glucocorticoid-activating and -inactivating enzymes. These 11-beta-hydroxysteroid dehydrogenase (11-β-HSD) enzymes act as pre-receptor control enzymes that modulate activation of the GR and MR by regulation of glucocorticoid hormones. To date, two distinct isozymes of 11-beta-HSD have been cloned and characterized: 11βHSD1 (also known as 11-beta-HSD type 1, 11betaHSD1, HSD11B1, HDL, and HSD11L) and 11βHSD2. 11βHSD1 and 11βHSD2 catalyze the interconversion of hormonally active cortisol (corticosterone in rodents) and inactive cortisone (11-dehydrocorticosterone in rodents). 11βHSD1 is widely distributed in rat and human tissues; expression of the enzyme and corresponding mRNA have been detected in lung, testis, and most abundantly in liver and adipose tissue. 11βHSD1 catalyzes both 11-beta-dehydrogenation and the reverse 11-oxoreduction reaction, although 11βHSD1 acts predominantly as a NADPH-dependent oxoreductase in intact cells and tissues, catalyzing the activation of cortisol from inert cortisone (Low et al. (1994) J. Mol. Endocrin. 13: 167-174) and has been reported to regulate glucocorticoid access to the GR. Conversely, 11βHSD2 expression is found mainly in mineralocorticoid target tissues such as kidney, placenta, colon and salivary gland, acts as an NAD-dependent dehydrogenase catalyzing the inactivation of cortisol to cortisone (Albiston et al. (1994) Mol. Cell. Endocrin. 105: R11-R17), and has been found to protect the MR from glucocorticoid excess, such as high levels of receptor-active cortisol (Blum, et al., (2003) Prog. Nucl. Acid Res. Mol. Biol. 75:173-216).

In vitro, the MR binds cortisol and aldosterone with equal affinity. The tissue specificity of aldosterone activity, however, is conferred by the expression of 11βHSD2 (Funder et al. (1988), Science 242: 583-585). The inactivation of cortisol to cortisone by 11βHSD2 at the site of the MR enables aldosterone to bind to this receptor in vivo. The binding of aldosterone to the MR results in dissociation of the ligand-activated MR from a multiprotein complex containing chaperone proteins, translocation of the MR into the nucleus, and its binding to hormone response elements in regulatory regions of target gene promoters. Within the distal nephron of the kidney, induction of serum and glucocorticoid inducible kinase-1 (sgk-1) expression leads to the absorption of $Na^+$ ions and water through the epithelial sodium channel, as well as potassium excretion with subsequent volume expansion and hypertension (Bhargava et al., (2001), Endo 142: 1587-1594).

In humans, elevated aldosterone concentrations are associated with endothelial dysfunction, myocardial infarction, left ventricular atrophy, and death. In attempts to modulate these ill effects, multiple intervention strategies have been adopted to control aldosterone overactivity and attenuate the resultant hypertension and its associated cardiovascular consequences. Inhibition of angiotensin-converting enzyme (ACE) and blockade of the angiotensin type 1 receptor (AT1R) are two strategies that directly impact the rennin-angiotensin-aldosterone system (RAAS). However, although ACE inhibition and AT1R antagonism initially reduce aldosterone concentrations, circulating concentrations of this hormone return to baseline levels with chronic therapy (known as 'aldosterone escape'). Importantly, co-administration of the MR antagonist Spironolactone or Eplerenone directly blocks the deleterious effects of this escape mechanism and dramatically reduces patient mortality (Pitt et al., New England J. Med. (1999), 341: 709-719; Pitt et al., New England J. Med. (2003), 348: 1309-1321). Therefore, MR antagonism may be an important treatment strategy for many patients with hypertension and cardiovascular disease, particularly those hypertensive patients at risk for target-organ damage.

Mutations in either of the genes encoding the 11-beta-HSD enzymes are associated with human pathology. For example, 11βHSD2 is expressed in aldosterone-sensitive tissues such as the distal nephron, salivary gland, and colonic mucosa where its cortisol dehydrogenase activity serves to protect the intrinsically non-selective MR from illicit occupation by cortisol (Edwards et al. (1988) Lancet 2: 986-989). Individuals with mutations in 11βHSD2 are deficient in this cortisol-inactivation activity and, as a result, present with a syndrome of apparent mineralocorticoid excess (also referred to as 'SAME') characterized by hypertension, hypokalemia, and sodium retention (Wilson et al. (1998) Proc. Natl. Acad. Sci. 95: 10200-10205). Likewise, mutations in 11βHSD1, a primary regulator of tissue-specific glucocorticoid bioavailability, and in the gene encoding a co-localized NADPH-generating enzyme, hexose 6-phosphate dehydrogenase (H6PD), can result in cortisone reductase deficiency (CRD), in which activation of cortisone to cortisol does not occur, resulting in adrenocorticotropin-mediated androgen excess. CRD patients excrete virtually all glucocorticoids as cortisone metabolites (tetrahydrocortisone) with low or absent cortisol metabolites (tetrahydrocortisols). When challenged with oral cortisone, CRD patients exhibit abnormally low plasma cortisol concentrations. These individuals present with ACTH-mediated androgen excess (hirsutism, menstrual irregularity, hyperandrogenism), a phenotype resembling polycystic ovary syndrome (PCOS) (Draper et al. (2003) Nat. Genet. 34: 434-439).

The importance of the HPA axis in controlling glucocorticoid excursions is evident from the fact that disruption of homeostasis in the HPA axis by either excess or deficient secretion or action results in Cushing's syndrome or Addison's disease, respectively (Miller and Chrousos (2001) Endocrinology and Metabolism, eds. Felig and Frohman (McGraw-Hill, New York), 4$^{th}$ Ed.: 387-524). Patients with Cushing's syndrome (a rare disease characterized by systemic glucocorticoid excess originating from the adrenal or pituitary tumors) or receiving glucocorticoid therapy develop reversible visceral fat obesity. Interestingly, the phenotype of Cushing's syndrome patients closely resembles that of Reaven's metabolic syndrome (also known as Syndrome X or insulin resistance syndrome) the symptoms of which include visceral obesity, glucose intolerance, insulin resistance, hypertension, type 2 diabetes and hyperlipidemia (Reaven (1993) Ann. Rev. Med. 44: 121-131). However, the role of glucocorticoids in prevalent forms of human obesity has remained obscure because circulating glucocorticoid concentrations are not elevated in the majority of metabolic syndrome patients. In fact, glucocorticoid action on target tissue depends not only on circulating levels but also on intracellular concentration, locally enhanced action of glucocorticoids in adipose tissue and skeletal muscle has been demonstrated in metabolic syndrome. Evidence has accumulated that enzyme activity of 11βHSD1, which regenerates active glucocorticoids from inactive forms and plays a central role in regulating intracellular glucocorticoid concentration, is commonly elevated in fat depots from obese individuals. This suggests a role for local glucocorticoid reactivation in obesity and metabolic syndrome.

Given the ability of 11βHSD1 to regenerate cortisol from inert circulating cortisone, considerable attention has been given to its role in the amplification of glucocorticoid function. 11βHSD1 is expressed in many key GR-rich tissues, including tissues of considerable metabolic importance such as liver, adipose, and skeletal muscle, and, as such, has been postulated to aid in the tissue-specific potentiation of glucocorticoid-mediated antagonism of insulin function. Considering a) the phenotypic similarity between glucocorticoid excess (Cushing's syndrome) and the metabolic syndrome with normal circulating glucocorticoids in the latter, as well as b) the ability of 11βHSD1 to generate active cortisol from inactive cortisone in a tissue-specific manner, it has been suggested that central obesity and the associated metabolic complications in syndrome X result from increased activity of 11βHSD1 within adipose tissue, resulting in 'Cushing's disease of the omentum' (Bujalska et al. (1997) Lancet 349: 1210-1213). Indeed, 11βHSD1 has been shown to be upregulated in adipose tissue of obese rodents and humans (Livingstone et al. (2000) Endocrinology 131: 560-563; Rask et al. (2001) J. Clin. Endocrinol. Metab. 86: 1418-1421; Lindsay et al. (2003) J. Clin. Endocrinol. Metab. 88: 2738-2744; Wake et al. (2003) J. Clin. Endocrinol. Metab. 88: 3983-3988).

Additional support for this notion has come from studies in mouse transgenic models. Adipose-specific overexpression of 11βHSD1 under the control of the aP2 promoter in mouse produces a phenotype remarkably reminiscent of human metabolic syndrome (Masuzaki et al. (2001) Science 294: 2166-2170; Masuzaki et al. (2003) J. Clinical Invest. 112: 83-90). Importantly, this phenotype occurs without an increase in total circulating corticosterone, but rather is driven by a local production of corticosterone within the adipose depots. The increased activity of 11βHSD1 in these mice (2-3 fold) is very similar to that observed in human obesity (Rask et al. (2001) J. Clin. Endocrinol. Metab. 86: 1418-1421). This suggests that local 11βHSD1-mediated conversion of inert glucocorticoid to active glucocorticoid can have profound influences whole body insulin sensitivity.

Based on this data, it would be predicted that the loss of 11βHSD1 would lead to an increase in insulin sensitivity and glucose tolerance due to a tissue-specific deficiency in active glucocorticoid levels. This is, in fact, the case as shown in studies with 11βHSD1-deficient mice produced by homologous recombination (Kotelevstev et al. (1997) Proc. Natl. Acad. Sci. 94: 14924-14929; Morton et al. (2001) J. Biol. Chem. 276: 41293-41300; Morton et al. (2004) Diabetes 53: 931-938). These mice are completely devoid of 11-keto reductase activity, confirming that 11βHSD1 encodes the only activity capable of generating active corticosterone from inert 11-dehydrocorticosterone. 11βHSD1-deficient mice are resistant to diet- and stress-induced hyperglycemia, exhibit attenuated induction of hepatic gluconeogenic enzymes (PEPCK, G6P), show increased insulin sensitivity within adipose, and have an improved lipid profile (decreased triglycerides and increased cardio-protective HDL). Additionally, these animals show resistance to high fat diet-induced obesity. Taken together, these transgenic mouse studies confirm a role for local reactivation of glucocorticoids in controlling hepatic and peripheral insulin sensitivity, and suggest that inhibition of 11βHSD1 activity may prove beneficial in treating a number of glucocorticoid-related disorders, including obesity, insulin resistance, hyperglycemia, and hyperlipidemia.

Data in support of this hypothesis has been published. Recently, it was reported that 11βHSD1 plays a role in the pathogenesis of central obesity and the appearance of the metabolic syndrome in humans. Increased expression of the 11βHSD1 gene is associated with metabolic abnormalities in obese women and that increased expression of this gene is suspected to contribute to the increased local conversion of cortisone to cortisol in adipose tissue of obese individuals (Engeli, et al., (2004) Obes. Res. 12: 9-17).

A new class of 11βHSD1 inhibitors, the arylsulfonamidothiazoles, was shown to improve hepatic insulin sensitivity and reduce blood glucose levels in hyperglycemic strains of mice (Barf et al. (2002) J. Med. Chem. 45: 3813-3815; Alberts et al. Endocrinology (2003) 144: 4755-4762). Furthermore, it was recently reported that selective inhibitors of 11βHSD1 can ameliorate severe hyperglycemia in genetically diabetic obese mice. Thus, 11βHSD1 is a promising pharmaceutical target for the treatment of the Metabolic Syndrome (Masuzaki, et al., (2003) Curr. Drug Targets Immune Endocr. Metabol. Disord. 3: 255-62).

A. Obesity and Metabolic Syndrome

As described above, multiple lines of evidence suggest that inhibition of 11βHSD1 activity can be effective in combating obesity and/or aspects of the metabolic syndrome cluster, including glucose intolerance, insulin resistance, hyperglycemia, hypertension, and/or hyperlipidemia. Glucocorticoids are known antagonists of insulin action, and reductions in local glucocorticoid levels by inhibition of intracellular cortisone to cortisol conversion should increase hepatic and/or peripheral insulin sensitivity and potentially reduce visceral adiposity. As described above, 11βHSD1 knockout mice are resistant to hyperglycemia, exhibit attenuated induction of key hepatic gluconeogenic enzymes, show markedly increased insulin sensitivity within adipose, and have an improved lipid profile. Additionally, these animals show resistance to high fat diet-induced obesity (Kotelevstev et al. (1997) Proc. Natl. Acad. Sci. 94: 14924-14929; Morton et al. (2001) J. Biol. Chem. 276: 41293-41300; Morton et al. (2004) Diabetes 53: 931-938). Thus, inhibition of 11βHSD1 is predicted to have multiple beneficial effects in the liver, adipose, and/or skeletal muscle, particularly related to alleviation of component(s) of the metabolic syndrome and/or obesity.

B. Pancreatic Function

Glucocorticoids are known to inhibit the glucose-stimulated secretion of insulin from pancreatic beta-cells (Billaudel and Sutter (1979) Horm. Metab. Res. 11: 555-560). In both Cushing's syndrome and diabetic Zucker fa/fa rats, glucose-stimulated insulin secretion is markedly reduced (Ogawa et al. (1992) J. Clin. Invest. 90: 497-504). 11βHSD1 mRNA and activity has been reported in the pancreatic islet cells of ob/ob mice and inhibition of this activity with carbenoxolone, an 11βHSD1 inhibitor, improves glucose-stimulated insulin release (Davani et al. (2000) J. Biol. Chem. 275: 34841-34844). Thus, inhibition of 11βHSD1 is predicted to have beneficial effects on the pancreas, including the enhancement of glucose-stimulated insulin release.

C. Cognition and Dementia

Mild cognitive impairment is a common feature of aging that may be ultimately related to the progression of dementia. In both aged animals and humans, inter-individual differences in general cognitive function have been linked to variability in the long-term exposure to glucocorticoids (Lupien et al. (1998) Nat. Neurosci. 1: 69-73). Further, dysregulation of the HPA axis resulting in chronic exposure to glucocorticoid excess in certain brain subregions has been proposed to contribute to the decline of cognitive function (McEwen and Sapolsky (1995) Curr. Opin. Neurobiol. 5: 205-216). 11βHSD1 is abundant in the brain, and is expressed in multiple subregions including the hippocampus, frontal cortex, and cerebellum (Sandeep et al. (2004) Proc. Natl. Acad. Sci. Early Edition: 1-6). Treatment of primary hippocampal cells with the 11βHSD1 inhibitor carbenoxolone protects the cells from glucocorticoid-mediated exacerbation of excitatory amino acid neurotoxicity (Rajan et al. (1996) J. Neurosci. 16: 65-70). Additionally, 11βHSD1-deficient mice are protected from glucocorticoid-associated hippocampal dysfunction that is associated with aging (Yau et al. (2001) Proc. Natl. Acad. Sci. 98: 4716-4721). In two randomized, double-blind, placebo-controlled crossover studies, administration of carbenoxolone improved verbal fluency and verbal memory (Sandeep et al. (2004) Proc. Natl. Acad. Sci. Early Edition: 1-6). Thus, inhibition of 11βHSD1 is predicted to reduce exposure to glucocorticoids in the brain and protect against deleterious glucocorticoid effects on neuronal function, including cognitive impairment, dementia, and/or depression.

D. Intra-Ocular Pressure

Glucocorticoids can be used topically and systemically for a wide range of conditions in clinical ophthalmology. One particular complication with these treatment regimens is corticosteroid-induced glaucoma. This pathology is characterized by a significant increase in intra-ocular pressure (IOP). In its most advanced and untreated form, IOP can lead to partial visual field loss and eventually blindness. IOP is produced by the relationship between aqueous humour production and drainage. Aqueous humour production occurs in the non-pigmented epithelial cells (NPE) and its drainage is through the cells of the trabecular meshwork. 11βHSD1 has been localized to NPE cells (Stokes et al. (2000) Invest. Ophthalmol. Vis. Sci. 41: 1629-1683; Rauz et al. (2001) Invest. Ophthalmol. Vis. Sci. 42: 2037-2042) and its function is likely relevant to the amplification of glucocorticoid activity within these cells. This notion has been confirmed by the observation that free cortisol concentration greatly exceeds that of cortisone in the aqueous humour (14:1 ratio). The functional significance of 11βHSD1 in the eye has been evaluated using the inhibitor carbenoxolone in healthy volunteers (Rauz et al. (2001) Invest. Ophthalmol. Vis. Sci. 42: 2037-2042). After seven days of carbenoxolone treatment, IOP was reduced by 18%. Thus, inhibition of 11βHSD1 in the eye is predicted to reduce local glucocorticoid concentrations and IOP, producing beneficial effects in the management of glaucoma and other visual disorders.

E. Hypertension

Adipocyte-derived hypertensive substances such as leptin and angiotensinogen have been proposed to be involved in the pathogenesis of obesity-related hypertension (Matsuzawa et al. (1999) Ann. N.Y. Acad. Sci. 892: 146-154; Wajchenberg (2000) Endocr. Rev. 21: 697-738). Leptin, which is secreted in excess in aP2-11βHSD1 transgenic mice (Masuzaki et al. (2003) J. Clinical Invest. 112: 83-90), can activate various sympathetic nervous system pathways, including those that regulate blood pressure (Matsuzawa et al. (1999) Ann. N.Y. Acad. Sci. 892: 146-154). Additionally, the renin-angiotensin system (RAS) has been shown to be a major determinant of blood pressure (Walker et al. (1979) Hypertension 1: 287-291). Angiotensinogen, which is produced in liver and adipose tissue, is the key substrate for renin and drives RAS activation. Plasma angiotensinogen levels are markedly elevated in aP2-11βHSD1 transgenic mice, as are angiotensin II and aldosterone (Masuzaki et al. (2003) J. Clinical Invest. 112: 83-90). These forces likely drive the elevated blood pressure observed in aP2-11βHSD1 transgenic mice. Treatment of these mice with low doses of an angiotensin II receptor antagonist abolishes this hypertension (Masuzaki et al. (2003) J. Clinical Invest. 112: 83-90). This data illustrates the importance of local glucocorticoid reactivation in adipose tissue and liver, and suggests that hypertension may be caused or exacerbated by 11βHSD1 activity. Thus, inhibition of 11βHSD1 and reduction in adipose and/or hepatic glucocorticoid levels is predicted to have beneficial effects on hypertension and hypertension-related cardiovascular disorders.

F. Bone Disease

Glucocorticoids can have adverse effects on skeletal tissues. Continued exposure to even moderate glucocorticoid doses can result in osteoporosis (Cannalis (1996) J. Clin. Endocrinol. Metab. 81: 3441-3447) and increased risk for fractures. Experiments in vitro confirm the deleterious effects of glucocorticoids on both bone-resorbing cells (also known as osteoclasts) and bone forming cells (osteoblasts). 11βHSD1 has been shown to be present in cultures of human primary osteoblasts as well as cells from adult bone, likely a mixture of osteoclasts and osteoblasts (Cooper et al. (2000) Bone 27: 375-381), and the 11βHSD1 inhibitor carbenoxolone has been shown to attenuate the negative effects of glucocorticoids on bone nodule formation (Bellows et al. (1998) Bone 23: 119-125). Thus, inhibition of 11βHSD1 is predicted to decrease the local glucocorticoid concentration within osteoblasts and osteoclasts, producing beneficial effects in various forms of bone disease, including osteoporosis.

Small molecule inhibitors of 11βHSD1 are currently being developed to treat or prevent 11βHSD1-related diseases such as those described above. For example, certain amide-based inhibitors are reported in WO 2004/089470, WO 2004/089896, WO 2004/056745, and WO 2004/065351.

Antagonists of 11βHSD1 have been evaluated in human clinical trials (Kurukulasuriya™, et al., (2003) Curr. Med. Chem. 10: 123-53).

In light of the experimental data indicating a role for 11βHSD1 in glucocorticoid-related disorders, metabolic syndrome, hypertension, obesity, insulin resistance, hyperglycemia, hyperlipidemia, type 2 diabetes, androgen excess (hirsutism, menstrual irregularity, hyperandrogenism) and polycystic ovary syndrome (PCOS), therapeutic agents aimed at augmentation or suppression of these metabolic pathways, by modulating glucocorticoid signal transduction at the level of 11βHSD1 are desirable.

Furthermore, because the MR binds to aldosterone (its natural ligand) and cortisol with equal affinities, compounds that are designed to interact with the active site of 11βHSD1 (which binds to cortisone/cortisol) may also interact with the MR and act as antagonists. Because the MR is implicated in heart failure, hypertension, and related pathologies including atherosclerosis, arteriosclerosis, coronary artery disease, thrombosis, angina, peripheral vascular disease, vascular wall damage, and stroke, MR antagonists are desirable and may also be useful in treating complex cardiovascular, renal, and inflammatory pathologies including disorders of lipid metabolism including dyslipidemia or hyperlipoproteinaemia, diabetic dyslipidemia, mixed dyslipidemia, hypercholesterolemia, hypertriglyceridemia, as well as those associated with type 1 diabetes, type 2 diabetes, obesity, metabolic syndrome, and insulin resistance, and general aldosterone-related target-organ damage.

As evidenced herein, there is a continuing need for new and improved drugs that target 11βHSD1 and/or MR. The compounds, compositions and methods described herein help meet this and other needs.

SUMMARY OF THE INVENTION

The present invention provides, inter alia, compounds of Formula I:

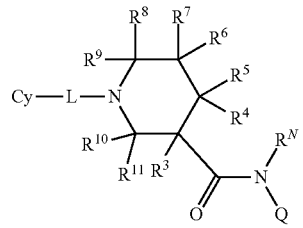

or pharmaceutically acceptable salts or prodrugs thereof, wherein constituent members are defined herein.

The present invention further provides compositions comprising compounds of the invention and a pharmaceutically acceptable carrier.

The present invention further provides methods of modulating 11βHSD1 or MR by contacting said 11βHSD1 or MR with a compound of the invention.

The present invention further provides methods of inhibiting 11βHSD1 or MR by contacting said 11βHSD1 or MR with a compound of the invention.

The present invention further provides methods of inhibiting conversion of cortisone to cortisol in a cell.

The present invention further provides methods of inhibiting production of cortisol in a cell.

The present invention further provides methods of increasing insulin sensitivity in a cell.

The present invention further provides methods of treating diseases associated with activity or expression of 11βHSD1 or MR.

DETAILED DESCRIPTION

The present invention is directed to, inter alia, compounds of Formula I:

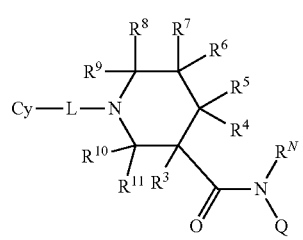

or pharmaceutically acceptable salt or prodrug thereof, wherein:

Cy is aryl, heteroaryl, cycloalkyl, or heterocycloalkyl, each optionally substituted with 1, 2, 3, 4 or 5 —W—X—Y—Z;

L is absent, $SO_2$, C(O), C(O)O or C(O)NR$^g$;

Q is cycloalkyl or heterocycloalkyl, each optionally substituted with 1, 2, 3, 4 or 5 —W'—X'—Y'—Z';

or Q is —$(CR^{1a}R^{1b})_m$-A;

A is aryl, heteroaryl, cycloalkyl, or heterocycloalkyl, each optionally substituted with 1, 2, 3, 4 or 5 —W'—X'—Y'—Z';

$R^{1a}$ and $R^{1b}$ are each, independently, H, halo, OH, $C_{1-4}$ alkyl, $C_{1-4}$ haloalkyl, $C_{1-4}$ hydroxylalkyl, $C_{1-4}$ alkoxy, $C_{1-4}$ haloalkoxy or $C_{1-4}$ hydroxylalkoxy;

m is 1, 2, 3 or 4;

$R^N$ is H, $C_{1-6}$ alkyl, aryl, heteroaryl, $C_{3-7}$ cycloalkyl, heterocyclylalkyl, arylalkyl, heteroarylalkyl, ($C_{3-7}$ cycloalkyl) alkyl, or heterocycloalkylalkyl;

$R^3$, $R^4$, $R^5$, $R^6$, $R^7$, $R^8$, $R^9$, $R^{10}$ and $R^{11}$ are each, independently, H, $OC(O)R^{a'}$, $OC(O)OR^{b'}$, $C(O)OR^{b'}$, $OC(O)NR^{c'}R^{d'}$, $NR^{c'}R^{d'}$, $NR^{c'}C(O)R^{a'}$, $NR^{c'}C(O)OR^{b'}$, $S(O)R^{a'}$, $S(O)NR^{c'}R^{d'}$, $S(O)_2R^{a'}$, $S(O)_2NR^{c'}R^{d'}$, $OR^{b'}$, $SR^{b'}$, $C_{1-10}$ alkyl, $C_{1-10}$ haloalkyl, $C_{2-10}$ alkenyl, $C_{2-10}$ alkynyl, aryl, cycloalkyl, heteroaryl, heterocycloalkyl, arylalkyl, heteroarylalkyl, cycloalkylalkyl or heterocycloalkylalkyl, wherein said $C_{1-10}$ alkyl, $C_{1-10}$ haloalkyl, $C_{2-10}$ alkenyl, $C_{2-10}$ alkynyl, aryl, cycloalkyl, heteroaryl, heterocycloalkyl, arylalkyl, heteroarylalkyl, cycloalkylalkyl or heterocycloalkylalkyl is optionally substituted by $R^{14}$;

or $R^4$ and $R^5$ together with the carbon atom to which they are attached form a 3-14 membered cycloalkyl or heterocycloalkyl group which is optionally substituted by $R^{14}$;

or $R^6$ and $R^7$ together with the carbon atom to which they are attached form a 3-14 membered cycloalkyl or heterocycloalkyl group which is optionally substituted by $R^{14}$;

or $R^8$ and $R^9$ together with the carbon atom to which they are attached form a 3-14 membered cycloalkyl or heterocycloalkyl group which is optionally substituted by $R^{14}$;

or $R^{10}$ and $R^{11}$ together with the carbon atom to which they are attached form a 3-14 membered cycloalkyl or heterocycloalkyl group which is optionally substituted by $R^{14}$;

or $R^4$ and $R^6$ together with the carbon atom to which they are attached form a 3-7 membered fused cycloalkyl group or 3-7 membered fused heterocycloalkyl group which is optionally substituted by $R^{14}$;

or $R^6$ and $R^8$ together with the carbon atom to which they are attached form a 3-7 membered fused cycloalkyl group or 3-7 membered fused heterocycloalkyl group which is optionally substituted by $R^{14}$;

or $R^4$ and $R^9$ together form a $C_{1-3}$ alkylene bridge which is optionally substituted by $R^{14}$;

or $R^4$ and $R^{10}$ together form a $C_{1-3}$ alkylene bridge which is optionally substituted by $R^{14}$;

or $R^3$ and $R^7$ together form a $C_{1-3}$ alkylene bridge which is optionally substituted by $R^{14}$;

or $R^3$ and $R^9$ together form a $C_{1-3}$ alkylene bridge which is optionally substituted by $R^{14}$;

or $R^6$ and $R^{10}$ together form a $C_{1-3}$ alkylene bridge which is optionally substituted by $R^{14}$;

or $R^9$ and $R^{10}$ together form a $C_{1-3}$ alkylene bridge which is optionally substituted by $R^{14}$;

$R^{14}$ is halo, $C_{1-4}$ alkyl, $C_{1-4}$ haloalkyl, aryl, cycloalkyl, heteroaryl, heterocycloalkyl, CN, $NO_2$, $OR^{a'}$, $SR^{a'}$, $C(O)R^{b'}$, $C(O)NR^{c'}R^{d'}$, $C(O)OR^{a'}$, $OC(O)R^{b'}$, $OC(O)NR^{c'}R^{d'}$, $NR^{c'}R^{d'}$, $NR^{c'}C(O)R^{d'}$, $NR^{c'}C(O)OR^{a'}$, $S(O)R^{b'}$, $S(O)NR^{c'}R^{d'}$, $S(O)_2R^{b'}$, or $S(O)_2NR^{c'}R^{d'}$;

W, W' and W" are each, independently, absent, $C_{1-6}$ alkylenyl, $C_{2-6}$ alkenylenyl, $C_{2-6}$ alkynylenyl, O, S, $NR^e$, CO, COO, $CONR^e$, SO, $SO_2$, $SONR^e$, or $NR^eCONR^f$, wherein said $C_{1-6}$ alkylenyl, $C_{2-6}$ alkenylenyl, $C_{2-6}$ alkynylenyl are each optionally substituted by 1, 2 or 3 halo, OH, $C_{1-4}$ alkoxy, $C_{1-4}$ haloalkoxy, amino, $C_{1-4}$ alkylamino or $C_{2-8}$ dialkylamino;

X, X' and X" are each, independently, absent, $C_{1-6}$ alkylenyl, $C_{2-6}$ alkenylenyl, $C_{2-6}$ alkynylenyl, aryl, cycloalkyl, heteroaryl or heterocycloalkyl, wherein said $C_{1-6}$ alkylenyl, $C_{2-6}$ alkenylenyl, $C_{2-6}$ alkynylenyl, cycloalkyl, heteroaryl or heterocycloalkyl is optionally substituted by one or more halo, CN, $NO_2$, OH, $C_{1-4}$ alkoxy, $C_{1-4}$ haloalkoxy, amino, $C_{1-4}$ alkylamino or $C_{2-8}$ dialkylamino;

Y, Y' and Y" are each, independently, absent, $C_{1-6}$ alkylenyl, $C_{2-6}$ alkenylenyl, $C_{2-6}$ alkynylenyl, O, S, $NR^e$, CO, COO, $CONR^e$, SO, $SO_2$, $SONR^e$, or $NR^eCONR^f$, wherein said $C_{1-6}$ alkylenyl, $C_{2-6}$ alkenylenyl, $C_{2-6}$ alkynylenyl are each optionally substituted by 1, 2 or 3 halo, OH, $C_{1-4}$ alkoxy, $C_{1-4}$ haloalkoxy, amino, $C_{1-4}$ alkylamino or $C_{2-8}$ dialkylamino;

Z, Z' and Z" are each, independently, H, halo, CN, $NO_2$, OH, $C_{1-4}$ alkoxy, $C_{1-4}$ haloalkoxy, amino, $C_{1-4}$ alkylamino, $C_{2-8}$ dialkylamino, $C_{1-6}$ alkyl, $C_{2-6}$ alkenyl, $C_{2-6}$ alkynyl, aryl, cycloalkyl, heteroaryl or heterocycloalkyl, wherein said $C_{1-6}$ alkyl, $C_{2-6}$ alkenyl, $C_{2-6}$ alkynyl, aryl, cycloalkyl, heteroaryl or heterocycloalkyl is optionally substituted by 1, 2 or 3 halo, $C_{1-6}$ alkyl, $C_{2-6}$ alkenyl, $C_{2-6}$ alkynyl, $C_{1-4}$ haloalkyl, aryl, cycloalkyl, heteroaryl, heterocycloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^d$, $NR^cC(O)OR^a$, $S(O)R^b$, $S(O)NR^cR^d$, $S(O)_2R^b$, or $S(O)_2NR^cR^d$;

wherein two —W—X—Y—Z attached to the same atom optionally form a 3-14 membered cycloalkyl or heterocycloalkyl group, each optionally substituted by 1, 2 or 3 —W"—X"—Y"—Z";

wherein two —W'—X'—Y'—Z' attached to the same atom optionally form a 3-14 membered cycloalkyl or heterocycloalkyl group, each optionally substituted by 1, 2 or 3 —W"—X"—Y"—Z";

wherein —W—X—Y—Z is other than H;
wherein —W'—X'—Y'—Z' is other than H;
wherein —W"—X"—Y"—Z" is other than H;

$R^a$ and $R^{a'}$ are each, independently, H, $C_{1-6}$ alkyl, $C_{1-6}$ haloalkyl, $C_{2-6}$ alkenyl, $C_{2-6}$ alkynyl, aryl, cycloalkyl, heteroaryl or heterocycloalkyl, wherein said $C_{1-6}$ alkyl, $C_{1-6}$ haloalkyl, $C_{2-6}$ alkenyl, $C_{2-6}$ alkynyl, aryl, cycloalkyl, heteroaryl or heterocycloalkyl; heterocycloalkyl, heterocycloalkylalkyl is optionally substituted with H, OH, amino, halo, $C_{1-6}$ alkyl, $C_{1-6}$ haloalkyl, aryl, arylalkyl, heteroaryl, heteroarylalkyl, cycloalkyl or heterocycloalkyl;

$R^b$ and $R^{b'}$ are each, independently, H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl, wherein said $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl is optionally substituted with H, OH, amino, halo, $C_{1-6}$ alkyl, $C_{1-6}$ haloalkyl, $C_{1-6}$ haloalkyl, aryl, arylalkyl, heteroaryl, heteroarylalkyl, cycloalkyl or heterocycloalkyl;

$R^c$ and $R^d$ are each, independently, H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with H, OH, amino, halo, $C_{1-6}$ alkyl, $C_{1-6}$ haloalkyl, $C_{1-6}$ haloalkyl, aryl, arylalkyl, heteroaryl, heteroarylalkyl, cycloalkyl or heterocycloalkyl;

or $R^c$ and $R^d$ together with the N atom to which they are attached form a 4-, 5-, 6- or 7-membered heterocycloalkyl group;

$R^{c'}$ and $R^{d'}$ are each, independently, H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with H, OH, amino, halo, $C_{1-6}$ alkyl, $C_{1-6}$ haloalkyl, $C_{1-6}$ haloalkyl, aryl, arylalkyl, heteroaryl, heteroarylalkyl, cycloalkyl or heterocycloalkyl;

or $R^{c'}$ and $R^{d'}$, together with the N atom to which they are attached form a 4-, 5-, 6- or 7-membered heterocycloalkyl group;

$R^e$ and $R^f$ are each, independently, H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with H, OH, amino, halo, $C_{1-6}$ alkyl, $C_{1-6}$ haloalkyl, $C_{1-6}$ haloalkyl, aryl, arylalkyl, heteroaryl, heteroarylalkyl, cycloalkyl or heterocycloalkyl;

or $R^e$ and $R^f$ together with the N atom to which they are attached form a 4-, 5-, 6- or 7-membered heterocycloalkyl group; and $R^g$ is H, $C_{1-6}$ alkyl, aryl, heteroaryl, $C_{3-7}$ cycloalkyl, heterocycloalkyl, arylalkyl, heteroarylalkyl, ($C_{3-7}$ cycloalkyl)alkyl, or heterocycloalkylalkyl.

In some embodiments, when Q is —$(CR^{1a}R^{1b})_m$-A, at least one of $R^{1a}$ and $R^{1b}$ is other than H;

In some embodiments, when Q is unsubstituted $C_{3-8}$ cycloalkyl; adamantyl; 1,2,3,4-tetrahydro-1-naphthanenyl; bicyclo[2.2.1]hept-2-yl; 2-methylcyclohexyl; or 1-ethynyl-cyclohexyl; at least one of $R^3$, $R^4$, $R^5$, $R^6$, $R^7$, $R^8$, $R^9$, $R^{10}$ and $R^{11}$ is other than H.

In some embodiments, when each of $R^3$, $R^4$, $R^5$, $R^6$, $R^7$, $R^8$, $R^9$, $R^{10}$ and $R^{11}$ is H, then Q is other than tetrahydrothienyl, S-oxo-tetrahydrothienyl, S,S-dioxo-tetrahydrothienyl, 2,2,6,6-tetramethyl-4-piperidinyl, N-substituted pyrrolidin-3-yl, N-substituted piperidin-4-yl or 3,4,5,6-tetra-substituted tetrahydropyran-2-yl.

In some embodiments, Cy is aryl or heteroaryl, each optionally substituted with 1, 2, 3, 4 or 5 —W—X—Y—Z.

In some embodiments, Cy is aryl or heteroaryl, each optionally substituted with 1, 2, 3, 4 or 5 —W—X—Y—Z wherein W is O or absent, X is absent, and Y is absent.

In some embodiments, Cy is phenyl, naphthyl, pyridyl, pyrimidinyl, quinolinyl, benzoxazolyl, pyridazinyl, pyrazinyl, triazinyl, furanyl or thienyl, each optionally substituted with 1, 2, 3, 4 or 5 —W—X—Y—Z.

In some embodiments, each —W—X—Y—Z is, independently, halo, nitro, CN, $C_{1-4}$ alkoxy, $C_{1-4}$ haloalkoxy, COOH, C(O)O—$C_{1-4}$ alkyl, CONH—$C_{1-4}$ alkyl, NHC(O)$C_{1-4}$ alkyl, $C_{1-6}$ alkyl, aryl, heteroaryl, cycloalkyl, heterocycloalkyl, aryloxy, heteroaryloxy, cycloalkyloxy, or heterocycloalkyloxy, wherein said $C_{1-6}$ alkyl, aryl, heteroaryl, cycloalkyl, heterocycloalkyl, aryloxy, heteroaryloxy, cycloalkyloxy, or heterocycloalkyloxy is optionally substituted by one or more halo, nitro, CN, $C_{1-4}$ alkoxy, $C_{1-4}$ haloalkoxy, $C_{1-6}$ alkyl, aryl, heteroaryl, cycloalkyl, heterocycloalkyl, aryloxy, heteroaryloxy, cycloalkyloxy, or heterocycloalkyloxy.

In some embodiments, each —W—X—Y—Z is, independently, aryl substituted by aryl, aryl substituted by heteroaryl, heteroaryl substituted by aryl, or heteroaryl substituted by heteroaryl, each optionally substituted by one or more halo, nitro, CN, $C_{1-4}$ alkoxy, $C_{1-4}$ haloalkoxy, $C_{1-4}$ alkyl, $C_{1-4}$ haloalkyl, $C_{1-4}$ hydroxyalkyl, COOH, C(O)O—$C_{1-4}$ alkyl, CONH—$C_{1-4}$ alkyl or NHC(O)$C_{1-4}$ alkyl.

In some embodiments, Cy is phenyl, naphthyl, pyridyl, pyrimidinyl, quinolinyl, benzoxazolyl, pyridazinyl, pyrazinyl, triazinyl, furanyl or thienyl, each optionally substituted with 1, 2, or 3 halo, CN, $C_{1-4}$ alkoxy, $C_{1-4}$ haloalkoxy, $C_{1-6}$ alkyl or aryl, wherein said $C_{1-6}$ alkyl or aryl is optionally substituted by 1, 2 or 3 halo, $C_{1-6}$ alkyl, $C_{1-4}$ haloalkyl, CN, $NO_2$, $OR^a$, or $SR^a$.

In some embodiments, Q is cycloalkyl or heterocycloalkyl, each substituted with 1, 2, 3, 4 or 5 —W'—X'—Y'—Z'.

In some embodiments, each —W'—X'—Y'—Z' is, independently, halo, nitro, CN, $C_{1-4}$ alkoxy, $C_{1-4}$ haloalkoxy, COOH, C(O)O—$C_{1-4}$ alkyl, CONH—$C_{1-4}$ alkyl, NHC(O)$C_{1-4}$ alkyl, $NR^eSO_2(C_{1-4}$ alkyl), $C_{1-6}$ alkyl, aryl, heteroaryl, cycloalkyl, heterocycloalkyl, aryloxy, heteroaryloxy, cycloalkyloxy, or heterocycloalkyloxy, wherein said $C_{1-6}$ alkyl, aryl, heteroaryl, cycloalkyl, heterocycloalkyl, aryloxy, heteroaryloxy, cycloalkyloxy, or heterocycloalkyloxy is optionally substituted by one or more halo, nitro, CN, $C_{1-4}$ alkoxy, $C_{1-4}$ haloalkoxy, $C_{1-6}$ alkyl, aryl, heteroaryl, cycloalkyl, heterocycloalkyl, aryloxy, heteroaryloxy, cycloalkyloxy, or heterocycloalkyloxy.

In some embodiments, Q is cycloalkyl or heterocycloalkyl, each optionally substituted with 1, 2, 3, 4 or 5 OH, $C_{1-4}$ alkoxy, $NR^eCOO(C_{1-4}$ alkyl), $NR^eCO(C_{1-4}$ alkyl), $NR^eSO_2(C_{1-4}$ alkyl), aryl, heteroaryl, —O-aryl, —O-heteroaryl, or —($C_{1-4}$ alkyl)-OH.

In some embodiments, Q is cycloalkyl or heterocycloalkyl, each substituted with at least two —W'—X'—Y'—Z', wherein two of said at least two —W'—X'—Y'—Z' are attached to the same atom and together with the atom to which they are attached form a 3-14 membered cycloalkyl or heterocyloalkyl group, each optionally substituted by 1, 2 or 3 —W"—X"—Y"—Z".

In some embodiments, Q is cycloalkyl or heterocycloalkyl, each substituted with at least two —W'—X'—Y'—Z', wherein two of said at least two —W'—X'—Y'—Z' are attached to the same atom and together with the atom to which they are attached form a 3-14 membered heterocyloalkyl group optionally substituted by 1, 2 or 3 —W"—X"—Y"—Z".

In some embodiments, each —W"—X"—Y"—Z" is, independently, halo, nitro, CN, $C_{1-4}$ alkoxy, $C_{1-4}$ haloalkoxy, COOH, C(O)O—$C_{1-4}$ alkyl, CONH—$C_{1-4}$ alkyl, NHC(O)$C_{1-4}$ alkyl, $NR^eSO_2(C_{1-4}$ alkyl), $C_{1-6}$ alkyl, aryl, heteroaryl, cycloalkyl, heterocycloalkyl, aryloxy, heteroaryloxy, cycloalkyloxy, or heterocycloalkyloxy, wherein said $C_{1-6}$ alkyl, aryl, heteroaryl, cycloalkyl, heterocycloalkyl, aryloxy, heteroaryloxy, cycloalkyloxy, or heterocycloalkyloxy is optionally substituted by one or more halo, nitro, CN, $C_{1-4}$ alkoxy, $C_{1-4}$ haloalkoxy, $C_{1-6}$ alkyl, aryl, heteroaryl, cycloalkyl, heterocycloalkyl, aryloxy, heteroaryloxy, cycloalkyloxy, or heterocycloalkyloxy.

In some embodiments, Q is cyclopropyl, cyclobutyl, cyclopentyl, cyclohexyl, cycloheptyl, indanyl, or 1,2,3,4-tetrahydronaphthalen-2-yl, each optionally substituted with 1, 2, 3, 4 or 5 —W'—X'—Y'—Z'.

In some embodiments, Q is a 3-14 membered heterocycloalkyl group comprising at least one ring-forming O atom, wherein said 3-14 membered heterocycloalkyl group is optionally substituted with 1, 2, 3, 4 or 5 —W'—X'—Y'—Z'.

In some embodiments, Q is cyclohexyl substituted at the 4-position with at least one —W'—X'—Y'—Z'.

In some embodiments, Q is cyclohexyl substituted at the 4-position with at least one OH.

In some embodiments, L is $SO_2$.

In some embodiments, L is absent.

In some embodiments, L is C(O), C(O)O or C(O)$NR^g$.

In some embodiments, L is C(O)$NR^g$ and $R^g$ is H or $C_{1-6}$ alkyl.

In some embodiments, L is C(O)NH.

In some embodiments, $R^N$ is H, $C_{1-6}$ alkyl, $C_{3-7}$ cycloalkyl, or ($C_{3-7}$ cycloalkyl)alkyl.

In some embodiments, $R^N$ is H.

In some embodiments, $R^3$, $R^4$, $R^5$, $R^6$, $R^7$, $R^8$, $R^9$, $R^{10}$ and $R^{11}$ are each, independently, H, OC(O)$R^{a'}$, OC(O)O$R^{b'}$, C(O)O$R^{b'}$, OC(O)N$R^{c'}R^{d'}$, N$R^{c'}$C(O)$R^{a'}$, N$R^{c'}$C(O)O$R^{b'}$, S(O)$R^{a'}$, S(O)N$R^{c'}R^{d'}$, S(O)$_2R^{a'}$, S(O)$_2$N$R^{c'}R^{d'}$, O$R^{b'}$, S$R^{b'}$, $C_{1-10}$ alkyl, $C_{1-10}$ haloalkyl, $C_{2-10}$ alkenyl, $C_{2-10}$ alkynyl, aryl, cycloalkyl, heteroaryl, heterocycloalkyl, arylalkyl, heteroarylalkyl, cycloalkylalkyl or heterocycloalkylalkyl.

In some embodiments, $R^3$, $R^4$, $R^5$, $R^6$, $R^7$, $R^8$, $R^9$, $R^{10}$ and $R^{11}$ are each, independently, H, $C_{1-10}$ alkyl or $C_{1-10}$ haloalkyl.

In some embodiments, $R^3$, $R^4$, $R^5$, $R^6$, $R^7$, $R^8$, $R^9$, $R^{10}$ and $R^{11}$ are each H.

In some embodiments, $R^3$ is $C_{1-10}$ alkyl.

In some embodiments:

$R^4$ and $R^5$ together with the carbon atom to which they are attached form a 3-14 membered cycloalkyl or heterocyloalkyl group which is optionally substituted by $R^{14}$;

or $R^6$ and $R^7$ together with the carbon atom to which they are attached form a 3-14 membered cycloalkyl or heterocyloalkyl group which is optionally substituted by $R^{14}$;

or $R^8$ and $R^9$ together with the carbon atom to which they are attached form a 3-14 membered cycloalkyl or heterocyloalkyl group which is optionally substituted by $R^{14}$;

or $R^{10}$ and $R^{11}$ together with the carbon atom to which they are attached form a 3-14 membered cycloalkyl or heterocyloalkyl group which is optionally substituted by $R^{14}$;

or $R^4$ and $R^6$ together with the carbon atom to which they are attached form a 3-7 membered fused cycloalkyl group or 3-7 membered fused heterocycloalkyl group which is optionally substituted by $R^{14}$;

or $R^6$ and $R^8$ together with the carbon atom to which they are attached form a 3-7 membered fused cycloalkyl group or 3-7 membered fused heterocycloalkyl group which is optionally substituted by $R^{14}$;

or $R^4$ and $R^9$ together form a $C_{1-3}$ alkylene bridge which is optionally substituted by $R^{14}$;

or $R^4$ and $R^{10}$ together form a $C_{1-3}$ alkylene bridge which is optionally substituted by $R^{14}$;

or $R^3$ and $R^7$ together form a $C_{1-3}$ alkylene bridge which is optionally substituted by $R^{14}$;

or $R^3$ and $R^9$ together form a $C_{1-3}$ alkylene bridge which is optionally substituted by $R^{14}$;

or $R^6$ and $R^{10}$ together form a $C_{1-3}$ alkylene bridge which is optionally substituted by $R^{14}$;

or $R^9$ and $R^{10}$ together form a $C_{1-3}$ alkylene bridge which is optionally substituted by $R^{14}$.

At various places in the present specification, substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

The term "n-membered" where n is an integer typically describes the number of ring-forming atoms in a moiety where the number of ring-forming atoms is n. For example, piperidinyl is an example of a 6-membered heterocycloalkyl ring and 1,2,3,4-tetrahydro-naphthalene is an example of a 10-membered cycloalkyl group.

As used herein, the term "substituted" or "substitution" is meant to refer to the replacing of a hydrogen atom with a substituent other than H. For example, an "N-substituted piperidin-4-yl" refers to replacement of the H atom from the NH of the piperidinyl with a non-hydrogen sustituent such as, for example, alkyl.

As used herein, the term "alkyl" is meant to refer to a saturated hydrocarbon group which is straight-chained or branched. Example alkyl groups include methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like. An alkyl group can contain from 1 to about 20, from 2 to about 20, from 1 to about 10, from 1 to about 8, from 1 to about 6, from 1 to about 4, or from 1 to about 3 carbon atoms. The term "alkylenyl" or "alkylene bridge" refers to a divalent alkyl linking or bridging group.

As used herein, "alkenyl" refers to an alkyl group having one or more double carbon-carbon bonds. Example alkenyl groups include ethenyl, propenyl, and the like. The term "alkenylenyl" refers to a divalent linking alkenyl group.

As used herein, "alkynyl" refers to an alkyl group having one or more triple carbon-carbon bonds. Example alkynyl groups include ethynyl, propynyl, and the like. The term "alkynylenyl" refers to a divalent linking alkynyl group.

As used herein, "haloalkyl" refers to an alkyl group having one or more halogen substituents. Example haloalkyl groups include $CF_3$, $C_2F_5$, $CHF_2$, $CCl_3$, $CHCl_2$, $C_2Cl_5$, and the like.

As used herein, "aryl" refers to monocyclic or polycyclic (e.g., having 2, 3 or 4 fused rings) aromatic hydrocarbons such as, for example, phenyl, naphthyl, anthracenyl, phenanthrenyl, indanyl, indenyl, and the like. In some embodiments, aryl groups have from 6 to about 20 carbon atoms.

As used herein, "cycloalkyl" refers to non-aromatic cyclic hydrocarbons including cyclized alkyl, alkenyl, and alkynyl groups. Cycloalkyl groups can include mono- or polycyclic (e.g., having 2, 3 or 4 fused rings) ring systems as well as spiro ring systems. Ring-forming carbon atoms of a cycloalkyl group can be optionally substituted by oxo or sulfido. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, adamantyl, and the like. Also included in the definition of cycloalkyl are moieties that have one or more aromatic rings fused (i.e., having a bond in common with) to the cycloalkyl ring, for example, benzo or thienyl derivatives of pentane, pentene, hexane, and the like.

As used herein, "heteroaryl" groups refer to an aromatic heterocycle having at least one heteroatom ring member such as sulfur, oxygen, or nitrogen. Heteroaryl groups include monocyclic and polycyclic (e.g., having 2, 3 or 4 fused rings) systems. Examples of heteroaryl groups include without limitation, pyridyl, pyrimidinyl, pyrazinyl, pyridazinyl, triazinyl, furyl, quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, and the like. In some embodiments, the heteroaryl group has from 1 to about 20 carbon atoms, and in further embodiments from about 3 to about 20 carbon atoms. In some embodiments, the heteroaryl group contains 3 to about 14, 3 to about 7, or 5 to 6 ring-forming atoms. In some embodiments, the heteroaryl group has 1 to about 4, 1 to about 3, or 1 to 2 heteroatoms.

As used herein, "heterocycloalkyl" refers to non-aromatic heterocycles including cyclized alkyl, alkenyl, and alkynyl groups where one or more of the ring-forming carbon atoms is replaced by a heteroatom such as an O, N, or S atom. Heterocycloalkyl groups can be mono- or polycyclic (e.g., having 2, 3, 4 or more fused rings or having a 2-ring, 3-ring, 4-ring spiro system (e.g., having 8 to 20 ring-forming atoms)). Heterocycloalkyl groups include monocyclic and polycyclic groups. Example "heterocycloalkyl" groups include morpholino, thiomorpholino, piperazinyl, tetrahydrofuranyl, tetrahydrothienyl, 2,3-dihydrobenzofuryl, 1,3-benzodioxole, benzo-1,4-dioxane, piperidinyl, pyrrolidinyl, isoxazolidinyl, isothiazolidinyl, pyrazolidinyl, oxazolidinyl, thiazolidinyl, imidazolidinyl, and the like. Ring-forming carbon atoms and heteroatoms of a heterocycloalkyl group can be optionally substituted by oxo or sulfido. Also included in the definition of heterocycloalkyl are moieties that have one or more aromatic rings fused (i.e., having a bond in common with) to the nonaromatic heterocyclic ring, for example phthalimidyl, naphthalimidyl, and benzo derivatives of heterocycles such as indolene and isoindolene groups. In some embodiments, the heterocycloalkyl group has from 1 to about 20 carbon atoms, and in further embodiments from about 3 to about 20 carbon atoms. In some embodiments, the heterocycloalkyl group contains 3 to about 14, 3 to about 7, or 5 to 6 ring-forming atoms. In some embodiments, the heterocycloalkyl group has 1 to about 4, 1 to about 3, or 1 to 2 heteroatoms. In some embodiments, the heterocycloalkyl group contains 0 to 3 double bonds. In some embodiments, the heterocycloalkyl group contains 0 to 2 triple bonds.

As used herein, "halo" or "halogen" includes fluoro, chloro, bromo, and iodo.

As used herein, "alkoxy" refers to an —O-alkyl group. Example alkoxy groups include methoxy, ethoxy, propoxy (e.g., n-propoxy and isopropoxy), t-butoxy, and the like.

As used here, "haloalkoxy" refers to an —O-haloalkyl group. An example haloalkoxy group is $OCF_3$.

As used herein, "aryloxy" refers to —O-aryl.

As used herein, "heteroaryloxy" refers to —O-heteroaryl.

As used herein, "cycloalkyloxy" refers to —O-cycloalkyl.

As used herein, "heterocycloalkyloxy" refers to —O-heterocycloalkyl.

As used herein, "arylalkyl" refers to alkyl substituted by aryl and "cycloalkylalkyl" refers to alkyl substituted by cycloalkyl. An example arylalkyl group is benzyl.

As used herein, "amino" refers to $NH_2$.

As used herein, "alkylamino" refers to an amino group substituted by an alkyl group.

As used herein, "dialkylamino" refers to an amino group substituted by two alkyl groups.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically active starting materials are known in the art, such as by resolution of racemic mixtures or by stereoselective synthesis. Many geometric isomers of olefins, C═N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms.

Resolution of racemic mixtures of compounds can be carried out by any of numerous methods known in the art. An example method includes fractional recrystallizaion using a "chiral resolving acid" which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds of the invention also include tautomeric forms, such as keto-enol tautomers.

Compounds of the invention can also include all isotopes of atoms occurring in the intermediates or final compounds. Isotopes include those atoms having the same atomic number but different mass numbers. For example, isotopes of hydrogen include tritium and deuterium.

The phrase "pharmaceutically acceptable" is employed herein to refer to those compounds, materials, compositions, and/or dosage forms which are, within the scope of sound medical judgement, suitable for use in contact with the tissues of human beings and animals without excessive toxicity, irritation, allergic response, or other problem or complication, commensurate with a reasonable benefit/risk ratio.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts or the quaternary ammonium salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418 and *Journal of Pharmaceutical Science,* 66, 2 (1977), each of which is incorporated herein by reference in its entirety.

The present invention also includes prodrugs of the compounds described herein. As used herein, "prodrugs" refer to any covalently bonded carriers which release the active parent drug when administered to a mammalian subject. Prodrugs can be prepared by modifying functional groups present in the compounds in such a way that the modifications are cleaved, either in routine manipulation or in vivo, to the parent compounds. Prodrugs include compounds wherein hydroxyl, amino, sulfhydryl, or carboxyl groups are bonded to any group that, when administered to a mammalian subject, cleaves to form a free hydroxyl, amino, sulfhydryl, or carboxyl group respectively. Examples of prodrugs include, but are not limited to, acetate, formate and benzoate derivatives of alcohol and amine functional groups in the compounds of the invention. Preparation and use of prodrugs is discussed in T.

Higuchi and V. Stella, "Pro-drugs as Novel Delivery Systems," Vol. 14 of the A.C.S. Symposium Series, and in *Bioreversible Carriers in Drug Design*, ed. Edward B. Roche, American Pharmaceutical Association and Pergamon Press, 1987, both of which are hereby incorporated by reference in their entirety.

Synthesis

The novel compounds of the present invention can be prepared in a variety of ways known to one skilled in the art of organic synthesis. The compounds of the present invention can be synthesized using the methods as hereinafter described below, together with synthetic methods known in the art of synthetic organic chemistry or variations thereon as appreciated by those skilled in the art.

The compounds of this invention can be prepared from readily available starting materials using the following general methods and procedures. It will be appreciated that where typical or preferred process conditions (i.e., reaction temperatures, times, mole ratios of reactants, solvents, pressures, etc.) are given; other process conditions can also be used unless otherwise stated. Optimum reaction conditions may vary with the particular reactants or solvent used, but such conditions can be determined by one skilled in the art by routine optimization procedures.

The processes described herein can be monitored according to any suitable method known in the art. For example, product formation can be monitored by spectroscopic means, such as nuclear magnetic resonance spectroscopy (e.g., $^1$H or $^{13}$C) infrared spectroscopy, spectrophotometry (e.g., UV-visible), or mass spectrometry, or by chromatography such as high performance liquid chromatograpy (HPLC) or thin layer chromatography.

Preparation of compounds can involve the protection and deprotection of various chemical groups. The need for protection and deprotection, and the selection of appropriate protecting groups can be readily determined by one skilled in the art. The chemistry of protecting groups can be found, for example, in Greene, et al., *Protective Groups in Organic Synthesis*, 2d. Ed., Wiley & Sons, 1991, which is incorporated herein by reference in its entirety.

The reactions of the processes described herein can be carried out in suitable solvents which can be readily selected by one of skill in the art of organic synthesis. Suitable solvents can be substantially nonreactive with the starting materials (reactants), the intermediates, or products at the temperatures at which the reactions are carried out, i.e., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected.

The compounds of the invention can be prepared, for example, using the reaction pathways and techniques as described below.

A series of piperidine-3-carboxamides of formula 4 are prepared by the method outlined in Scheme 1. 1-(tert-Butoxycarbonyl)piperidine-3-carboxylic acid 1 is coupled to an amine R$^N$QNH (wherein Q can be cycloalkyl, heterocycloalkyl, arylalky, heteroarylalky or the like, and R$^N$ can be a variety of substituents, such as H, (C$_{3-7}$ cycloalkyl)alkyl or the like), using coupling reagents such as BOP to provide the desired product 2. The Boc protecting group of 2 is removed by TFA in methylene chloride to afford the amino salt 3, which is directly coupled with a variety of acyl halides CyC(O)Cl, chloroformates CyOC(O)Cl, or sulfonyl chlorides CySO$_2$Cl wherein Cy is a cyclic moiety such as aryl to give the final compounds with formula 4. A series of ureas of general formula 4' can be prepared by treating the piperidine derivative 3 with a corresponding isocyante Cy(R$^g$)N═C═O or a corresponding amine carbonyl chloride Cy(R$^g$)NHC(O)Cl in the presence of a base. Alternatively, a series of ureas of general formula 4' can be prepared by treating the piperidine derivative 3 with p-nitrophenyl chloroformate in the presence of base to form the activated carbamate species 3' that is subsequently reacted with a suitable amine R$^g$NHCy.

Scheme 1

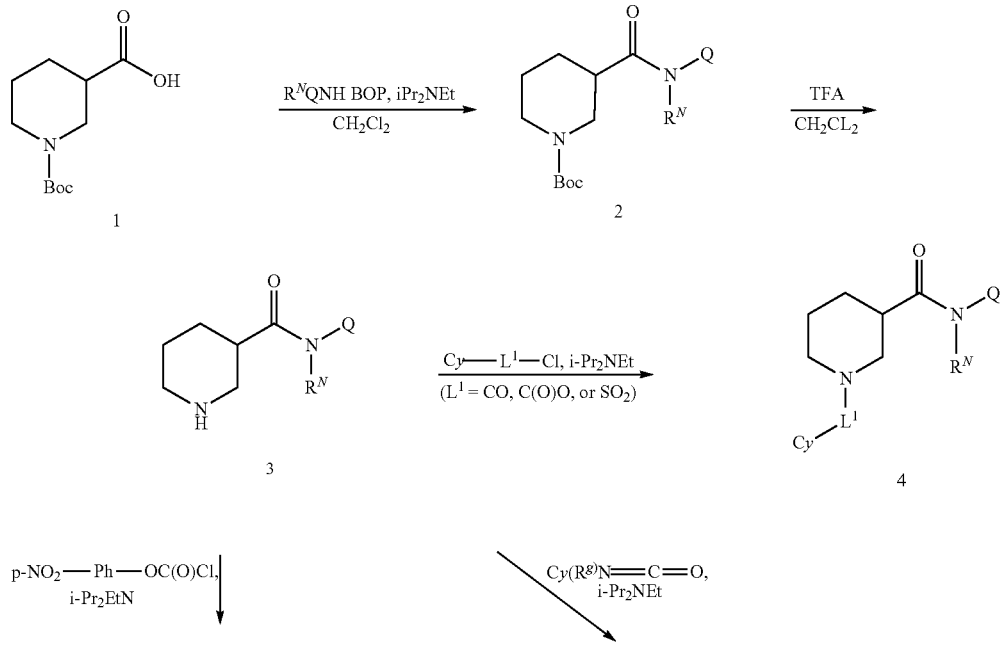

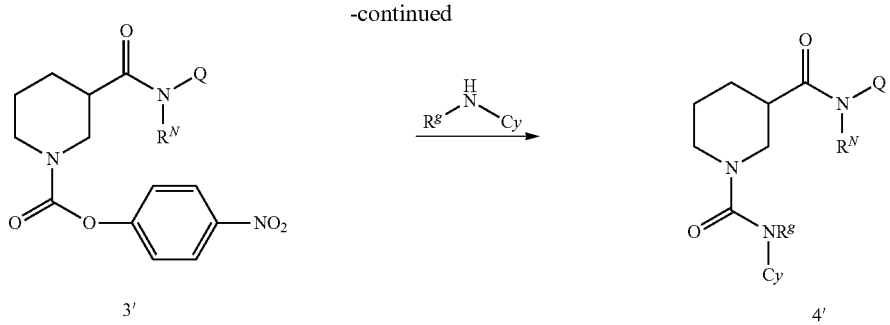

A series of piperidine-3-carboxamides of formula 5 are prepared by the method outlined in Scheme 2. Ethyl piperidine-3-carboxylate 6 is treated with $(Boc)_2O$ to give Boc-protected compound 7. Compound 7 is then treated with LiHMDS, followed by alkylation with organo halides $R^3X$ (X is halo, $R^3$ can be $C_{1-10}$ alkyl, $C_{2-10}$ alkenyl, $C_{2-10}$ alkynyl, cycloalkyl, heterocycloalkyl, arylalkyl or the like) to afford the coupling product 8. The ethyl ester of 8 is directly converted to the corresponding amides 9. (wherein Q can be cycloalkyl, heterocycloalkyl, arylalky, heteroarylalky or the like, and $R^N$ can be a variety of substituents, such as H, $(C_{3-7}$ cycloalkyl)alkyl or the like) The Boc group of compound 9 is removed by TFA to afford the TFA salt 10, which can be coupled with a variety of acyl halides CyC(O)Cl, chloroformates CyOC(O)Cl, or sulfonyl chlorides $CySO_2Cl$ wherein Cy is a cyclic moiety such as aryl to afford the desired coupling products 5. A series of ureas of general formula 5' can be prepared by treating the piperidine derivative 10 with a corresponding isocyante $Cy(R^g)N=C=O$ or a corresponding amine carbonyl chloride $Cy(R^g)NHC(O)Cl$ in the presence of a base. Alternatively, a series of ureas of general formula 5' can be prepared by treating the piperidine derivative 10 with p-nitrophenyl chloroformate in the presence of base to form the activated carbamate species 10' that is subsequently reacted with a suitable amine $R^gNHCy$.

Scheme 2

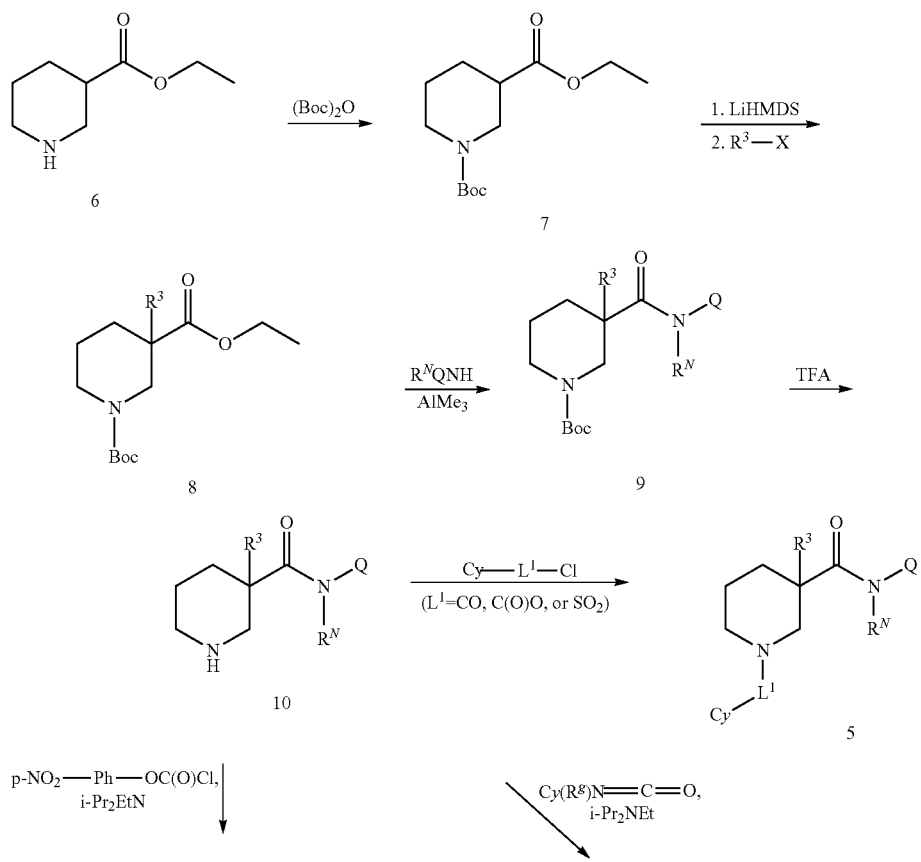

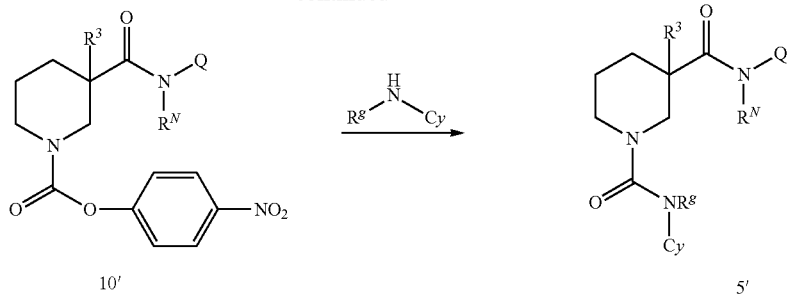

Primary amines of formula II can be prepared from an appropriate cyclic ketone 12 under a variety of protocols one of which is shown in Scheme 3 (wherein $R^x$ is, e.g., H, halo, alkyl, haloalkyl, cycloalkyl, aryl, heteroaryl, etc.; X is $CH_2$, O, S, $SO_2$, NH, N-alkyl, N-Boc, etc.; p is 1 or 2; and n is 1 or 2).

Scheme 3

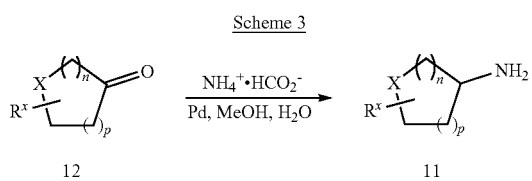

Alternatively, primary amines 11 can be prepared from the appropriate alcohols 13 via mesylation, followed by conversion of the mesylates 14 to the corresponding azides 15, which upon reduction yield the desired primary amines 11, as shown in Scheme 4 ($R^x$, X, n and p are as defined in Scheme 3).

Scheme 4

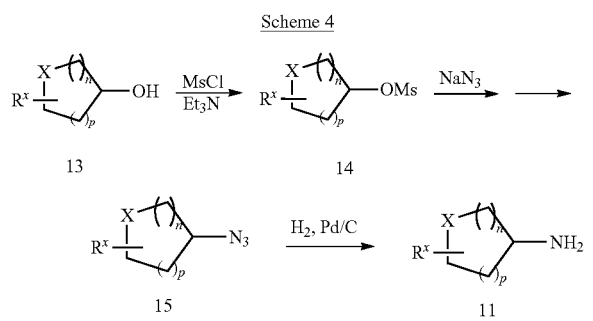

Secondary amines of formula 16 can be prepared from the reaction of an appropriate cyclic amine 11 with a suitable aldehyde $R^1CHO$ (wherein $R^1$ can be H, $C_{1-10}$ alkyl, $C_{2-10}$ alkenyl, aryl, heteroaryl, arylalkyl or the like) as shown in Scheme 5 ($R^x$, X, n and p are as defined in Scheme 3).

Scheme 5

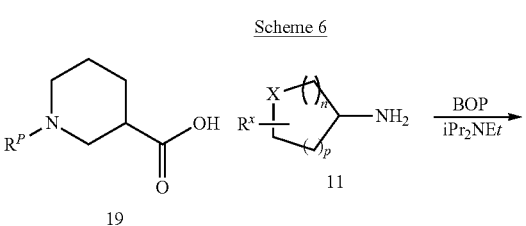

Carboxamides of formula 18 can be prepared as shown in Scheme 6 (X, $R^x$, n and p are as defined in Scheme 3; and $R^P$ is H or an amino protecting group) using BOP or any other suitable coupling agent.

Scheme 6

Primary amines of formula 23 and secondary amines of formula 20 can be prepared according to the method outlined in Scheme 7. A suitable bromide such as 21 (A can be alkyl, cycloalkyl, heterocycloalkyl, aryl, heteroaryl, arylalkyl, heteroarylalkyl or the like, $R^2$ can be alkyl, haloalkyl, cycloalkyl, cycloalkylalyl, etc.) can be converted to the corresponding azide 22 first and then to the desired primary amine 23 via hydrogenation. Finally, reductive amination of an appropriate aldehyde $R^1CHO$ (wherein $R^1$ can be H, $C_{1-40}$ alkyl, $C_{2-10}$ alkenyl, aryl, heteroaryl, arylalkyl or the like) yields secondary amines of formula 20.

Scheme 7

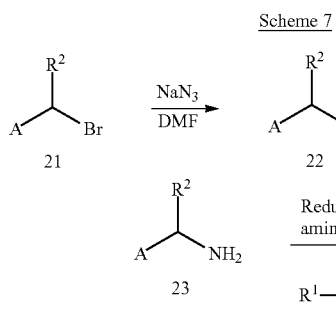

Primary amines 24 and secondary amines 25 can be prepared according to the method outlined in Scheme 8 ($R^{iii}$ and $R^{iv}$ are, e.g., halo, alkyl, haloalkyl, OH, alkoxy, aryl, heteroaryl, etc.). Reaction of a substituted indole 26 with an Fmoc protected amino acid chloride 27 (wherein $R^{vi}$ is, e.g., H, halo, alkyl, haloalkyl, OH, alkoxy, aryl, heteroaryl, etc.) provides 28, following cleavage of the Fmoc group with piperidine in DMF. Reduction of the carbonyl group of 28 with $NaBH_4$ gives 24 which upon treatment with the appropriate aldehyde $R^1CHO$ (wherein $R^1$ can be H, $C_{1-10}$ alkyl, $C_{2-10}$ alkenyl, aryl, heteroaryl, arylalkyl or the like) under reductive amination conditions provides 25.

Scheme 8

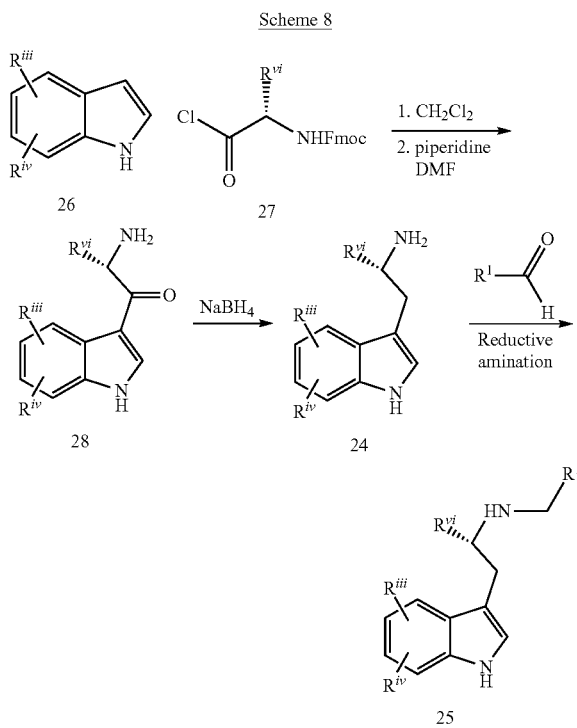

A series of piperidine-3-carboxamides of formula 29 are prepared by the method outlined in Scheme 9. A piperidine-3-carboxamide 10 is coupled to a compound having the formula of ArX (wherein X can be a leaving group such as halo, and wherein Ar can be a cyclic moiety such as aryl or heteroaryl, and can be optionally substituted by one or more suitable substituents such as alkyl, alkoxy or the like), such as bromobenzene, in a solvent such as dimethyl sulfoxide in the presence of a base such as tert-butoxide to afford a compound of formula 29. Alternatively, the coupling reaction is conducted under palladium catalyzed conditions, such as Hartwig's conditions.

Scheme 9

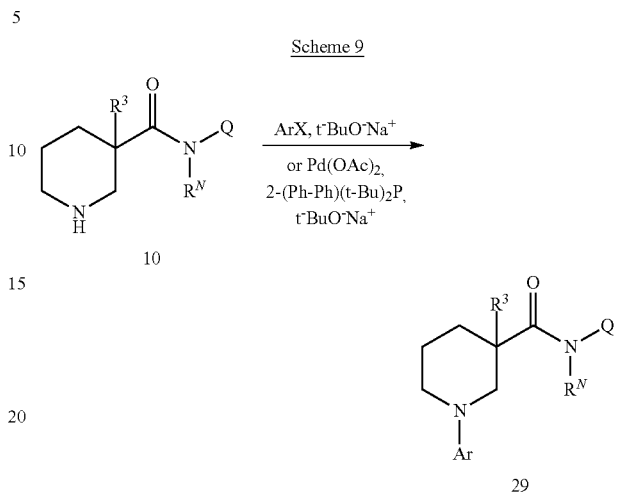

Methods

Compounds of the invention can modulate activity of 11βHSD1 and/or MR. The term "modulate" is meant to refer to an ability to increase or decrease activity of an enzyme or receptor. Accordingly, compounds of the invention can be used in methods of modulating 11βHSD1 and/or MR by contacting the enzyme or receptor with any one or more of the compounds or compositions described herein. In some embodiments, compounds of the present invention can act as inhibitors of 11βHSD1 and/or MR. In further embodiments, the compounds of the invention can be used to modulate activity of 11βHSD1 and/or MR in an individual in need of modulation of the enzyme or receptor by administering a modulating amount of a compound of the invention.

The present invention further provides methods of inhibiting the conversion of cortisone to cortisol in a cell, or inhibiting the production of cortisol in a cell, where conversion to or production of cortisol is mediated, at least in part, by 11βHSD1 activity. Methods of measuring conversion rates of cortisone to cortisol and vice versa, as well as methods for measuring levels of cortisone and cortisol in cells, are routine in the art.

The present invention further provides methods of increasing insulin sensitivity of a cell by contacting the cell with a compound of the invention. Methods of measuring insulin sensitivity are routine in the art.

The present invention further provides methods of treating diseases associated with activity or expression, including abnormal activity and overexpression, of 11βHSD1 and/or MR in an individual (e.g., patient) by administering to the individual in need of such treatment a therapeutically effective amount or dose of a compound of the present invention or a pharmaceutical composition thereof. Example diseases can include any disease, disorder or condition that is directly or indirectly linked to expression or activity of the enzyme or receptor. An 11βHSD1-associated disease can also include any disease, disorder or condition that can be prevented, ameliorated, or cured by modulating the enzyme activity. An MR-associated disease can also include any disease, disorder or condition that can be prevented, ameliorated, or cured by modulating the receptor activity or binding to the receptor of endogenous ligands.

Examples of 11βHSD1-associated diseases include obesity, diabetes, glucose intolerance, insulin resistance, hyperglycemia, hypertension, hyperlipidemia, cognitive impairment, dementia, depression, glaucoma, cardiovascular disorders, osteoporosis, and inflammation. Further examples of 11βHSD1-associated diseases include metabolic syndrome, type 2 diabetes, androgen excess (hirsutism, menstrual irregularity, hyperandrogenism) and polycystic ovary syndrome (PCOS).

The present invention further provides methods of modulating MR activity by contacting the MR with a compound of the invention, pharmaceutically acceptable salt, prodrug, or composition thereof. In some embodiments, the modulation can be inhibition. In further embodiments, methods of inhibiting aldosterone binding to the MR (optionally in a cell) are provided. Methods of measuring MR activity and measuring inhibition of aldosterone binding are routine in the art.

The present invention further provides methods of treating a disease associated with activity or expression of the MR. Examples of diseases associated with activity or expression of the MR include, but are not limited to hypertension, as well as cardiovascular, renal, and inflammatory pathologies such as heart failure, atherosclerosis, arteriosclerosis, coronary artery disease, thrombosis, angina, peripheral vascular disease, vascular wall damage, stroke, dyslipidemia, hyperlipoproteinaemia, diabetic dyslipidemia, mixed dyslipidemia, hypercholesterolemia, hypertriglyceridemia, and those associated with type 1 diabetes, type 2 diabetes, obesity metabolic syndrome, insulin resistance and general aldosterone-related target organ damage.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal. In some embodiments, the cell is an adipocyte, a pancreatic cell, a hepatocyte, neuron, or cell comprising the eye.

As used herein, the term "contacting" refers to the bringing together of indicated moieties in an in vitro system or an in vivo system. For example, "contacting" the 11βHSD1 enzyme with a compound of the invention includes the administration of a compound of the present invention to an individual or patient, such as a human, having 11βHSD1, as well as, for example, introducing a compound of the invention into a sample containing a cellular or purified preparation containing the 11βHSD1 enzyme.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician, which includes one or more of the following:

(1) preventing the disease; for example, preventing a disease, condition or disorder in an individual who may be predisposed to the disease, condition or disorder but does not yet experience or display the pathology or symptomatology of the disease (non-limiting examples are preventing metabolic syndrome, hypertension, obesity, insulin resistance, hyperglycemia, hyperlipidemia, type 2 diabetes, androgen excess (hirsutism, menstrual irregularity, hyperandrogenism) and polycystic ovary syndrome (PCOS);

(2) inhibiting the disease; for example, inhibiting a disease, condition or disorder in an individual who is experiencing or displaying the pathology or symptomatology of the disease, condition or disorder (i.e., arresting further development of the pathology and/or symptomatology) such as inhibiting the development of metabolic syndrome, hypertension, obesity, insulin resistance, hyperglycemia, hyperlipidemia, type 2 diabetes, androgen excess (hirsutism, menstrual irregularity, hyperandrogenism) or polycystic ovary syndrome (PCOS), stabilizing viral load in the case of a viral infection; and (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of metabolic syndrome, hypertension, obesity, insulin resistance, hyperglycemia, hyperlipidemia, type 2 diabetes, androgen excess (hirsutism, menstrual irregularity, hyperandrogenism) and polycystic ovary syndrome (PCOS), or lowering viral load in the case of a viral infection.

Pharmaceutical Formulations and Dosage Forms

When employed as pharmaceuticals, the compounds of Formula I can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), ocular, oral or parenteral. Methods for ocular delivery can include topical administration (eye drops), subconjunctival, periocular or intravitreal injection or introduction by balloon catheter or ophthalmic inserts surgically placed in the conjunctival sac. Parenteral administration includes intravenous, intraarterial, subcutaneous, intraperitoneal or intramuscular injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, one or more of the compounds of the invention above in combination with one or more pharmaceutically acceptable carriers. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compounds of the invention can also be formulated in combination with one or more additional active ingredients which can include any pharmaceutical agent such as antiviral agents, antibodies, immune suppressants, anti-inflammatory agents and the like. Example agents that can be coadministered (e.g., simultaneously, separately, or sequentially) include insulin and insulin analogs; insulin secretagogues including sulphonylureas (e.g., glibenclamide or glipizide), prandial glucose regulators (e.g., repaglinide or nateglinide), glucagons-like peptide 1 agonist (GLP1 agonist) (e.g., exenatide or liraglutide) and dipeptidylpeptidase IV inhibitors (DPP-IV inhibitors); insulin sensitizing agents including PPARγ agonists (e.g., pioglitazone or rosiglitazone); agents that suppress hepatic glucose output (e.g., metformin); agents designed to reduce the absorption of glucose from the intestine (e.g., acarbose); agents designed to treat the complications of prolonged hyperglycemia (e.g., aldose reducatase inhibitors); anti-diabetic agents including phosphotyrosine phosphatase inhibitors, glucose 6-phosphatase inhibitors, glucagons receptor antagonists, glucokinase activators, glycogen phosphorylase inhibitors, fructose 1,6-bisphosphatase inhibitors, glutamine:fructose-6-phosphate amidotransferase inhibitors; anti-obesity agents (e.g., sibutramine or orlistat); anti-dyslipidemia agents including HMG-CoA reductase inhibitors (e.g., statins like pravastatin), PPARα agonists (e.g., fibrates like gemfibrozil), bile acid sequestrants (e.g., chloestyramine), cholesterol absorption inhibitors (e.g., plant stanols or synthetic inhibitors), ileal bile acid absorption inhibitors (IBATi), cholesterol ester transfer protein inhibitors, nicotinic acid and analogues thereof (e.g., niacin); antihypertensive agents including β blockers (e.g., atenolol or inderal), ACE inhibitors (e.g., lisinopril), calcium antagonists (e.g., nifedipine), angiotensin receptor antagonists (e.g., candesartan), a antagonists, diuretic agents (e.g., furosemide or benzthiazide); hemostasis modulators including antithrombotics, activators of fibrinolysis, thrombin antagonists, faxtor Xa inhibitors, factor VIIa inhibitors, anti-platelet agents (e.g., aspirin or clopidogrel), anticoagulants (e.g., heparin, hirudin, analogs thereof), and warfarin; and anti-inflammatory agents including non-steroidal anti-inflammatory drugs (e.g., aspirin) and steroidal anti-inflammatory drugs (e.g., cortisone).

Labeled Compounds and Assay Methods

Another aspect of the present invention relates to radio-labeled compounds of the invention that would be useful not only in radio-imaging but also in assays, both in vitro and in vivo, for localizing and quantitating the enzyme in tissue samples, including human, and for identifying ligands by inhibition binding of a radio-labeled compound. Accordingly, the present invention includes enzyme assays that contain such radio-labeled compounds.

The present invention further includes isotopically-labeled compounds of the invention. An "isotopically" or "radio-labeled" compound is a compound of the invention where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^{2}H$ (also written as D for deuterium), $^{3}H$ (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$ and $^{131}I$. The radionuclide that is incorporated in the instant radio-labeled compounds will depend on the specific application of that radio-labeled compound. For example, for in vitro receptor labeling and competition assays, compounds that incorporate $^{3}H$, $^{14}C$, $^{82}Br$, $^{125}I$, $^{35}S$ or will generally be most useful. For radio-imaging applications $^{11}C$, $^{18}F$, $^{125}I$, $^{123}I$, $^{124}I$, $^{131}I$, $^{75}Br$, $^{76}Br$ or $^{77}Br$ will generally be most useful.

It is understood that a "radio-labeled" or "labeled compound" is a compound that has incorporated at least one radionuclide. In some embodiments the radionuclide is selected from the group consisting of $^{3}H$, $^{14}C$, $^{125}I$, $^{35}S$ and $^{82}Br$.

Synthetic methods for incorporating radio-isotopes into organic compounds are applicable to compounds of the invention and are well known in the art.

A radio-labeled compound of the invention can be used in a screening assay to identify/evaluate compounds. In general terms, a newly synthesized or identified compound (i.e., test compound) can be evaluated for its ability to reduce binding of the radio-labeled compound of the invention to the enzyme. Accordingly, the ability of a test compound to compete with the radio-labeled compound for binding to the enzyme directly correlates to its binding affinity.

Kits

The present invention also includes pharmaceutical kits useful, for example, in the treatment or prevention of 11βHSD1-associated diseases or disorders, obesity, diabetes and other diseases referred to herein which include one or more containers containing a pharmaceutical composition comprising a therapeutically effective amount of a compound of the invention. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results. The compounds of the example section were found to be inhibitors or antagonists of 11βHSD1 or MR according to one or more of the assays provided herein.

EXAMPLES

Example 1

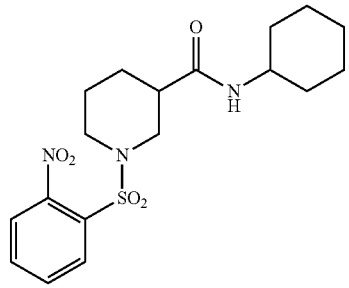

N-Cyclohexyl-1-[(2-nitrophenyl)sulfonyl]piperidine-3-carboxamide

Step 1.

To a solution of 1-(tert-butoxycarbonyl)piperidine-3-carboxylic acid (69 mg, 0.3 mmol), cyclohexanamine (30 mg, 0.3) and BOP (140 mg) in 1.0 mL methylene chloride was added 68.5 μL of N,N-diisopropylethylamine. The reaction mixture was stirred at room temperature for overnight and directly purified with Combi-Flash, eluted with EtOAc/Hexane to afford 70 mg of the desired product.

Step 2.

To a solution of tert-butyl 3-(cyclohexylcarbamoyl)piperidine-1-carboxylate (70 mg) in 4.5 mL methylene chloride and 0.5 mL water was added 5 mL TFA. The reaction mixture was stirred at room temperature for 50 min, and then concentrated under reduced pressure to give a residue.

Step 3.

To a solution of 2-nitrobenzene-1-sulfonyl chloride (12.3 mg) and N-cyclohexylpiperidine-3-carboxamide (TFA salt, 18 mg) from Step 2 in 0.2 mL acetonitrile was added triethylamine (19.3 μL). The reaction mixture was stirred at RT for 2 hours and directly purified by HPLC to give 13.2 mg of desired product. LCMS: m/z 396.1 (M+H)+; 813.3 (2M+Na)+.

Example 2

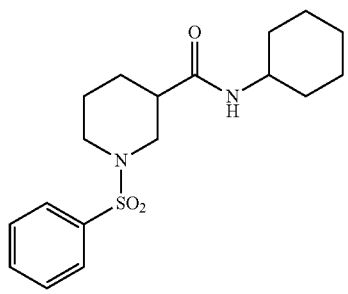

N-Cyclohexyl-1-(phenylsulfonyl)piperidine-3-carboxamide

This compound was prepared using procedures analogous to those described in example 1. LCMS: m/z 351.1 (M+H)+; 373.0 (M+Na)+; 723.2 (2M+Na)+.

Example 3

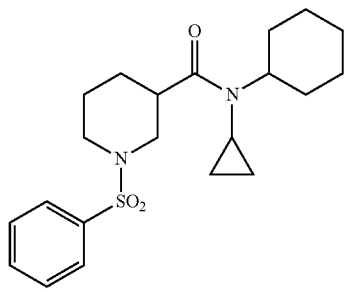

N-Cyclohexyl-N-cyclopropyl-1-(phenylsulfonyl)piperidine-3-carboxamide

Step 1.

To a solution of benzyl piperidine-3-carboxylate (TFA salt, 1.5 g) and potassium carbonate (2.2 g) in 10 mL acetonitrile was added 0.409 mL benzenesulfonyl chloride. The reaction mixture was stirred at rt for 2 hours. The reaction mixture was diluted with ethyl acetate and washed with water, brine and dried over $Na_2SO_4$. After filtration, the filtrate was concentrated to give a residue.

Step 2.

The residue from Step 1 was hydrogenated using Pd/C as the catalyst.

Step 3.

To a solution of 1-(phenylsulfonyl)piperidine-3-carboxylic acid (20 mg), N-cyclopropylcyclohexanamine (10 mg) and benzotriazol-1-yloxytris(dimethylamino)-phosphonium hexafluorophosphate (36 mg) in DMF (200 μL) was added N,N-diisopropylethylamine (26 μL). The resulting solution was stirred at r.t. for 2 hours and directly purified with prep HPLC. LCMS m/z 391.1 (M+H)+; 803.2 (2M+Na)+.

Example 4

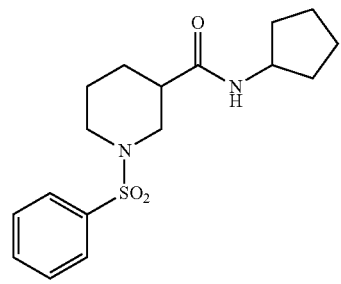

N-Cyclopentyl-1-(phenylsulfonyl)piperidine-3-carboxamide

This compound was prepared using procedures analogous to those described in example 1. LCMS: m/z 337.1 (M+H)+; 359.0 (M+Na)+; 695.2 (2M+Na)+.

Example 5

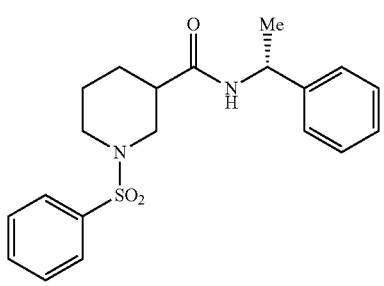

33

N-[(1R)-1-Phenylethyl]-1-(phenylsulfonyl)piperidine-3-carboxamide

This compound was prepared using the procedures analogous to those described in example 1. LCMS: m/z 373.1 (M+H)+; 395.0 (M+Na)+; 767.5 (2M+Na)+.

Example 6

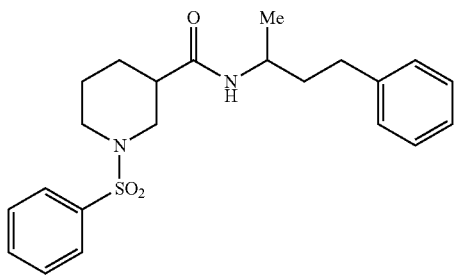

N-(1-Methyl-3-phenylpropyl)-1-(phenylsulfonyl)piperidine-3-carboxamide

This compound was prepared using procedures analogous to those described in example 1. LCMS: m/z 401.0 (M+H)+; 423.1 (M+Na)+.

Example 7

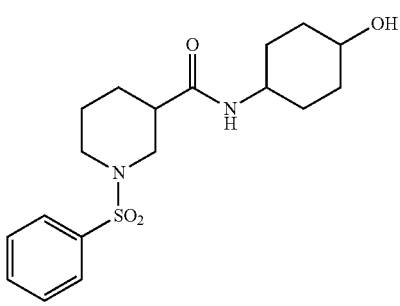

34

N-(4-Hydroxycyclohexyl)-1-(phenylsulfonyl)piperidine-3-carboxamide

This compound was prepared using procedures analogous to those described in example 1. LCMS: m/z 367.0 (M+H)+; 755.0 (2M+Na)+.

Example 8

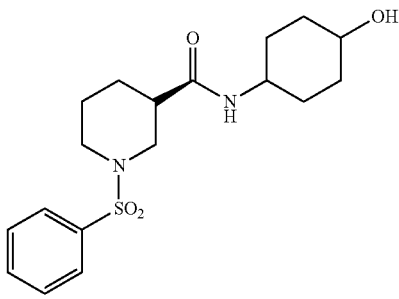

(3R)—N-(4-Hydroxycyclohexyl)-1-(phenylsulfonyl)piperidine-3-carboxamide

This compound was prepared using procedures analogous to those described in example 1. LCMS: m/z 367.1 (M+H)+; 755.2 (M+Na)+.

Example 9

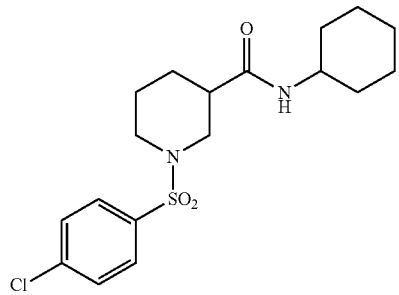

1-[(4-Chlorophenyl)sulfonyl]-N-cyclohexylpiperidine-3-carboxamide

This compound was prepared procedures analogous to those described in example 1. LCMS: 385.1 (M+H)+; 387.1 (M+Na)+; 791.2 (2M+Na)+

Example 10

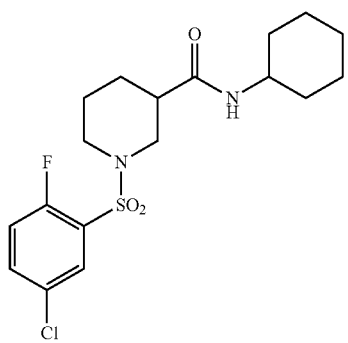

1-[(5-Chloro-2-fluorophenyl)sulfonyl]-N-cyclohexylpiperidine-3-carboxamide

This compound was prepared using procedures analogous to those described in example 1. LCMS: m/z 403.1 (M+H)+; 425.1 (M+Na)+; 827.2 (2M+Na)+.

Example 11

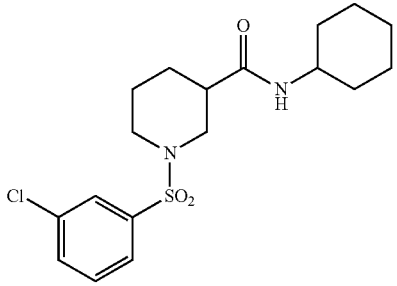

1-[(3-Chlorophenyl)sulfonyl]-N-cyclohexylpiperidine-3-carboxamide

This compound was prepared using procedures analogous to those described in example 1. LCMS: m/z 385.1 (M+H)+; 791.2 (2M+Na)+.

Example 12

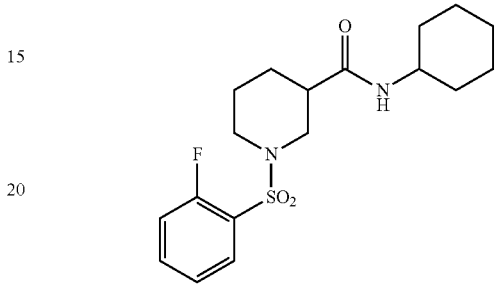

N-Cyclohexyl-1-[(2-fluorophenyl)sulfonyl]piperidine-3-carboxamide

This compound was prepared using procedures analogous to those described in example 1. LCMS: m/z 369.1 (M+H)+; 391.1 (M+Na)+; 759.2 (2M+Na)+.

Example 13

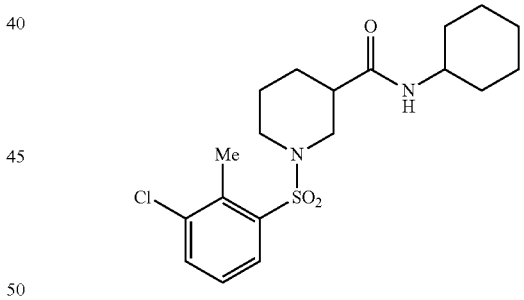

1-[(3-Chloro-2-methylphenyl)sulfonyl]-N-cyclo-
hexylpiperidine-3-carboxamide

This compound was prepared using procedures analogous to those described in example 1. LCMS: m/z 399.1 (M+H)+; 819.2 (2M+Na)+.

Example 14

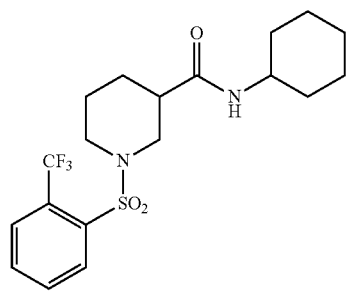

N-Cyclohexyl-1-{[2-(trifluoromethyl)phenyl]
sulfonyl}piperidine-3-carboxamide

This compound was prepared using procedures analogous to those described in example 1. LCMS: m/z 419.1 (M+H)+; 441.1 (M+Na)+; 859.3 (2M+Na)+.

Example 15

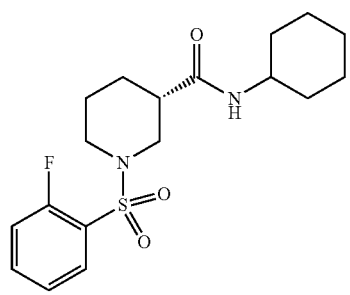

(3S)—N-Cyclohexyl-1-[(2-fluorophenyl)sulfonyl]
piperidine-3-carboxamide

This compound was prepared according to the procedures described in example 1 starting from (3S)-1-(tert-butoxycarbonyl)piperidine-3-carboxylic acid. LCMS: m/z 369.1 (M+H)+

Example 16

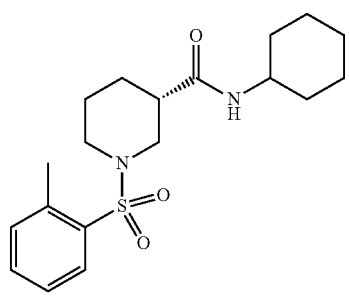

(3S)—N-Cyclohexyl-1-[(2-methylphenyl)sulfonyl]
piperidine-3-carboxamide

This compound was prepared using procedures analogous to those described in example 15. LCMS: m/z 365.1 (M+H)+

Example 17

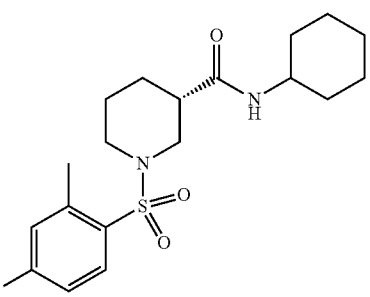

39

(3S)—N-Cyclohexyl-1-[(4-fluoro-2-methylphenyl)sulfonyl]piperidine-3-carboxamide

This compound was prepared using procedures analogous to those described in example 15. LCMS: m/z 383.1 (M+H)+

Example 18

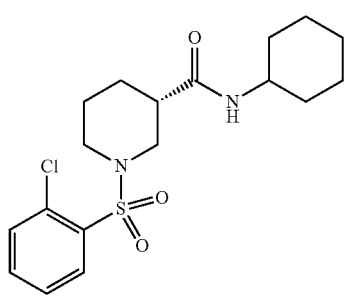

(3S)-1-[(2-Chlorophenyl)sulfonyl]-N-cyclohexylpiperidine-3-carboxamide

This compound was prepared using procedures analogous to those described in example 15. LCMS: m/z 385.1 (M+H)+

Example 19

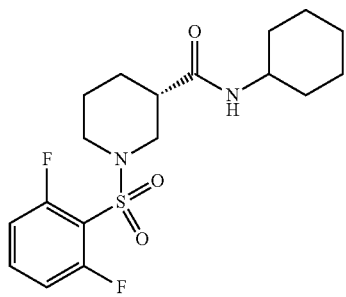

40

(3S)—N-Cyclohexyl-1-[(2,6-difluorophenyl)sulfonyl]piperidine-3-carboxamide

This compound was prepared using procedures analogous to those described in example 15. LCMS: m/z 387.1 (M+H)+

Example 20

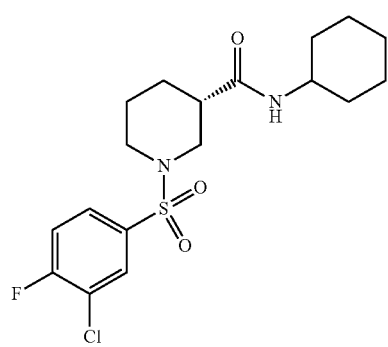

(3S)-1-[(3-Chloro-4-fluorophenyl)sulfonyl]-N-cyclohexylpiperidine-3-carboxamide

This compound was prepared using procedures analogous to those described in example 15. LCMS: m/z 403.1 (M+H)+

Example 21

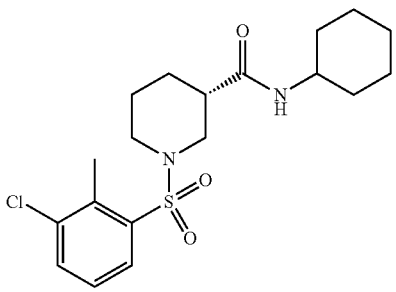

(3S)-1-[(3-Chloro-2-methylphenyl)sulfonyl]-N-cyclohexylpiperidine-3-carboxamide

This compound was prepared using procedures analogous to those described in example 15. LCMS: m/z 399.1 (M+H)+

Example 22

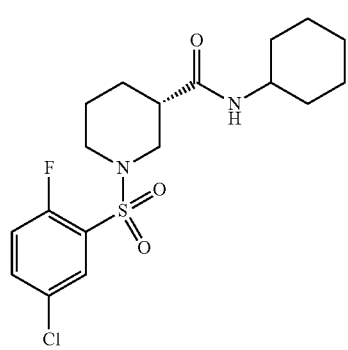

(3S)-1-[(5-Chloro-2-fluorophenyl)sulfonyl]-N-cyclohexylpiperidine-3-carboxamide

This compound was prepared using procedures analogous to those described in example 15. LCMS: m/z 403.1 (M+H)+

Example 23

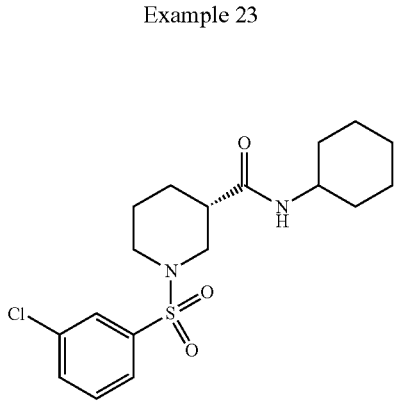

(3S)-1-[(3-Chlorophenyl)sulfonyl]-N-cyclohexylpiperidine-3-carboxamide

This compound was prepared using procedures analogous to those described in example 15. LCMS: m/z 385.1 (M+H)+

Example 24

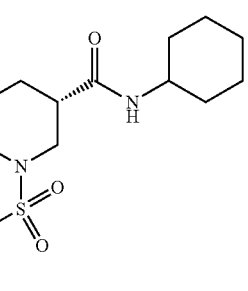

(3S)-1-[(3-Chloro-2-fluorophenyl)sulfonyl]-N-cyclohexylpiperidine-3-carboxamide

This compound was prepared using procedures analogous to those described in example 15. LCMS: m/z 403.1 (M+H)+.

Example 25

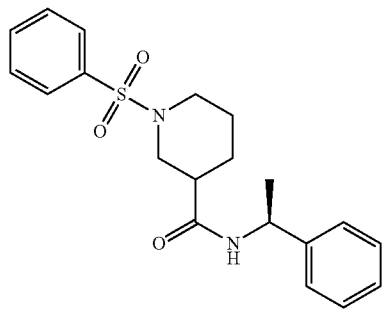

N-[(1S)-1-Phenylethyl]-1-(phenylsulfonyl)piperi-
dine-3-carboxamide

This compound was prepared using procedures analogous to those described in example 1. LCMS: m/z 373.0 (M+H)+; 395.0 (M+Na)+.

Example 27

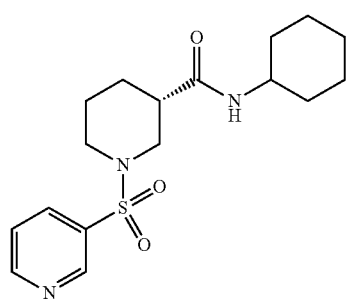

(3S)—N-Cyclohexyl-1-(pyridin-3-ylsulfonyl)piperi-
dine-3-carboxamide

This compound was prepared using procedures analogous to those described in example 15. LCMS: m/z 352.1 (M+H)+; 725.3 (2M+Na).

Example 28

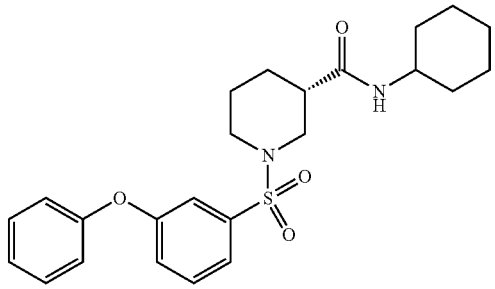

(3S)—N-Cyclohexyl-1-[(3-phenoxyphenyl)sulfonyl]
piperidine-3-carboxamide

This compound was prepared using procedures analogous to those described in example 15. LCMS: m/z 443.2 (M+H)+.

Example 29

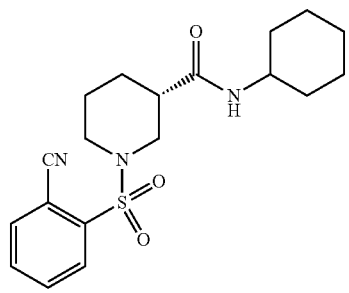

(3S)-1-[(2-Cyanophenyl)sulfonyl]-N-cyclohexylpip-
eridine-3-carboxamide

This compound was prepared using procedures analogous to those described in example 15. LCMS: m/z 376.1 (M+H)+; 773.2 (2M+Na)+.

Example 30

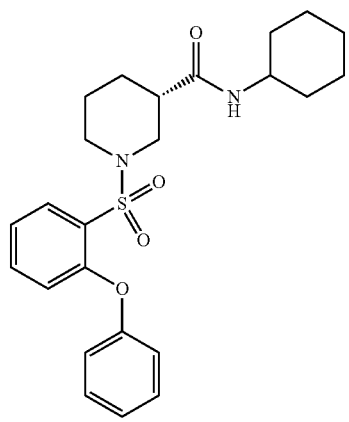

45

(3S)—N-Cyclohexyl-1-[(2-phenoxyphenyl)sulfonyl]
piperidine-3-carboxamide

This compound was prepared using procedures analogous to those described in example 15. LCMS: m/z 443.2 (M+H)+.

Example 31

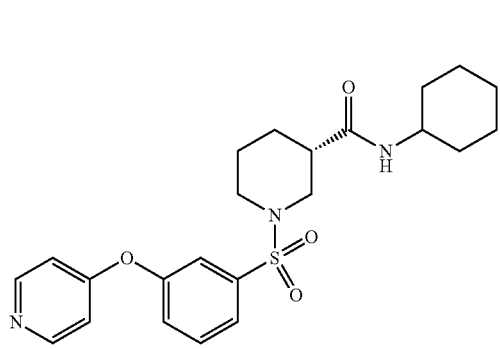

(3S)—N-Cyclohexyl-1-{[3-(pyridin-4-yloxy)phenyl]
sulfonyl}piperidine-3-carboxamide trifluoroacetate This compound was prepared using procedures analogous to those described in example 15. LCMS: m/z 444.1 (M+H)+; 466.1 (M+Na)+.

Example 32

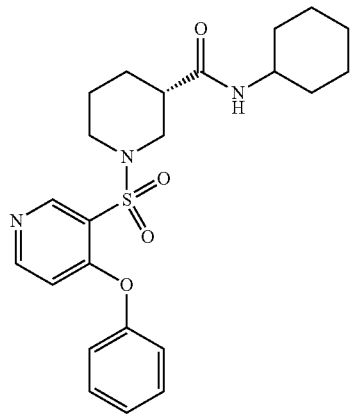

46

(3S)—N-Cyclohexyl-1-[(4-phenoxypyridin-3-yl)
sulfonyl]piperidine-3-carboxamide trifluoroacetate This compound was prepared using procedures analogous to those described in example 15. LCMS: m/z 444.1 (M+H)+.

Example 33

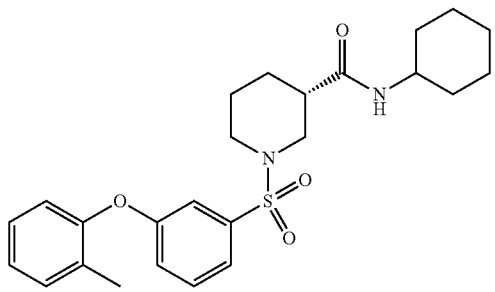

(3S)—N-Cyclohexyl-1-{[3-(2-methylphenoxy)phe-
nyl]sulfonyl}piperidine-3-carboxamide This compound was prepared using procedures analogous to those described in example 15. LCMS: m/z 457.1 (M+H)+.

Example 34

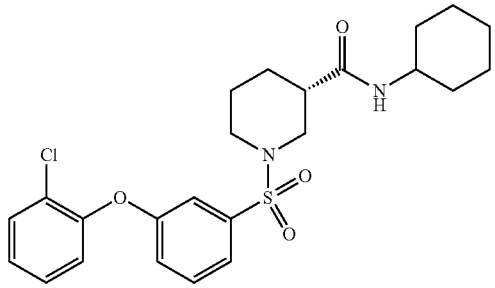

47

(3S)-{[3-(2-Chlorophenoxy)phenyl]sulfonyl}-N-cyclohexylpiperidine-3-carboxamide

This compound was prepared using procedures analogous to those described in example 15. LCMS: m/z 477.1 (M+H)+.

Example 35

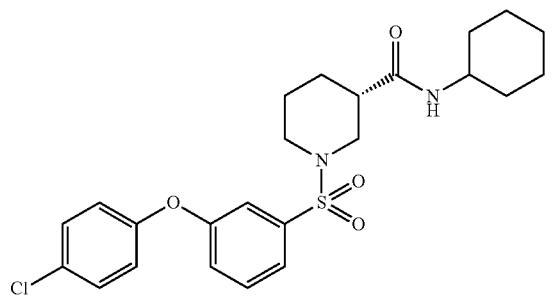

(3S)-{[3-(4-Chlorophenoxy)phenyl]sulfonyl}-N-cyclohexylpiperidine-3-carboxamide

This compound was prepared using procedures analogous to those described in example 15. LCMS: m/z 477.1 (M+H)+.

Example 36

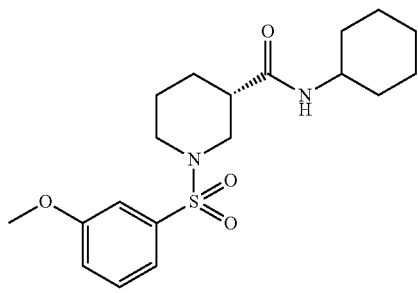

48

(3S)—N-Cyclohexyl-1-[(3-methoxyphenyl)sulfonyl]piperidine-3-carboxamide

This compound was prepared using procedures analogous to those described in example 15. LCMS: m/z 381.1 (M+H)+; 783.3 (2M+Na)+.

Example 37

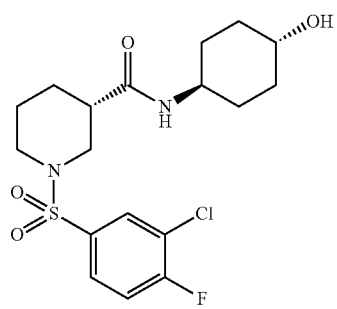

(3S)-1-[(3-Chloro-4-fluorophenyl)sulfonyl]-N-(trans-4-hydroxycyclohexyl)piperidine-3-carboxamide This compound was prepared using procedures analogous to those described in example 15. LCMS: m/z 419.0 (M+H)+; 441.1 (M+Na)+.

Example 38

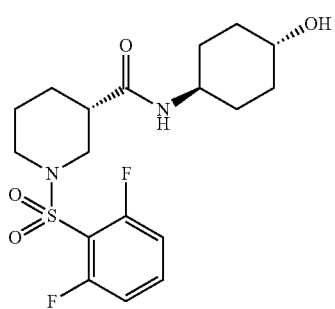

49

(3S)-1-[(2,6-Difluorophenyl)sulfonyl]-N-(trans-4-hydroxycyclohexyl)piperidine-3-carboxamide This compound was prepared using procedures analogous to those described in example 15. LCMS: m/z 403.1 (M+H)+; 425.1 (M+Na)+; 827.2 (2M+Na)+.

Example 39

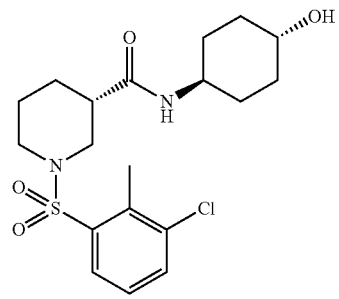

(3S)-1-[(3-Chloro-2-methylphenyl)sulfonyl]-N-(trans-4-hydroxycyclohexyl)piperidine-3-carboxamide This compound was prepared using procedures analogous to those described in example 15. LCMS: m/z 415.0 (M+H)+; 851.2 (2M+Na)+.

Example 40

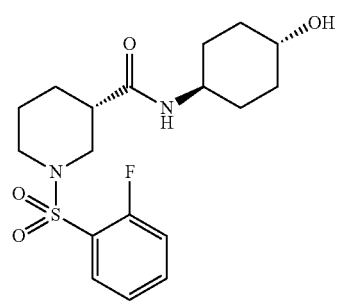

50

(3S)-1-[(2-Fluorophenyl)sulfonyl]-N-(trans-4-hydroxycyclohexyl)piperidine-3-carboxamide This compound was prepared using procedures analogous to those described in example 15. LCMS: m/z 385.1 (M+H)+; 791.3 (2M+Na)+.

Example 41

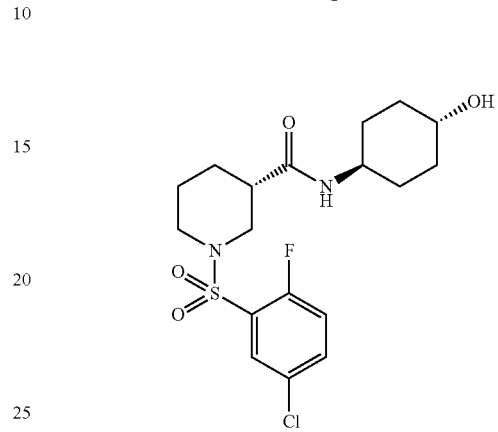

(3S)-1-[(5-Chloro-2-fluorophenyl)sulfonyl]-N-(trans-4-hydroxycyclohexyl)piperidine-3-carboxamide This compound was prepared using procedures analogous to those described in example 15. LCMS: m/z 419.1 (M+H)+; 859.2 (2M+Na)+.

Example 42

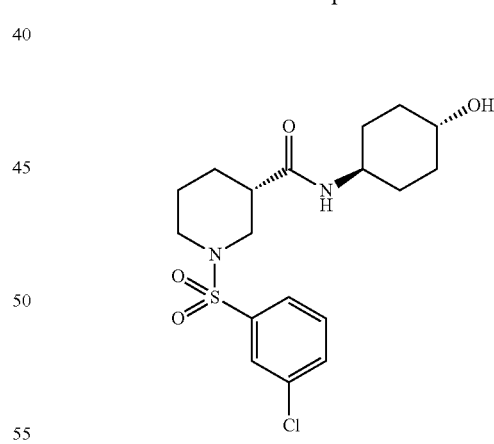

51

(3S)-1-[(3-Chlorophenyl)sulfonyl]-N-(trans-4-hydroxycyclohexyl)piperidine-3-carboxamide This compound was prepared using procedures analogous to those described in example 15. LCMS: m/z 401.0 (M+H)+; 823.2 (2M+Na)+.

Example 43

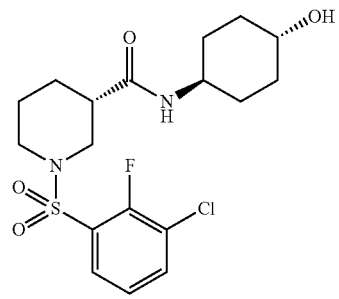

(3S)-1-[(3-Chloro-2-fluorophenyl)sulfonyl]-N-(trans-4-hydroxycyclohexyl)piperidine-3-carboxamide This compound was prepared using analogous procedures to those described in example 15. LCMS: m/z 419.1 (M+H)+.

Example 44

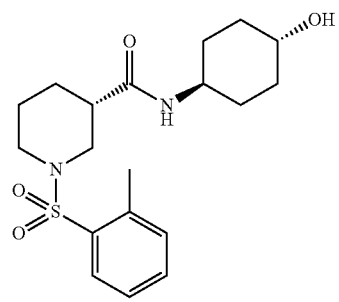

52

(3S)—N-(trans-4-Hydroxycyclohexyl)-1-[(2-methylphenyl)sulfonyl]piperidine-3-carboxamide This compound was prepared using analogous procedures to those described in example 15. LCMS: m/z 381.1 (M+H)+; 783.3 (2M+Na)+.

Example 45

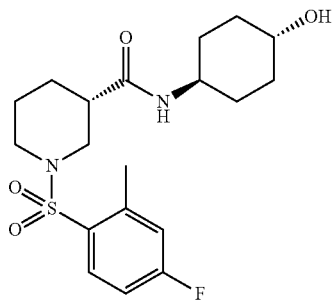

(3S)-1-[(4-Fluoro-2-methylphenyl)sulfonyl]-N-(trans-4-hydroxycyclohexyl)piperidine-3-carboxamide This compound was prepared using analogous procedures to those described in example 15. LCMS: m/z 399.1 (M+H)+; 819.3 (2M+Na)+.

Example 46

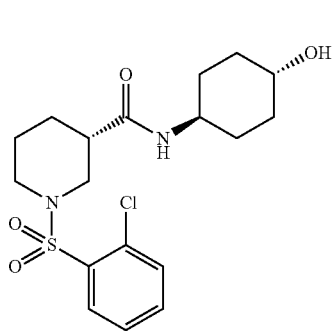

(3S)-1-[(2-Chlorophenyl)sulfonyl]-N-(trans-4-hydroxycyclohexyl)piperidine-3-carboxamide This compound was prepared using analogous procedures to those described in example 15. LCMS: m/z 401.0 (M+H)+; 823.2 (2M+Na)+.

Example 47

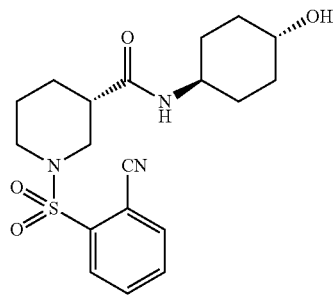

(3S)-1-[(2-Cyanophenyl)sulfonyl]-N-(trans-4-hydroxycyclohexyl)piperidine-3-carboxamide This compound was prepared using analogous procedures to those described in example 15. LCMS: m/z 392.1 (M+H)+; 414.0 (M+Na)+.

Example 48

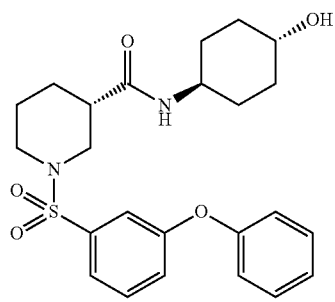

(3S)—N-(trans-4-Hydroxycyclohexyl)-1-[(3-phenoxyphenyl)sulfonyl]piperidine-3-carboxamide This compound was prepared using analogous procedures to those described in example 15. LCMS: m/z 459.1 (M+H)+.

Example 49

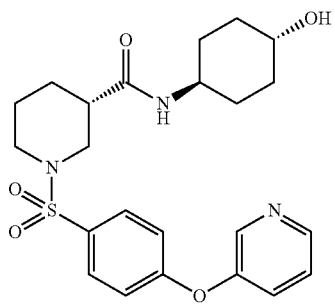

(3S)—N-(trans-4-Hydroxycyclohexyl)-1-{[4-(pyridin-3-yloxy)phenyl]sulfonyl}piperidine-3-carboxamide This compound was prepared using analogous procedures to those described in example 15. LCMS: m/z 460.1 (M+H)+.

Example 50

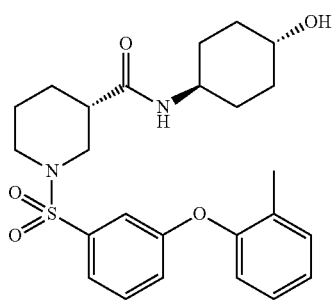

(3S)—N-(trans-4-Hydroxycyclohexyl)-1-{[3-(2-methylphenoxy)phenyl]sulfonyl}-piperidine-3-carboxamide This compound was prepared using analogous procedures to those described in example 15. LCMS: m/z 473.2 (M+H)+.

Example 51

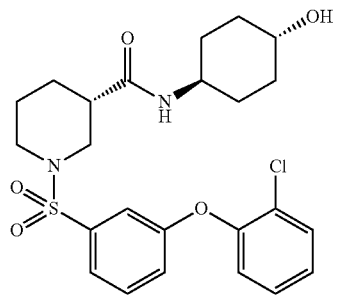

(3S)-1-{[3-(2-Chlorophenoxy)phenyl]sulfonyl}-N-(trans-4-hydroxycyclohexyl)-piperidine-3-carboxamide This compound was prepared using analogous procedures to those described in example 15. LCMS: m/z 493.1 (M+H)+.

Example 52

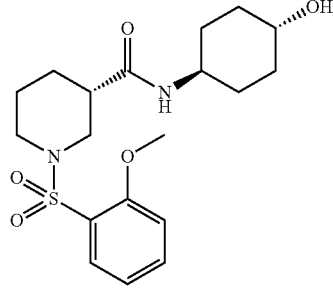

(3S)—N-(trans-4-Hydroxycyclohexyl)-1-[(2-methoxyphenyl)sulfonyl]piperidine-3-carboxamide This compound was prepared using analogous procedures to those described in example 15. LCMS: m/z 397.2 (M+H)+; 815.3 (2M+Na)+.

Example 53

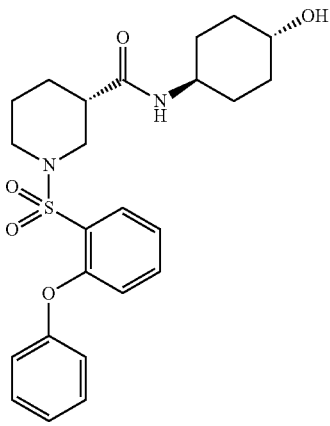

(3S)—N-(trans-4-Hydroxycyclohexyl)-1-[(2-phenoxyphenyl)sulfonyl]piperidine-3-carboxamide This compound was prepared using analogous procedures to those described in example 15. LCMS: m/z 459.1 (M+H)+.

Example 54

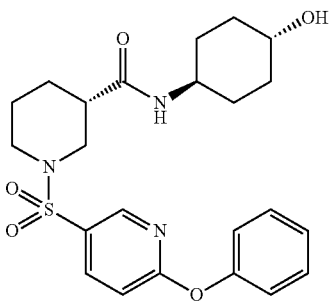

57

(3S)—N-(trans-4-Hydroxycyclohexyl)-1-[(6-phenoxypyridin-3-yl)sulfonyl]piperidine-3-carboxamide This compound was prepared using analogous procedures to those described in example 15. LCMS: m/z 460.1 (M+H)+.

Example 55

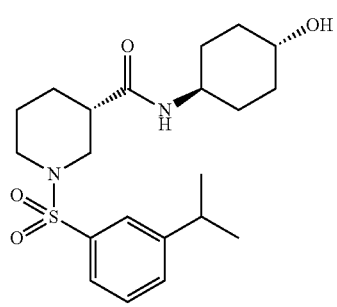

(3S)—N-(trans-4-Hydroxycyclohexyl)-1-[(3-isopropylphenyl)sulfonyl]piperidine-3-carboxamide This compound was prepared using analogous procedures to those described in example 15. LCMS: m/z 409.2 (M+H)+; 839.4 (2M+Na)+.

Example 56

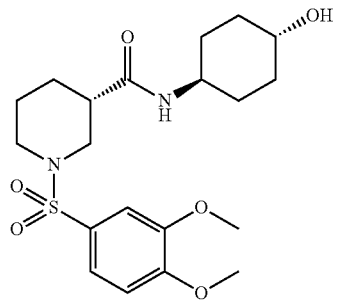

58

(3S)-1-[(3,4-Dimethoxyphenyl)sulfonyl]-N-(trans-4-hydroxycyclohexyl)piperidine-3-carboxamide This compound was prepared using analogous procedures to those described in example 15. LCMS: m/z 427.1 (M+H)+.

Example 57

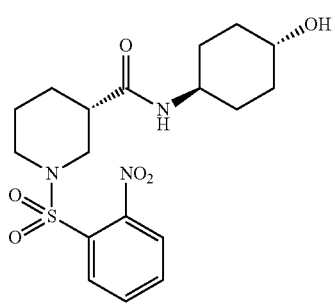

(3S)—N-(trans-4-Hydroxycyclohexyl)-1-[(2-nitrophenyl)sulfonyl]piperidine-3-carboxamide This compound was prepared using analogous procedures to those described in example 15. LCMS: m/z 412.1 (M+H)+; 845.2 (2M+Na)+.

Example 58

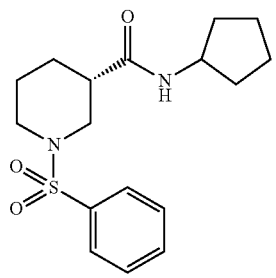

59

(3S)—N-Cyclopentyl-1-(phenylsulfonyl)piperidine-3-carboxamide

This compound was prepared using analogous procedures to those described in example 15. LCMS: m/z 337.1 (M+H)+.

Example 59

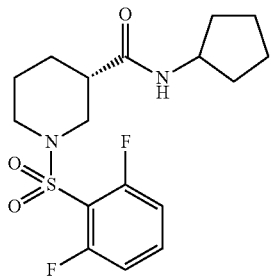

(3S)—N-Cyclopentyl-1-[(2,6-difluorophenyl)sulfonyl]piperidine-3-carboxamide

This compound was prepared using analogous procedures to those described in example 15. LCMS: m/z 373.1 (M+H)+.

Example 60

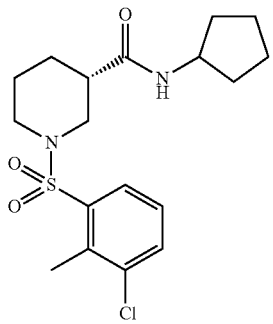

60

(3S)-1-[(3-Chloro-2-methylphenyl)sulfonyl]-N-cyclopentylpiperidine-3-carboxamide This compound was prepared using analogous procedures to those described in example 15. LCMS: m/z 385.1 (M+H)+.

Example 61

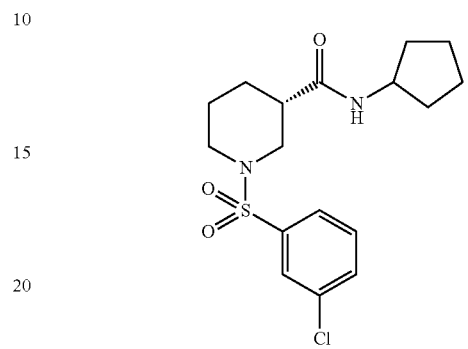

(3S)-1-[(3-Chlorophenyl)sulfonyl]-N-cyclopentylpiperidine-3-carboxamide

This compound was prepared using analogous procedures to those described in example 15. LCMS: m/z 371.1 (M+H)+; 763.1 (2M+Na)+.

Example 62

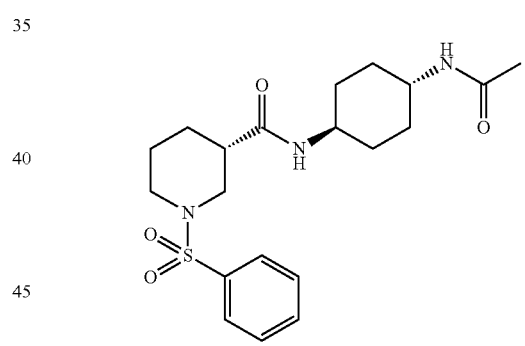

(3S)—N-[trans-4-(Acetylamino)cyclohexyl]-1-(phenylsulfonyl)piperidine-3-carboxamide Step 1.
At room temperature, to a solution of trans-cyclohexane-1,4-diamine (0.0261 g, 0.23 mmol) in acetonitrile (0.2 mL), was slowly added a solution of acetyl chloride (16.4 μL, 0.23 mmol) in acetonitrile (0.3 mL), followed by diisopropylethylamine. The mixture was stirred at r.t. for 30 min.

Step 2.
To the above mixture was slowly added a mixture of (3S)-1-(tert-butoxycarbonyl)piperidine-3-carboxylic acid (50 mg, 0.22 mmol), and benzotriazol-1-yloxytris(dimethylamino)phosphonium hexafluorophosphate (101 mg, 0.23 mmol) in acetonitrile (0.5 mL) with stirring at r.t., followed by diisopropylethylamine (55 μL). After stirring for 2 hours at r.t, the reaction mixture was concentrated. The residue was used in the next step.

Step 3.

The residue from Step 2 in 4 N HCl solution in dioxane (1.5 mL) was stirred at r.t. for 1 hour. After removal of solvent, the residue was used in the following step.

Step 4.

A mixture of the above residue from Step 3, K$_2$CO$_3$ (90 mg, 0.65 mmol), and benzenesulfonyl chloride (41.7 μL, 0.33 mmol) in acetonitrile (0.3 mL) was stirred at r.t. overnight. 5.1 mg (5.7%) of final product was obtained after purification with prep. HPLC. LCMS: m/z 408.1 (M+H)+.

Example 63

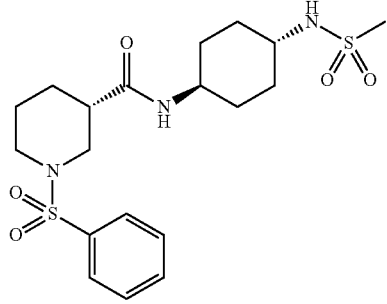

(3S)—N-{trans-4-[(Methylsulfonyl)amino]cyclohexyl}-1-(phenylsulfonyl)piperidine-3-carboxamide This compound was prepared according to procedures analogous to example 63. LCMS: m/z 444.1 (M+H)+; 466.0 (M+Na)+.

Example 64

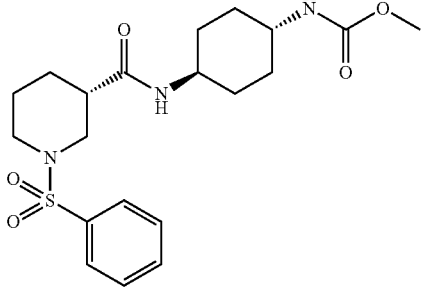

Methyl[trans-4-({[(3S)-1-(phenylsulfonyl)piperidin-3-yl]carbonyl}amino)cyclohexyl]carbamate This compound was prepared according to procedures analogous to example 63. LCMS: m/z 424.1 (M+H)+; 446.1 (M+Na)+.

Example 65

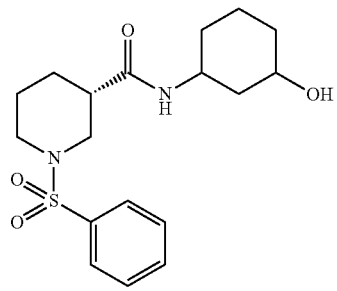

(3S)—N-(3-Hydroxycyclohexyl)-1-(phenylsulfonyl)piperidine-3-carboxamide

This compound was prepared according to procedures analogous to example 15. LCMS: m/z 367.1 (M+H)+; 755.3 (2M+Na)+.

Example 66

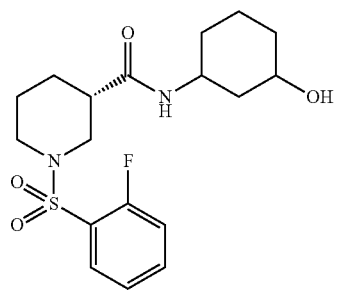

63

(3S)-1-[(2-Fluorophenyl)sulfonyl]-N-(3-hydroxycyclohexyl)piperidine-3-carboxamide This compound was prepared according to procedures analogous to example 15. LCMS: m/z 385.1 (M+H)+; 791.2 (2M+Na)+.

Example 67

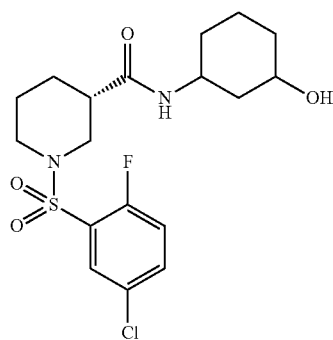

(3S)-1-[(5-Chloro-2-fluorophenyl)sulfonyl]-N-(3-hydroxycyclohexyl)piperidine-3-carboxamide This compound was prepared according to procedures analogous to example 15. LCMS: m/z 419.0 (M+H)+; 859.0 (2M+Na)+.

Example 68

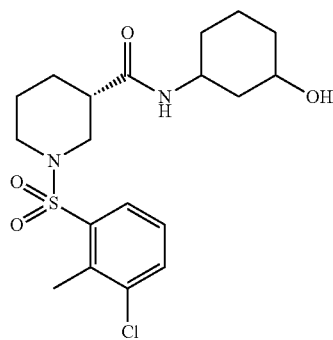

64

(3S)-1-[(3-Chloro-2-methylphenyl)sulfonyl]-N-(3-hydroxycyclohexyl)piperidine-3-carboxamide This compound was prepared according to procedures analogous to example 15. LCMS: m/z 415.1 (M+H)+; 437.0 (M+Na)+.

Example 69

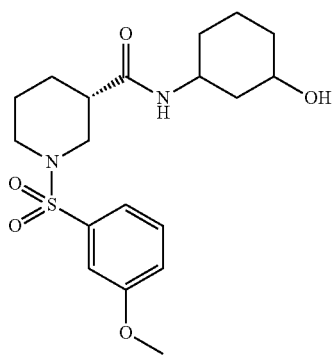

(3S)—N-(3-Hydroxycyclohexyl)-1-[(3-methoxyphenyl)sulfonyl]piperidine-3-carboxamide This compound was prepared according to procedures analogous to example 15. LCMS: m/z 397.1 (M+H)+; 815.3 (2M+Na)+.

Example 70

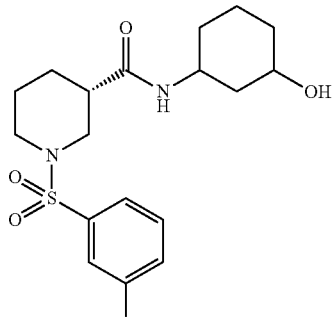

(3S)-1-[(3-Chlorophenyl)sulfonyl]-N-(3-hydroxycyclohexyl)piperidine-3-carboxamide This compound was prepared according to procedures analogous to example 15. LCMS: m/z 401.0 (M+H)+; 823.0 (2M+Na)+.

Example 71

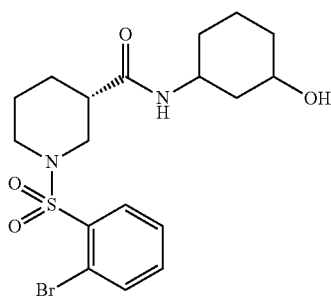

(3S)-1-[(2-Bromophenyl)sulfonyl]-N-(3-hydroxycyclohexyl)piperidine-3-carboxamide This compound was prepared according to procedures analogous to example 15. LCMS: m/z 445.0 (M+H)+.

Example 72

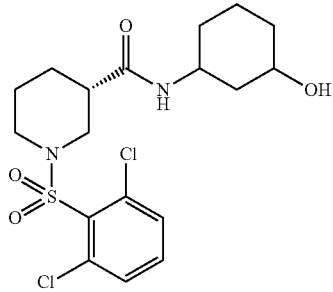

(3S)—N-(3-Hydroxycyclohexyl)-1-[(3-methylphenyl)sulfonyl]piperidine-3-carboxamide This compound was prepared according to procedures analogous to example 15. LCMS: m/z 381.1 (M+H)+; 783.2 (2M+Na)+.

Example 73

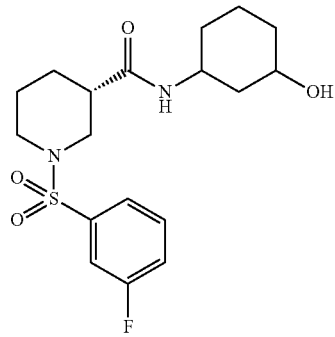

(3S)-1-[(3-Fluorophenyl)sulfonyl]-N-(3-hydroxycyclohexyl)piperidine-3-carboxamide This compound was prepared according to procedures analogous to example 15. LCMS: m/z 385.1 (M+H)+; 791.2 (2M+Na)+.

Example 74

(3S)-1-[(2,6-Dichlorophenyl)sulfonyl]-N-(3-hydroxycyclohexyl)piperidine-3-carboxamide This compound was prepared according to procedures analogous to example 15. LCMS: m/z 435.0 (M+H)+.

Example 75

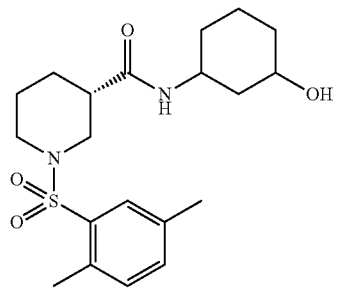

(3S)-1-[(2,5-Dimethylphenyl)sulfonyl]-N-(3-hydroxycyclohexyl)piperidine-3-carboxamide This compound was prepared according to procedures analogous to example 15. LCMS: m/z 395.1 (M+H)+; 811.2 (2M+Na)+.

Example 76

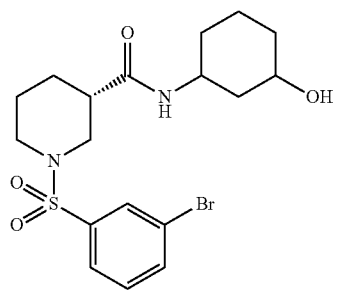

(3S)-1-[(3-Bromophenyl)sulfonyl]-N-(3-hydroxycyclohexyl)piperidine-3-carboxamide This compound was prepared according to procedures analogous to example 15. LCMS: m/z 445.0 (M+H)+.

Example 77

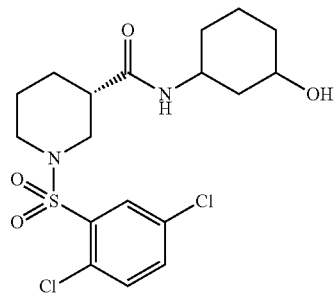

(3S)-1-[(2,5-Dichlorophenyl)sulfonyl]-N-(3-hydroxycyclohexyl)piperidine-3-carboxamide This compound was prepared according to procedures analogous to example 1. LCMS: m/z 435.0 (M+H)+; 893.0 (2M+Na)+.

Example 78

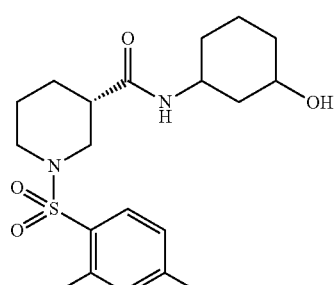

(3S)-1-[(2,4-Difluorophenyl)sulfonyl]-N-(3-hydroxycyclohexyl)piperidine-3-carboxamide This compound was prepared according to procedures analogous to example 15. LCMS: m/z 403.1 (M+H)+; 827.2 (2M+Na)+.

Example 79

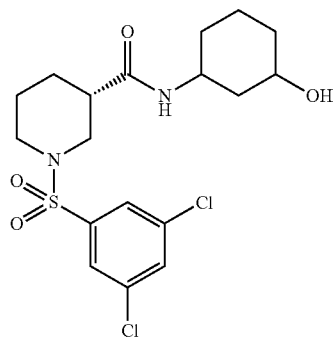

(3S)-1-[(3,5-Dichlorophenyl)sulfonyl]-N-(3-hydroxycyclohexyl)piperidine-3-carboxamide This compound was prepared according to procedures analogous to example 15. LCMS: m/z 435.0 (M+H)+; 893.0 (2M+Na)+.

Example 80

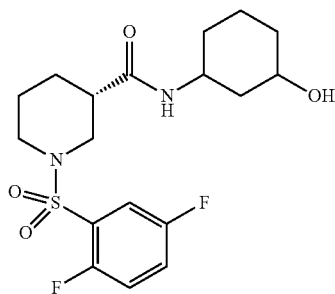

(3S)-1-[(2,5-Difluorophenyl)sulfonyl]-N-(3-hydroxycyclohexyl)piperidine-3-carboxamide This compound was prepared according to procedures analogous to example 15. LCMS: m/z 403.1 (M+H)+; 827.2 (2M+Na)+.

Example 81

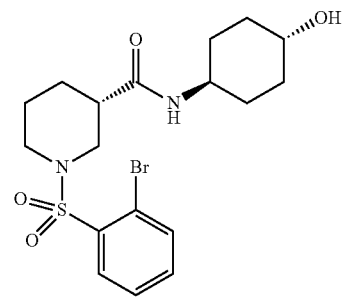

(3S)-1-[(2-Bromophenyl)sulfonyl]-N-(trans-4-hydroxycyclohexyl)piperidine-3-carboxamide This compound was prepared according to procedures analogous to example 15. LCMS: m/z 445.0 (M+H)+.

Example 82

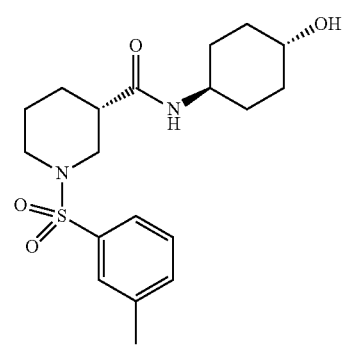

(3S)—N-(trans-4-Hydroxycyclohexyl)-1-[(3-methylphenyl)sulfonyl]piperidine-3-carboxamide This compound was prepared according to procedures analogous to example 15. LCMS: m/z 381.1 (M+H)+; 783.3 (2M+Na)+.

Example 83

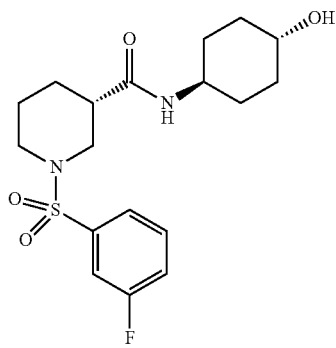

(3S)-1-[(3-Fluorophenyl)sulfonyl]-N-(trans-4-hydroxycyclohexyl)piperidine-3-carboxamide This compound was prepared according to procedures analogous to example 15. LCMS: m/z 385.1 (M+H)+; 791.2 (2M+Na)+.

Example 84

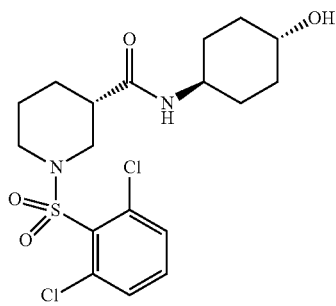

(3S)-1-[(2,6-Dichlorophenyl)sulfonyl]-N-(trans-4-hydroxycyclohexyl)piperidine-3-carboxamide This compound was prepared according to procedures analogous to example 15. LCMS: m/z 435.1 (M+H)+.

Example 85

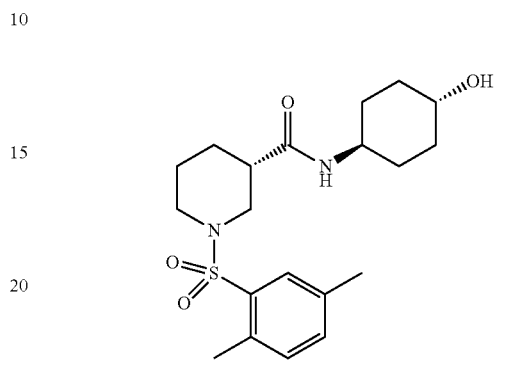

(3S)-1-[(2,5-Dimethylphenyl)sulfonyl]-N-(trans-4-hydroxycyclohexyl)piperidine-3-carboxamide This compound was prepared according to procedures analogous to example 15. LCMS: m/z 395.1 (M+H)+; 811.3 (2M+Na)+.

Example 86

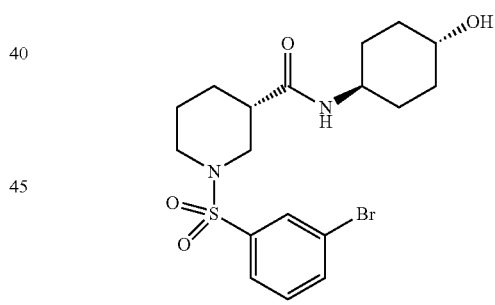

(3S)-1-[(3-Bromophenyl)sulfonyl]-N-(trans-4-hydroxycyclohexyl)piperidine-3-carboxamide This compound was prepared according to procedures analogous to example 15. LCMS: m/z 445.0 (M+H)+.

Example 87

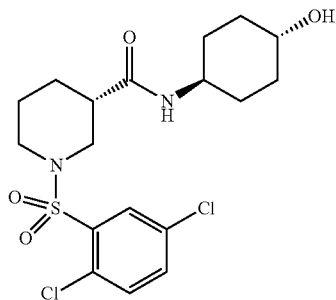

(3S)-1-[(2,5-Dichlorophenyl)sulfonyl]-N-(trans-4-hydroxycyclohexyl)piperidin-3-carboxamide This compound was prepared according to procedures analogous to example 15. LCMS: m/z 435.0 (M+H)+.

Example 88

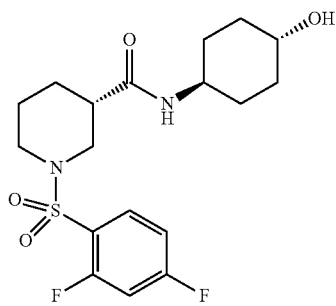

(3S)-1-[(2,4-Difluorophenyl)sulfonyl]-N-(trans-4-hydroxycyclohexyl)piperidine-3-carboxamide This compound was prepared according to procedures analogous to example 15. LCMS: m/z 403.1 (M+H)+; 827.2 (2M+Na)+.

Example 89

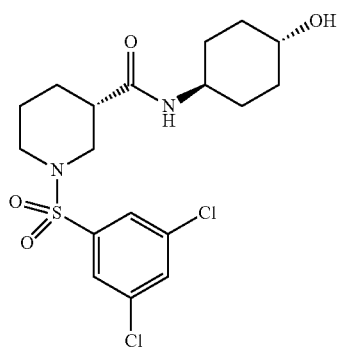

(3S)-1-[(3,5-Dichlorophenyl)sulfonyl]-N-(trans-4-hydroxycyclohexyl)piperidine-3-carboxamide This compound was prepared according to procedures analogous to example 15. LCMS: m/z 435.0 (M+H)+.

Example 90

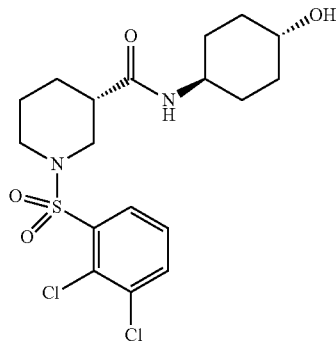

(3S)-1-[(2,3-Dichlorophenyl)sulfonyl]-N-(trans-4-hydroxycyclohexyl)piperidine-3-carboxamide This compound was prepared using the similar procedures described in example 15. LCMS: m/z 435.0 (M+H)+.

Example 91

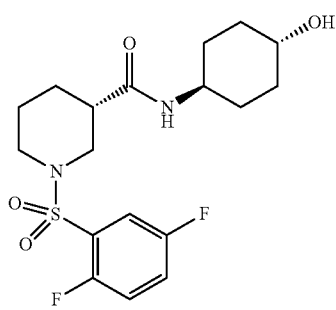

(3S)-1-[(2,5-Difluorophenyl)sulfonyl]-N-(trans-4-hydroxycyclohexyl)piperidine-3-carboxamide This compound was prepared according to procedures analogous to example 15. LCMS: m/z 403.1 (M+H)+; 827.2 (2M+Na)+.

Example 92

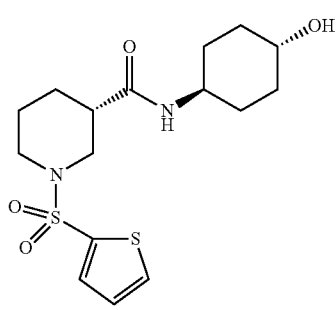

(3S)-N-(trans-4-Hydroxycyclohexyl)-1-(2-thienyl-sulfonyl)piperidine-3-carboxamide This compound was prepared according to procedures analogous to example 15. LCMS: m/z 373.1 (M+H)+; 767.2 (2M+Na)+.

Example 93

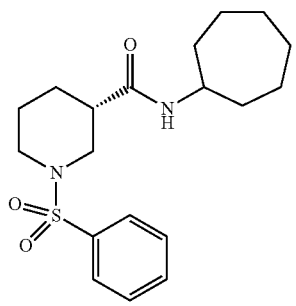

(3S)—N-Cycloheptyl-1-(phenylsulfonyl)piperidine-3-carboxamide

This compound was prepared according to procedures analogous to example 15. LCMS: m/z 365.1 (M+H)+; 751.3 (2M+Na)+.

Example 94

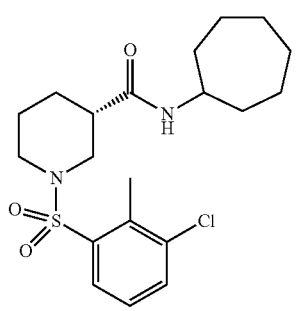

(3S)-1-[(3-Chloro-2-methylphenyl)sulfonyl]-N-cycloheptylpiperidine-3-carboxamide This compound was prepared according to procedures analogous to example 15. LCMS: m/z 413.1 (M+H)+; 847.2 (2M+Na)+.

Example 95

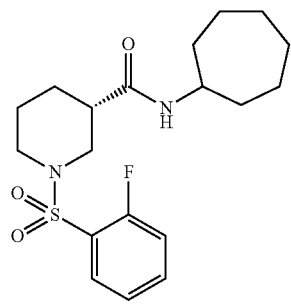

(3S)—N-Cycloheptyl-1-[(2-fluorophenyl)sulfonyl]piperidine-3-carboxamide

This compound was prepared according to procedures analogous to example 15. LCMS: m/z 383.1 (M+H)+; 787.3 (2M+Na)+.

Example 96

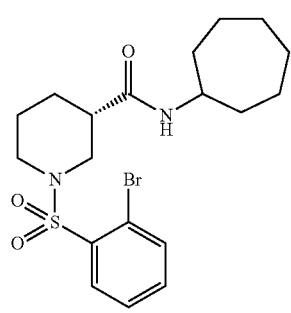

(3S)-1-[(2-Bromophenyl)sulfonyl]-N-cycloheptylpiperidine-3-carboxamide

This compound was prepared according to procedures analogous to example 15. LCMS: m/z 443.1 (M+H)+.

Example 97

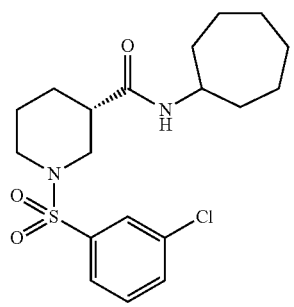

(3S)-1-[(3-Chlorophenyl)sulfonyl]-N-cycloheptylpiperidine-3-carboxamide

This compound was prepared according to procedures analogous to example 15. LCMS: m/z 399.1 (M+H)+; 819.3 (2M+Na)+.

Example 98

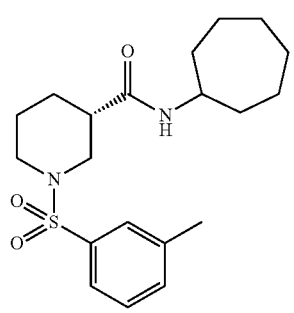

(3S)—N-Cycloheptyl-1-[(3-methylphenyl)sulfonyl]piperidine-3-carboxamide

This compound was prepared according to procedures analogous to example 15. LCMS: m/z 379.1 (M+H)+; 779.3 (2M+Na)+.

Example 99

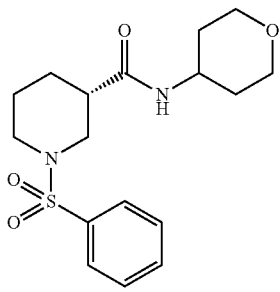

(3S)-1-(Phenylsulfonyl)-N-(tetrahydro-2H-pyran-4-yl)piperidine-3-carboxamide

This compound was prepared according to procedures analogous to example 15. LCMS: m/z 353.1 (M+H)+; 727.2 (2M+Na)+.

Example 100

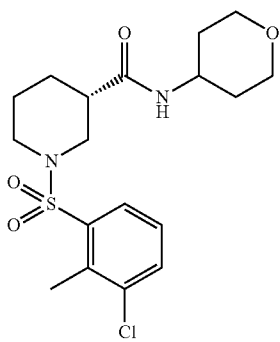

(3S)-1-[(3-Chloro-2-methylphenyl)sulfonyl]-N-(tetrahydro-2H-pyran-4-yl)piperidine-3-carboxamide This compound was prepared according to procedures analogous to example 15. LCMS: m/z 401.1 (M+H)+; 423.0 (M+Na)+.

Example 101

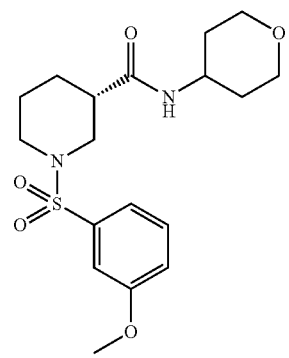

(3S)-1-[(3-Methoxyphenyl)sulfonyl]-N-(tetrahydro-2H-pyran-4-yl)piperidine-3-carboxamide This compound was prepared according to procedures analogous to example 15. LCMS: m/z 383.1 (M+H)+; 787.3 (M+Na)+.

Example 102

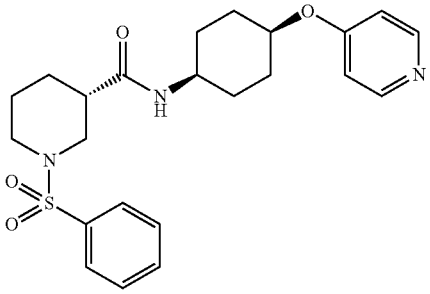

(3S)-1-(Phenylsulfonyl)-N-[4-(pyridin-4-yloxy)cyclohexyl]piperidine-3-carboxamide Under a nitrogen atmosphere, to a mixture of (3S)—N-(trans-4-hydroxycyclohexyl)-1-(phenylsulfonyl)piperidine-3-carboxamide (25 mg, 0.068 mmol), 4-pyridinol (9.7 mg, 0.10 mmol), and triphenylphosphine (26.8 mg, 0.10 mmol) in tetrahydrofuran (0.5 mL) was added a solution of diethyl azodicarboxylate (16 μL, 0.10 mmol) in tetrahydrofuran (0.1 mL). The mixture was stirred at r.t. overnight. The product was purified with prep. HPLC. 1.9 mg product was obtained, yield: 6.3%. LCMS: m/z 444.2 (M+H)+; 887.2 (2M+Na)+.

Example 103

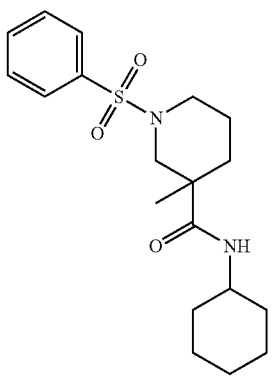

N-Cyclohexyl-3-methyl-1-(phenylsulfonyl)piperidine-3-carboxamide

Step 1.

A mixture of ethyl piperidine-3-carboxylate (1.00 g, 6.36 mmol), benzenesulfonyl chloride (0.812 mL, 6.36 mmol), and triethylamine (2.66 mL, 19.1 mmol) in methylene chloride (10.0 mL) was stirred at r.t. for 2 hours. The mixture was quenched with water, then extracted with ethyl acetate. The extract was washed with 1N HCl solution, water, sat'd sodium bicarbonate solution, water, and brine, successively. Then, the extract was dried over sodium sulfate (anhydrous). After filtration, the filtrate was concentrated to yield 1.79 g (94%) of ethyl 1-(phenylsulfonyl)piperidine-3-carboxylate.

Step 2.

At r.t., to the solution of ethyl 1-(phenylsulfonyl)piperidine-3-carboxylate (0.50 g, 2.0 mmol) in tetrahydrofuran (5.0 mL), was slowly added 1.0 M of lithium hexamethyldisilazide in hexane (2.5 mL, 2.5 mmol) with stirring. After stirring for 30 min, to the mixture was added methyl iodide (157 ul, 2.5 mmol). The mixture was stirred at r.t. overnight and was quenched with 10% citric acid, then extracted with ethyl acetate. The extract was washed with water, sat'd sodium bicarbonate solution, water, and brine, successively. The extract was then dried over sodium sulfate (anhydrous). After filtration, the filtrate was concentrated to yield 200 mg (40%) of ethyl 3-methyl-1-(phenylsulfonyl)piperidine-3-carboxylate.

Step 3.

At r.t., to a solution of cyclohexanamine (19.1 mg, 0.19 mmol) in methylene chloride (0.1 mL) was added 2.0 M of trimethylaluminum in toluene (96 ul, 0.19 mmol). After stirring for 30 min, to the solution was added a solution of ethyl 3-methyl-1-(phenylsulfonyl)piperidine-3-carboxylate (35 mg, 0.11 mmol) in methylene chloride (0.1 mL). The mixture was stirred at r.t for 10 min, then, at 40° C. overnight. After cooling to r.t., the mixture was purified with combi-flash. The product was further purified with prep. HPLC. 1.3 mg final product was obtained. Yield: 3.2%. LCMS: m/z 365.1 (M+H)+; 751.3 (2M+Na)+.

Example 104

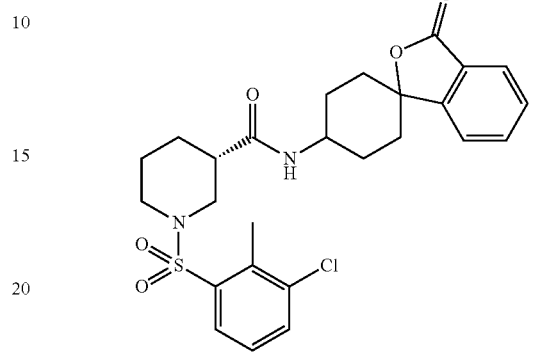

(3S)-1-[(3-Chloro-2-methylphenyl)sulfonyl]-N-(3-oxo-3H-spiro[2-benzofuran-1,1'-cyclohexan]-4'-yl)piperidine-3-carboxamide Step 1.

Under nitrogen atmosphere, a solution of 1.0 M of dibutylmagnesium in heptane (2.6 mL, 2.6 mmol) was slowly added to a solution of 2-bromobenzoic acid (1.0 g, 4.97 mmol) in tetrahydrofuran (10 mL) which was cooled below −15° C. with stirring. Then, to the mixture was added a solution of 1.60 M of n-butyllithium in hexane (3.40 mL, 5.44 mmol) below −15° C. over 20 min under effective stirring. After stirring below −15° C. for 1 hour, a solution of 1,4-cyclohexanedione mono-ethlene ketal (0.932 g, 5.97 mmol) in tetrahydrofuran (3 mL) was added the reaction mixture at −15° C. After stirring for 1 hour at −15° C., the reaction mixture was quenched with 2N HCl solution (10 mL). The resulting mixture was stirred at r.t. overnight, then extracted with ethyl acetate. The extract was washed with 10% citric acid, water, sat'd sodium bicarbonate solution, water, and brine, successively. After drying over anhydrous sodium sulfate, the solid was filtered off. The filtrate was concentrated. The resulting residue was heated at refluxing in acetone (5 mL) and 3 N HCl solution (6 mL) for 4 hours. After cooling, it was concentrated. The product was taken into ethyl acetate. The organic solution was washed with water, 1N HCl solution, water, sat'd sodium bicarbonate, water, brine; dried over anhydrous sodium sulfate. After filtration, the filtrate was concentrated. The resulting residue was purified with flash column. 0.486 g (yield: 45%) of 3H,4'H-spiro[2-benzofuran-1,1'-cyclohexane]-3,4'-dione was obtained.

Step 2.

To a solution of 3H,4'H-spiro[2-benzofuran-1,1'-cyclohexane]-3,4'-dione (100 mg, 0.46 mmol) in methanol (1 mL) was added sodium borohydride (35 mg, 0.92 mmol) with stirring. The mixture was stirred at r.t for 2 hours, then quenched with water. Then, the mixture was concentrated and extracted with ethyl acetate. The extract was washed with 10% citric acid, water, and brine, successively; then dried over anhydrous sodium sulfate. After filtration the filtrate was concentrated to yield 101 mg of 4'-hydroxy-3H-spiro[2-benzofuran-1,1'-cyclohexan]-3-one (yield: 99%).

83

Step 3.

At r.t to the mixture of 4'-hydroxy-3H-spiro[2-benzofuran-1,1'-cyclohexan]-3-one (100 mg, 0.46 mmol), triethylamine (192 μL, 1.37 mmol) in methylene chloride (2 mL) was added methanesulfonyl chloride (42.6 μL, 0.55 mmol) with stirring. The mixture was stirred at r.t. overnight, then quenched with water and extracted with ethyl acetate. The extract was washed with water, then brine once; and dried over anhydrous sodium sulfate. After removal of solid, the solution was concentrated to yield 120 mg of 3-oxo-3H-spiro[2-benzofuran-1,1'-cyclohexan]-4'-yl methanesulfonate (yield: 88%).

Step 4.

A mixture of 3-oxo-3H-spiro[2-benzofuran-1,1'-cyclohexan]-4'-yl methanesulfonate (120 mg, 0.40 mmol), sodium azide (263 mg, 4.05 mmol) in DMF (2.0 mL) was maintained at 80° C. overnight. After cooling, it was quenched with sat'd NH4Cl solution, then extracted with ethyl acetate. The extract was washed with water twice, brine once, and dried over anhydrous sodium sulfate. After filtration the filtrate was concentrated to yield 90 mg of 4'-azido-3H-spiro[2-benzofuran-1,1'-cyclohexan]-3-one (yield: 91%).

Step 5.

A mixture of 4'-azido-3H-spiro[2-benzofuran-1,1'-cyclohexan]-3-one (90 mg, 0.36 mmol) in methanol (5 mL) with 10% palladium on charcoal (30 mg) was stirred under hydrogen atmosphere (balloon) for 1 hour. After filtration, the solution was concentrated to yield 88 mg of 4'-amino-3H-spiro[2-benzofuran-1,1'-cyclohexan]-3-one (yield: 90%).

Step 6

The 4'-amino-3H-spiro[2-benzofuran-1,1'-cyclohexan]-3-one was converted to (3S)—N-(3-oxo-3H-spiro[2-benzofuran-1,1'-cyclohexan]-4'-yl)piperidine-3-carboxamide.

Step 7.

A mixture of (3S)—N-(3-oxo-3H-spiro[2-benzofuran-1,1'-cyclohexan]-4'-yl)piperidine-3-carboxamide (11 mg, 0.03 mmol), 3-chloro-2-methylbenzenesulfonyl chloride (6.8 mg, 0.03 mmol), and triethylamine (10.5 μL, 0.075 mmol) in acetonitrile (0.2 mL) was stirred at r.t. for 2 hours. The mixture was purified by flash column to yield 10.2 mg of final product was obtained. Yield: 65%. LCMS: 517.0 (M+H)+; 539.1 (M+Na)+.

Example 105

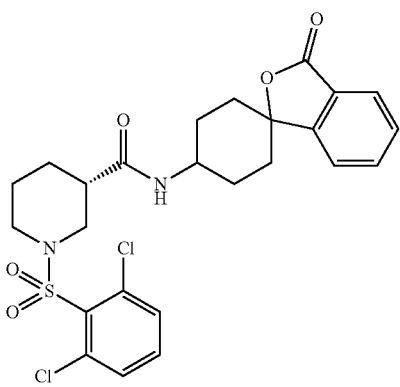

84

(3S)-1-[(2,6-Dichlorophenyl)sulfonyl]-N-(3-oxo-3H-spiro[2-benzofuran-1,1'-cyclohexan]-4'-yl)piperidine-3-carboxamide This compound was prepared using procedures analogous to those of example 104. LCMS: m/z 537.0 (M+H)+; 559.0 (M+Na)+.

Example 106

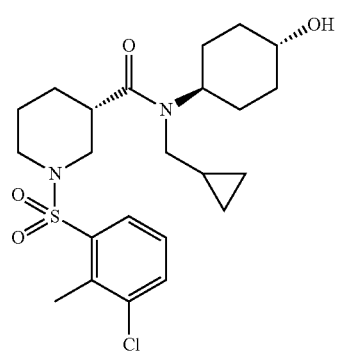

(3S)-1-[(3-Chloro-2-methylphenyl)sulfonyl]-N-(cyclopropylmethyl)-N-(trans-4-hydroxycyclohexyl) piperidine-3-carboxamide Step 1.

After stirring for 20 min, to a suspension of trans-4-aminocyclohexanol hydrochloride (1.0 g, 6.6 mmol), and triethylamine (1.84 mL, 13.2 mmol) in 1,2-dichloroethane (10 mL) was slowly added cyclopropanecarboxaldehyde (0.49 mL, 6.6 mmol) with vigorous stirring. After stirring for another 30 min, to the mixture was added sodium triacetoxyborohydride (2.8 g, 13.2 mmol). The mixture was stirred at r.t overnight, then was quenched with water, and extracted with ethyl acetate. The extract was washed with water.

Step 2.

To the extract was added sodium hydroxide (0.79 g, 20 mmol), followed by 1 eq. of di-tert-butyldicarbonate (1.44 g, 6.6 mmol). The mixture was stirred at r.t. for a weekend, then acidified to pH of about 7 with 1 N HCl solution. The product was extracted with ethyl acetate. The organic solution was washed with 1N HCl solution, water, and brine, successively. Then, the extract was dried over anhydrous sodium sulfate. After filtration, the filtrate was concentrated to yield 0.857 g of tert-butyl (cyclopropylmethyl)(trans-4-hydroxycyclohexyl)carbamate (yield: 48%, 2-step).

Step 3.

A mixture of tert-butyl (cyclopropylmethyl)(trans-4-hydroxycyclohexyl)carbamate (0.857 g, 3.2 mmol) in a solution of methylene chloride (6 mL) and 4.0 M of hydrogen chloride in 1,4-dioxane (3 mL) was stirred at r.t. 2 hours. Concentration yielded 0.658 g of trans-4-[(cyclopropylmethyl)amino] cyclohexanol hydrochloride (100%).

Step 4.

A mixture of trans-4-[(cyclopropylmethyl)amino]cyclohexanol hydrochloride (90 mg, 0.44 mmol), (3S)-1-(tert-butoxycarbonyl)piperidine-3-carboxylic acid (100 mg, 0.44 mmol), benzotriazol-1-yloxytris(dimethylamino)phosphonium hexafluorophosphate (193 mg, 0.44 mmol), and N,N-diisopropylethylamine (190 μL, 1.09 mmol) in methylene chloride (1.5 mL) was stirred at r.t. overnight. The mixture was quenched with 10% citric acid, extracted with ethyl acetate. The extract was washed with 10% citric acid solution, water, and brine successively; then dried over anhydrous sodium sulfate. After filtration, the filtrate was concentrated.

Step 5.

A mixture of above concentrate in methylene chloride (3.0 mL) and 4.0 M of hydrogen chloride in 1,4-dioxane (6 mL) was stirred at r.t. for 3 hours. Then, the mixture was concentrated to yield 0.34 g of (3S)—N-(cyclopropylmethyl)-N-(trans-4-hydroxycyclohexyl)piperidine-3-carboxamide hydrochloride (98%, 2 step, crude).

Step 6.

A mixture of (3S)—N-(cyclopropylmethyl)-N-(trans-4-hydroxycyclohexyl)piperidine-3-carboxamide hydrochloride (10 mg, 0.03 mmol), 3-chloro-2-methylbenzenesulfonyl chloride (7.1 mg, 0.03 mmol), triethylamine (11 µL, 0.08 mmol) in acetonitrile (0.2 mL) was stirred at r.t. for 1 hour, then purified with flash column. 5.1 mg (yield: 34%) final product was obtained. LCMS: m/z 468.9 (M+H)+.

Example 107

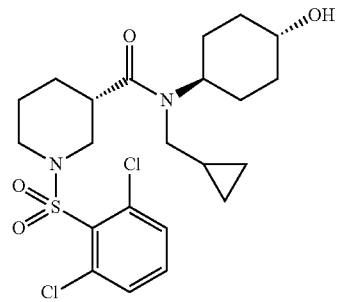

(3S)—N-(Cyclopropylmethyl)-1-[(2,6-dichlorophenyl)sulfonyl]-N-(trans-4-hydroxycyclohexyl)piperidine-3-carboxamide This compound was prepared using analogous procedures to those of example 104.

Example 108

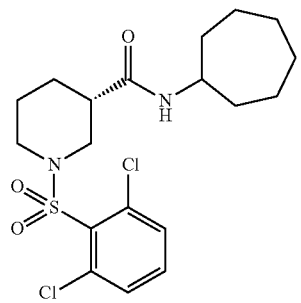

(3S)—N-Cycloheptyl-1-[(2,6-dichlorophenyl)sulfonyl]piperidine-3-carboxamide

This compound was prepared using the similar procedures described in example 1. LCMS: m/z 433.1 (M+H)+; 889.2 (2M+Na)+.

Example 109

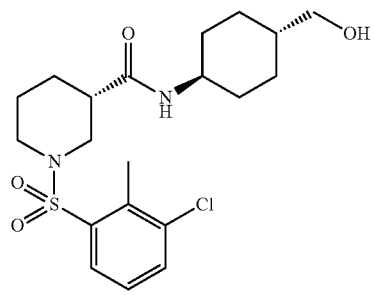

(3S)-1-[(3-Chloro-2-methylphenyl)sulfonyl]-N-[trans-4-(hydroxymethyl)cyclohexyl]piperidine-3-carboxamide Step 1.

A mixture of tert-butyl[trans-4-(hydroxymethyl)cyclohexyl]carbamate (0.2 mg, 0.87 mmol) in methylene chloride (1 mL) and 4.0 M of hydrogen chloride in 1,4-dioxane (1 mL) was stirred at r.t. for 2 hours. The mixture was then concentrated to yield quantitative product: (trans-4-aminocyclohexyl)methanol hydrochloride.

Step 2.

A mixture of (trans-4-aminocyclohexyl)methanol hydrochloride (0.144 g, 0.87 mmol), (3S)-1-(tert-butoxycarbonyl)piperidine-3-carboxylic acid (0.219 g, 0.96 mmol), benzotriazol-1-yloxytris(dimethylamino)phosphonium hexafluorophosphate (0.423 g, 0.96 mmol), and N,N-diisopropylethylamine (0.38 mL, 2.17 mmol) in DMF (3 mL) was stirred at r.t. overnight. The mixture was quenched with 10% citric acid, then extracted with ethyl acetate. The extract was washed with 10% citric acid twice, water and brine once. Then, the extract was dried over anhydrous sodium sulfate. After filtration the filtrated was concentrated and the resulting residue was purified by flash column.

Step 3.

The above intermediate from Step 2 was dissolved in methylene chloride (3.0 mL) and combined with 4.0 M of hydrogen chloride in 1,4-dioxane (6 mL). The mixture was stirred at r.t. for 2 hours. After concentration, 0.42 g (yield: 55%) of (3S)—N-[trans-4-(hydroxymethyl)cyclohexyl]piperidine-3-carboxamide hydrochloride was obtained.

Step 4.

A mixture of (3S)—N-[trans-4-(hydroxymethyl)cyclohexyl]piperidine-3-carboxamide hydrochloride (170 mg, 0.61 mmol), 3-chloro-2-methylbenzenesulfonyl chloride (138 mg, 0.61 mmol), and triethylamine (0.21 mL, 1.54 mmol) in acetonitrile (3 mL) was stirred at r.t. for 2 hours. After removal of solvent, the residue was loaded on flash column with methylene chloride and eluted with ethyl acetate-hexane. 110 mg final product was obtained. (Yield: 41%). LCMS: m/z 429.0 (M+H)+; 879.2 (2M+Na)+.

Example 110

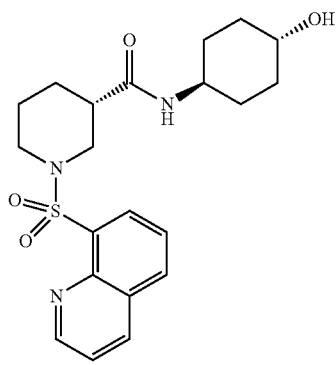

(3R)—N-(trans-4-Hydroxycyclohexyl)-1-(quinolin-8-ylsulfonyl)piperidine-3-carboxamide This compound was prepared using procedures analogous to those of example 15. LCMS: m/z 418.1 (M+H)+; 440.0 (M+Na)+; 857.2 (2M+Na)+.

Example 111

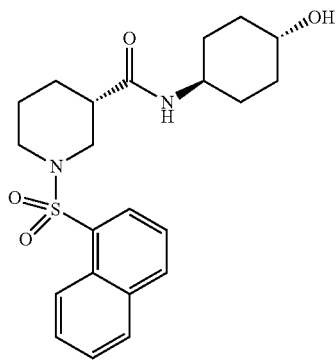

(3S)—N-(trans-4-Hydroxycyclohexyl)-1-(1-naphthylsulfonyl)piperidine-3-carboxamide This compound was prepared using procedures analogous to those of example 15. LCMS: m/z 417.1 (M+H)+; 855.2 (2M+Na)+.

Example 112

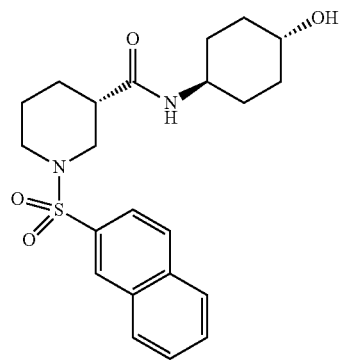

(3S)—N-(trans-4-Hydroxycyclohexyl)-1-(2-naphthylsulfonyl)piperidine-3-carboxamide This compound was prepared using procedures analogous to those of example 15. LCMS: m/z 417.1 (M+H)+; 439.1 (M+Na)+: 855.3 (2M+Na)+.

Example 113

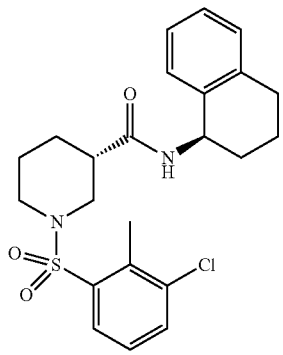

(3S)-1-[(3-Chloro-2-methylphenyl)sulfonyl]-N-[(1R)-1,2,3,4-tetrahydronaphthalen-1-yl]piperidine-3-carboxamide This compound was prepared using procedures analogous to those of example 15. LCMS: m/z 447.1 (M+H)+; 469.0 (M+Na)+.

Example 115

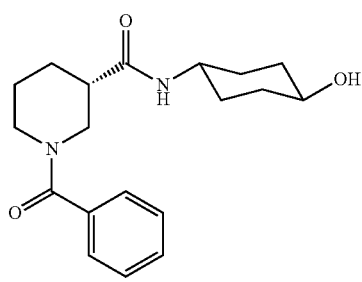

(3S)-1-Benzoyl-N-(4-hydroxycyclohexyl)piperidine-3-carboxamide

This compound was prepared using procedures analogous to those of example 1. LCMS: m/z 331.1 (M+H)+; 353.0 (M+Na)+.

Example 116

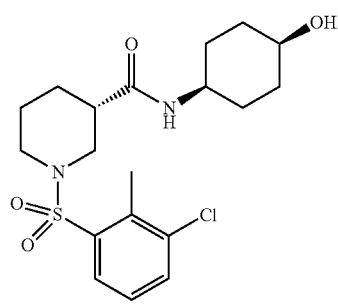

(3S)-1-[(3-Chloro-2-methylphenyl)sulfonyl]-N-(cis-4-hydroxycyclohexyl)piperidine-3-carboxamide This compound was prepared using procedures analogous to those of example 15. LCMS: m/z 415.2 (M+H)+; 851.2 (2M+Na)+.

Example 117

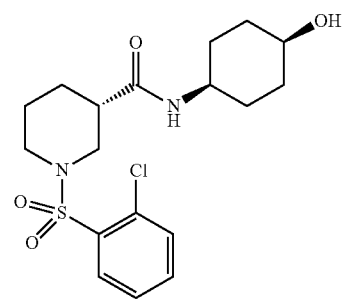

(3S)-1-[(2-Chlorophenyl)sulfonyl]-N-(cis-4-hydroxycyclohexyl)piperidine-3-carboxamide This compound was prepared using procedures analogous to those of example 15. LCMS: m/z 401.1 (M+H)+; 823.3 (2M+Na)+.

Example 118

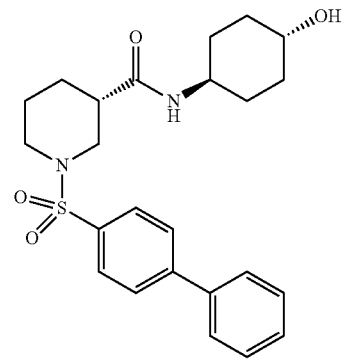

(3S)-1-(Biphenyl-4-ylsulfonyl)-N-(trans-4-hydroxy-cyclohexyl)piperidine-3-carboxamide This compound was prepared using procedures analogous to those of example 15. LCMS: m/z 443.2 (M+H)+.

Example 119

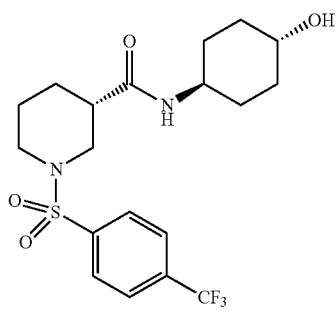

(3S)—N-(trans-4-Hydroxycyclohexyl)-1-{[4-(trifluoromethyl)phenyl]sulfonyl}piperidine-3-carboxamide This compound was prepared using procedures analogous to those of example 15. LCMS: m/z 435.1 (M+H)+; 891.3 (2M+Na)+.

Example 120

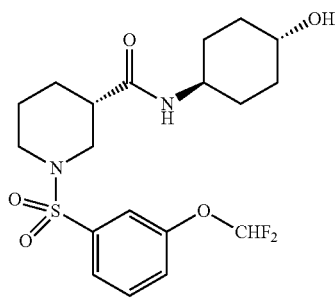

(3S)-1-{[3-(Difluoromethoxy)phenyl]sulfonyl}-N-(trans-4-hydroxycyclohexyl)piperidine-3-carboxamide This compound was prepared using procedures analogous to those of example 15. LCMS: m/z 433.0 (M+H)+; 887.2 (2M+Na)+.

Example 121

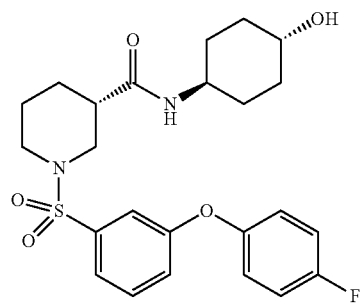

(3S)-1-{[3-(4-Fluorophenoxy)phenyl]sulfonyl}-N-(trans-4-hydroxycyclohexyl)piperidine-3-carboxamide This compound was prepared using procedures analogous to those of example 15. LCMS: m/z 477.1 (M+H)+.

Example 122

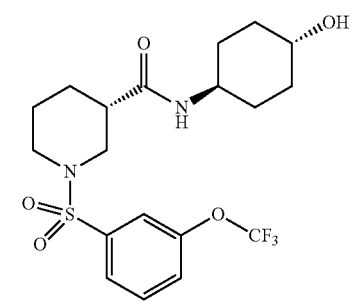

(3S)—N-(trans-4-Hydroxycyclohexyl)-1-{[3-(trifluoromethoxy)phenyl]sulfonyl}-piperidine-3-carboxamide This compound was prepared using procedures analogous to those of example 15. LCMS: m/z 451.0 (M+H)+.

Example 123

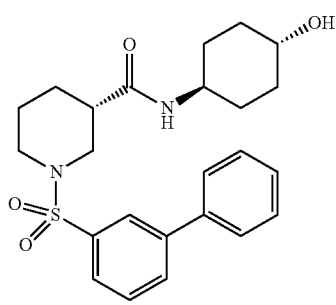

(3S)-1-(Biphenyl-3-ylsulfonyl)-N-(trans-4-hydroxycyclohexyl)piperidine-3-carboxamide This compound was prepared using procedures analogous to those of example 15. LCMS: m/z 443.2 (M+H)+.

Example 124

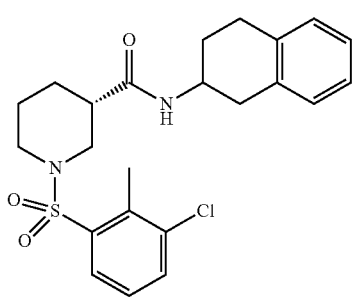

(3S)-1-[(3-Chloro-2-methylphenyl)sulfonyl]-N-(1,2,3,4-tetrahydronaphthalen-2-yl)piperidine-3-carboxamide This compound was prepared using procedures analogous to those of example 15. LCMS: m/z 447.0 (M+H)+; 469.0 (M+Na)+.

Example 125

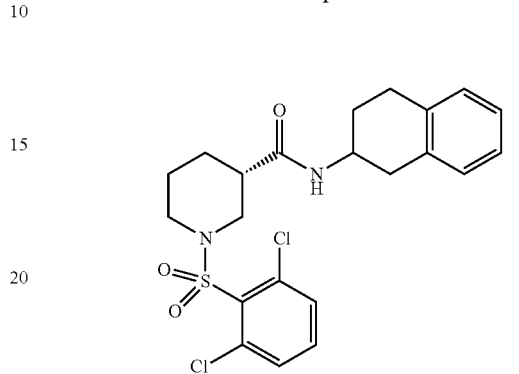

(3S)-1-[(2,6-Dichlorophenyl)sulfonyl]-N-(1,2,3,4-tetrahydronaphthalen-2-yl)piperidine-3-carboxamide This compound was prepared using procedures analogous to those of example 15. LCMS: m/z 467.0 (M+H)+.

Example 126

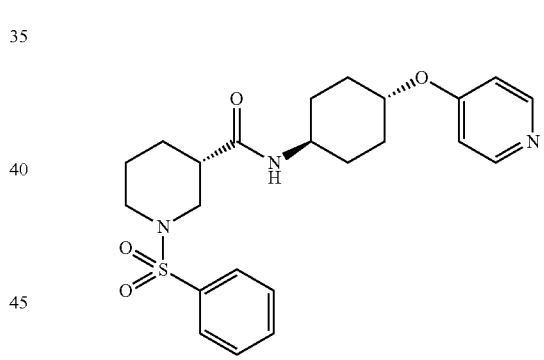

(3S)-1-(Phenylsulfonyl)-N-[trans-4-(pyridin-4-yloxy)cyclohexyl]piperidine-3-carboxamide Step 1.

At 0° C., to a mixture of tert-butyl (cis-4-hydroxycyclohexyl)carbamate (100 mg, 0.5 mmol), 4-pyridinol (106 mg, 1.11 mmol), and triphenylphosphine (292 mg, 1.11 mmol) in tetrahydrofuran (2 mL) was added diethyl azodicarboxylate (176 μL, 1.11 mmol) with stirring. The mixture was stirred at r.t. overnight, then quenched with sat'd NH₄Cl solution, and extracted with ethyl acetate. The extract was washed with water twice, brine once. Then, the extract was dried over Na₂SO₄. After filtration, the filtrate was concentrated to yield tert-butyl[trans-4-(pyridin-4-yloxy)cyclohexyl]carbamate.

Step 2.

A mixture of tert-butyl[trans-4-(pyridin-4-yloxy)cyclohexyl]carbamate in a solution of methylene chloride (1 mL) and 4.0 M of hydrogen chloride in 1,4-dioxane (2 mL) was stirred at r.t for 2 hours. The mixture was concentrated to yield 45% of trans-4-(pyridin-4-yloxy)cyclohexanamine dihydrochloride (2-step).

Step 3.

A mixture of trans-4-(pyridin-4-yloxy)cyclohexanamine dihydrochloride (70 mg, 0.3 mmol), trans-4-(pyridin-4-yloxy)cyclohexanamine dihydrochloride (180 mg, 45%, 0.3 mmol), benzotriazol-1-yloxytris(dimethylamino)phosphonium hexafluorophosphate (142 mg, 0.32 mmol), and N,N-diisopropylethylamine (186 µL, 1.07 mmol) in methylene chloride (1.5 mL) was stirred at r.t. 15, overnight. The mixture was quenched with water, then extracted with ethyl acetate. The extract was washed with sat'd sodium bicarbonate solution twice, water, and brine once. Then, the extract was dried over $Na_2SO_4$. After filtration, the filtrate was concentrated.

Step 4.

A mixture of (3S)—N-[trans-4-(pyridin-4-yloxy)cyclohexyl]piperidine-3-carboxamide dihydrochloride (28 mg, purity: 40%, 0.03 mmol), benzenesulfonyl chloride (6.3 mg, 0.036 mmol), triethylamine (16 µL, 0.12 mmol) in acetonitrile (1 mL) was stirred at r.t. overnight. the mixture was purified with prep. HPLC. 5.9 mg (45%) of final product was obtained. LCMS: m/z 444.1 (M+H)+; 466.1 (M+Na)+.

Example 127

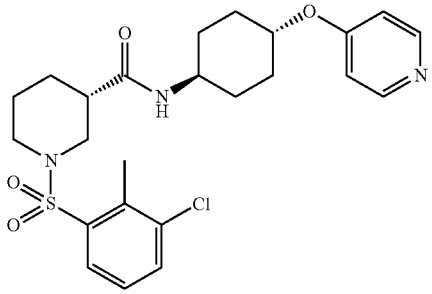

(3S)-1-[(3-Chloro-2-methylphenyl)sulfonyl]-N-[trans-4-(pyridin-4-yloxy)cyclohexyl]piperidine-3-carboxamide This compound was prepared using procedures analogous to those of example 126. LCMS: m/z 492.1 (M+H)+.

Example 128

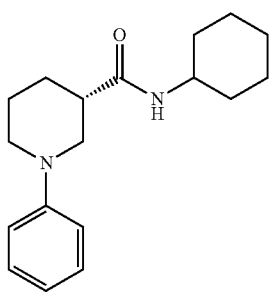

(3S)—N-Cyclohexyl-1-phenylpiperidine-3-carboxamide

Step 1. (3S)—N-Cyclohexylpiperidine-3-carboxamide trifluoroacetate

This compound was prepared by using a procedure that was analogous to that used for the synthesis of example 1, steps 1-2.

Step 2. (3S)—N-Cyclohexyl-1-phenylpiperidine-3-carboxamide

A mixture of bromobenzene (13 µL, 0.00012 mol), (3S)—N-cyclohexylpiperidine-3-carboxamide trifluoroacetate (40 mg, 0.0001 mol), sodium tert-butoxide (28 mg, 0.00030 mol), palladium acetate (0.8 mg, 0.000004 mol) and 2-(di-tert-butylphosphino)biphenyl (1 mg, 0.000004 mol) was vacuumed and charged with nitrogen. To the mixture was added 1,4-dioxane (1 mL, 0.01 mol) and the resulting mixture was refluxed overnight. After cooling, the mixture to ambient temperature the inorganics were filtered and the filtrate was adjusted with TFA to pH=7.0. The crude product was chromatographed by combiflash (ethyl acetate in hexanes: 60%) to afford the desired product. LCMS: m/z 287.3 (M+H)+.

Example 129

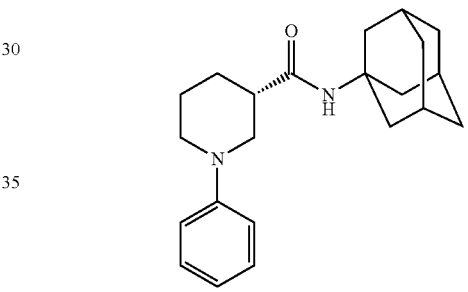

(3S)—N-1-Adamantyl-1-phenylpiperidine-3-carboxamide

Step 1. (3S)-Piperidine-3-carboxylic acid hydrochloride

A mixture of (3S)-1-(tert-butoxycarbonyl)piperidine-3-carboxylic acid (4.0 g, 0.017 mol) in methylene chloride (10 mL, 0.2 mol) and 4.0 M of hydrogen chloride in 1,4-dioxane (30 mL) was stirred at rt for 2 hours. The volatiles were removed in vacuo to afford the desired product in quantitative yield. The crude product was used in the following step without further purification. LCMS: m/z 166.2 (M+H)+.

Step 2. (3S)-1-Phenylpiperidine-3-carboxylic acid

A mixture of bromobenzene (0.82 mL, 0.0078 mol), (3S)-piperidine-3-carboxylic acid hydrochloride (6.5 mmol, 0.0065 mol), sodium tert-butoxide (1.2 g, 0.013 mol), palladium acetate (40 mg, 0.0002 mol) and 2-(di-tert-butylphosphino)biphenyl (60 mg, 0.0002 mol) was degassed under vacuum and charged with nitrogen. To the mixture was added 1,4-dioxane (20 mL, 0.2 mol) and the resulting mixture was refluxed overnight. After cooling the reaction mixture to ambient temperature, the mixture was filtered and the filtrate was adjusted with TFA to pH=3.0 and extracted with EtOAc. The crude product was used in the following step without further purification.

Step 3. (3S)—N-1-Adamantyl-1-phenylpiperidine-3-carboxamide

4-Methylmorpholine (43 µL, 0.00039 mol) was added to a mixture of (3S)-1-phenylpiperidine-3-carboxylic acid (20 mg, 0.0001 mol), tricyclo[3.3.1.1३,7]decane-1-amine (18 mg, 0.00012 mol), (benzotriazol-1-yloxy)tripyrrolidinophosphonium hexafluorophosphate (53.2 mg, 0.000102 mol) or benzotriazol-1-yloxytris(dimethylamino)phosphonium hexafluorophosphate (45.2 mg, 0.000102 mol) in N,N-dimethylformamide (0.5 mL, 0.006 mol). The reaction mixture was stirred at rt for 2 hrs and the crude reaction mixture was purified by prep-LCMS to afford the desired product. LCMS: m/z 339.3 (M+H)+.

Example 130

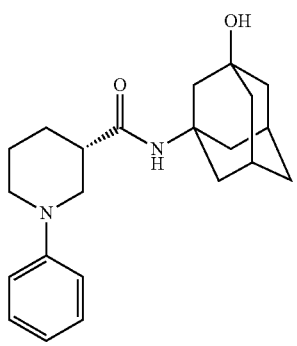

(3S)—N-(3-Hydroxy-1-adamantyl)-1-phenylpiperidine-3-carboxamide

This compound was prepared by using a procedure that was analogous to that used for the synthesis of example 129, steps 1-3. LCMS: m/z 355.3 (M+H)+.

Example 131

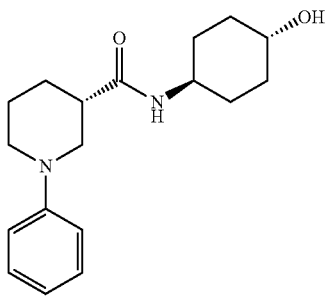

(3S)—N-(trans-4-Hydroxycyclohexyl)-1-phenylpiperidine-3-carboxamide

This compound was prepared by using a procedure that was analogous to that used for the synthesis of example 129, steps 1-3. LCMS: m/z 303.3 (M+H)+.

Example 132

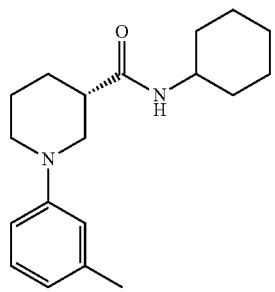

(3S)—N-Cyclohexyl-1-(3-methylphenyl)piperidine-3-carboxamide

This compound was prepared by using a procedure that was analogous to that used for the synthesis of example 128, steps 1 and 2. LCMS: m/z 301.3 (M+H)+.

Example 133

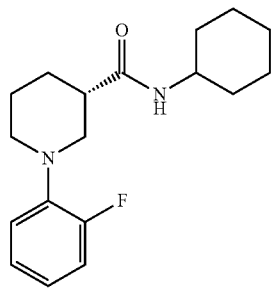

(3S)—N-Cyclohexyl-1-(2-fluorophenyl)piperidine-3-carboxamide

This compound was prepared by using a procedure that was analogous to that used for the synthesis of example 128, steps 1 and 2. LCMS: m/z 305.3 (M+H)+.

Example 134

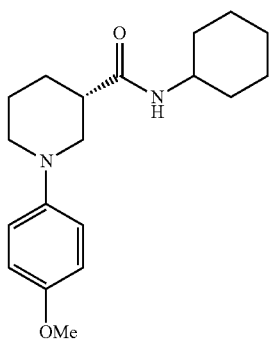

(3S)—N-Cyclohexyl-1-(4-methoxyphenyl)piperidine-3-carboxamide

This compound was prepared by using a procedure that was analogous to that used for the synthesis of example 128, steps 1 and 2. LCMS: m/z 317.3 (M+H)+.

Example 135

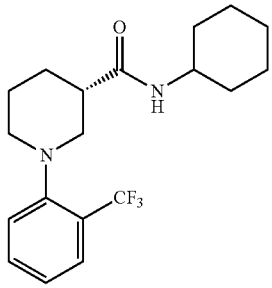

(3S)—N-Cyclohexyl-1-[2-(trifluoromethyl)phenyl]piperidine-3-carboxamide

This compound was prepared by using a procedure that was analogous to that used for the synthesis of example 128, steps 1 and 2. LCMS: m/z 355.3 (M+H)+.

Example 136

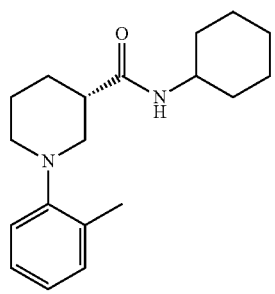

(3S)—N-Cyclohexyl-1-(2-methylphenyl)piperidine-3-carboxamide

This compound was prepared by using a procedure that was analogous to that used for the synthesis of example 128, steps 1 and 2. LCMS: m/z 301.3 (M+H)+.

Example 137

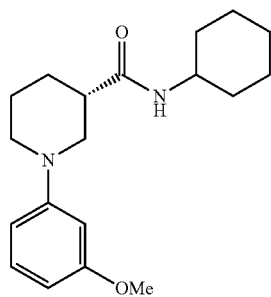

101

(3S)—N-Cyclohexyl-1-(3-methoxyphenyl)piperidine-3-carboxamide

This compound was prepared by using a procedure that was analogous to that used for the synthesis of example 128, steps 1 and 2. LCMS: m/z 317.2 (M+H)+.

Example 138

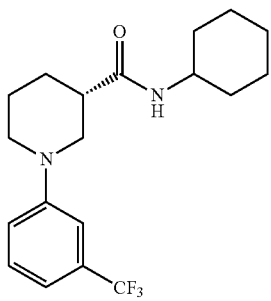

(3S)—N-Cyclohexyl-1-[3-(trifluoromethyl)phenyl]piperidine-3-carboxamide

This compound was prepared by using a procedure that was analogous to that used for the synthesis of example 128, steps 1 and 2. LCMS: m/z 355.2 (M+H)+.

Example 139

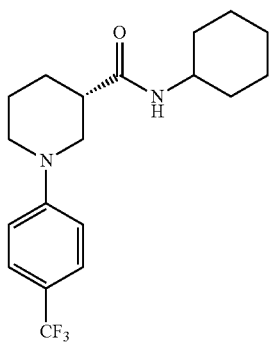

102

(3S)—N-Cyclohexyl-1-[4-(trifluoromethyl)phenyl]piperidine-3-carboxamide

This compound was prepared by using a procedure that was analogous to that used for the synthesis of example 128, steps 1 and 2. LCMS: m/z 355.2 (M+H)+.

Example 140

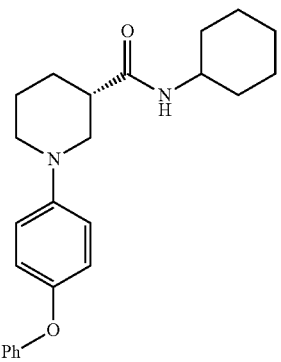

(3S)—N-Cyclohexyl-1-(4-phenoxyphenyl)piperidine-3-carboxamide

This compound was prepared by using a procedure that was analogous to that used for the synthesis of example 128, steps 1 and 2. LCMS: m/z 379.3 (M+H)+.

Example 141

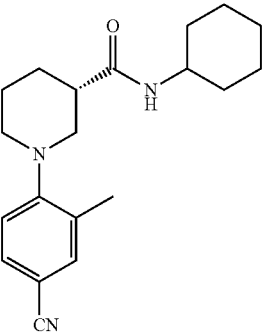

(3S)-1-(4-Cyano-2-methylphenyl)-N-cyclohexylpiperidine-3-carboxamide

This compound was prepared by using a procedure that was analogous to that used for the synthesis of example 128, steps 1 and 2. LCMS: m/z 326.3 (M+H)+.

Example 142

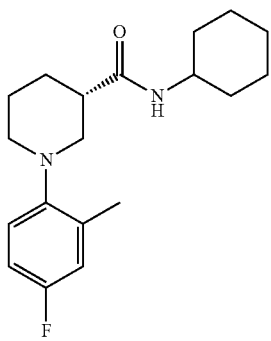

(3S)—N-Cyclohexyl-1-(4-fluoro-2-methylphenyl)piperidine-3-carboxamide

This compound was prepared by using a procedure that was analogous to that used for the synthesis of example 128, steps 1 and 2. LCMS: m/z 319.2 (M+H)+.

Example 143

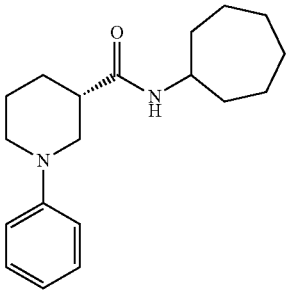

(3S)—N-Cycloheptyl-1-phenylpiperidine-3-carboxamide

This compound was prepared by using a procedure that was analogous to that used for the synthesis of example 129, steps 1-3. LCMS: m/z 301.2 (M+H)+.

Example 144

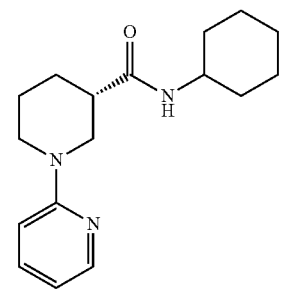

(3S)—N-Cyclohexyl-1-pyridin-2-ylpiperidine-3-carboxamide

This compound was prepared by using a procedure that was analogous to that used for the synthesis of example 128, steps 1 and 2.

Example 145

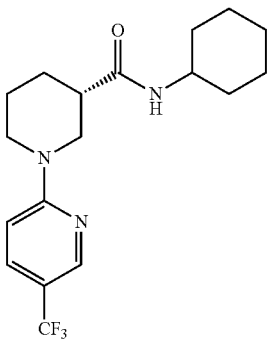

105

(3S)—N-Cyclohexyl-1-[5-(trifluoromethyl)pyridin-2-yl]piperidine-3-carboxamide

This compound was prepared by using a procedure that was analogous to that used for the synthesis of example 128, steps 1 and 2. LCMS: m/z 356.3 (M+H)+.

Example 146

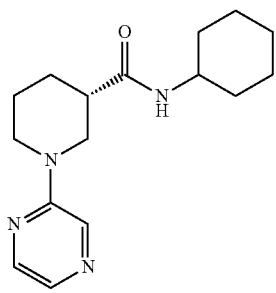

(3S)—N-Cyclohexyl-1-pyrazin-2-ylpiperidine-3-carboxamide

This compound was prepared by using a procedure that was analogous to that used for the synthesis of example 128, steps 1 and 2. LCMS: m/z 289.2 (M+H)+.

Example 147

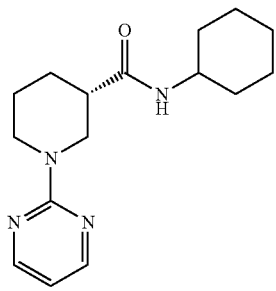

106

(3S)—N-Cyclohexyl-1-pyrimidin-2-ylpiperidine-3-carboxamide

This compound was prepared by using a procedure that was analogous to that used for the synthesis of example 128, steps 1 and 2. LCMS: m/z 289.2 (M+H)+.

Example 148

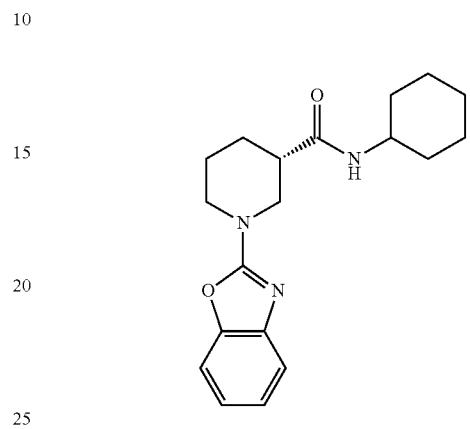

(3S)-1-(1,3-Benzoxazol-2-yl)-N-cyclohexylpiperidine-3-carboxamide

This compound was prepared by using a procedure that was analogous to that used for the synthesis of example 128, steps 1 and 2. LCMS: m/z 328.2 (M+H)+.

Example 149

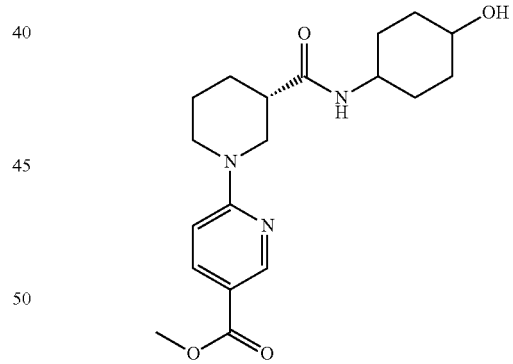

Methyl 6-((3S)-3-{[(4-hydroxycyclohexyl)amino]carbonyl}piperidin-1-yl)nicotinate A mixture of (3S)—N-(4-hydroxycyclohexyl)piperidine-3-carboxamide hydrochloride (19.7 mg, 0.0000750 mol, prepared by using a procedure that was analogous to that described for the synthesis of example 1, steps 1 and 2), methyl 6-chloronicotinate (15.4 mg, 0.0000900 mol) and N,N-diisopropylethylamine (37.5 μL, 0.000216 mol) in N,N-dimethylformamide (0.75 mL, 0.0097 mol) was irradiated under microwave at 200° C. for 15 min. The mixture was adjusted with TFA to pH=2.0 and was diluted with methanol (0.8 mL). The resulting solution was purified by prep.—HPLC to give the desired product. LCMS: m/z 362.2 (M+H)$^+$.

Example 150

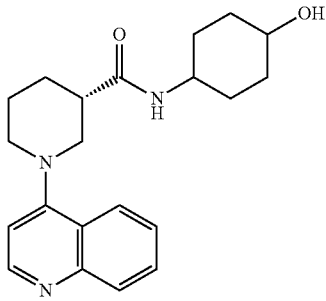

(3S)—N-(4-Hydroxycyclohexyl)-1-quinolin-4-ylpiperidine-3-carboxamide

This compound was prepared by using a procedure that was analogous to that described for the synthesis of example 149. LCMS: m/z 354.2 (M+H)$^+$.

Example 151

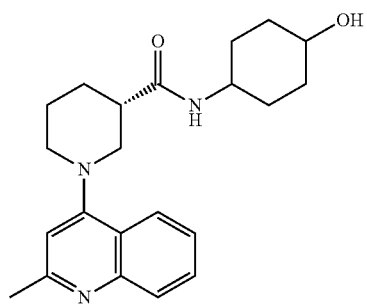

(3S)—N-(4-Hydroxycyclohexyl)-1-(2-methylquinolin-4-yl)piperidine-3-carboxamide

This compound was prepared by using a procedure that was analogous to that described for the synthesis of example 149. LCMS: m/z 368.2 (M+H)$^+$.

Example 152

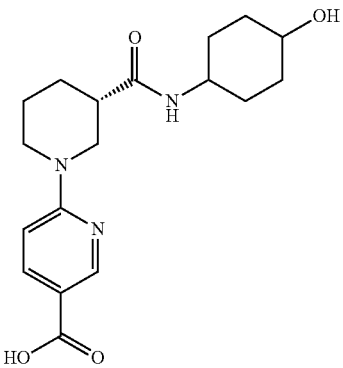

6-((3S)-3-{[(4-Hydroxycyclohexyl)amino]carbonyl}piperidin-1-yl)nicotinic acid

This compound was prepared by using a procedure that was analogous to that described for the synthesis of example 149. LCMS: m/z 348.2 (M+H)$^+$.

Example 153

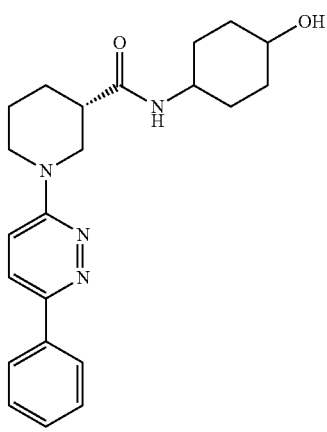

(3S)—N-(4-Hydroxycyclohexyl)-1-(6-phenylpyridazin-3-yl)piperidine-3-carboxamide

This compound was prepared by using a procedure that was analogous to that described for the synthesis of example 149. LCMS: m/z 381.2 (M+H)$^+$.

Example 154

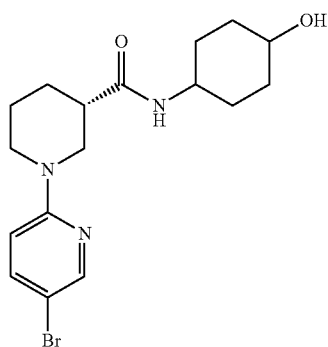

(3S)-1-(5-Bromopyridin-2-yl)-N-(4-hydroxycyclohexyl)piperidine-3-carboxamide

This compound was prepared by using a procedure that was analogous to that described for the synthesis of example 149. LCMS: m/z 382.1/384.2 (M+H)$^+$.

Example 155

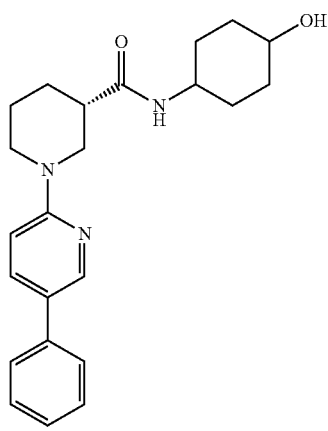

(3S)—N-(4-Hydroxycyclohexyl)-1-(5-phenylpyridin-2-yl)piperidine-3-carboxamide

Sodium carbonate (21.2 mg, 0.000200 mol) in water (0.10 mL) was added to a mixture of (3S)-1-(5-bromopyridin-2-yl)-N-(4-hydroxycyclohexyl)piperidine-3-carboxamide (38.2 mg, 0.000100 mol, prepared as example 154), phenylboronic acid (14.6 mg, 0.000120 mol) and tetrakis(triphenylphosphine)palladium(0) (3.5 mg, 0.0000030 mol) in toluene (200.0 μL, 0.001878 mol) and ethanol (100.0 μL, 0.001713 mol). The resulting mixture was irradiated with microwaves at 150° C. for 20 min. Ethyl acetate (5 mL) was added and the mixture was washed with water and brine. The organic layer was dried over Na$_2$SO$_4$, filtered, and concentrated under reduced pressure. The residue was dissolved in DMF and purified by prep.—HPLC to give the desired product. LCMS: m/z 380.2 (M+H)$^+$.

Example 156

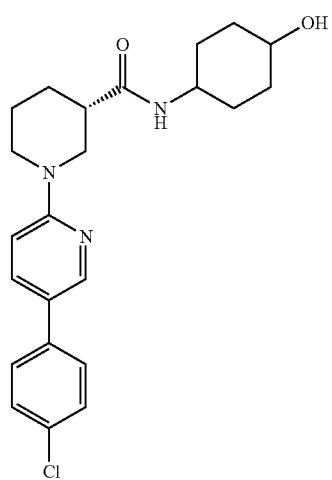

(3S)-1-[5-(4-Chlorophenyl)pyridin-2-yl]-N-(4-hydroxycyclohexyl)piperidine-3-carboxamide This compound was prepared by using a procedure that was analogous to that described for the synthesis of example 155. LCMS: m/z 414.2/416.2 (M+H)$^+$.

Example 157

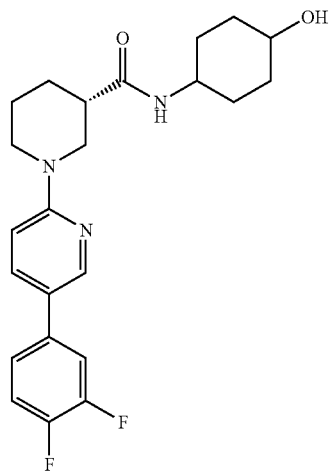

(3S)-1-[5-(3,4-Difluorophenyl)pyridin-2-yl]-N-(4-hydroxycyclohexyl)piperidine-3-carboxamide This compound was prepared by using a procedure that was analogous to that described for the synthesis of example 155. LCMS: m/z 416.2 (M+H)$^+$.

Example 158

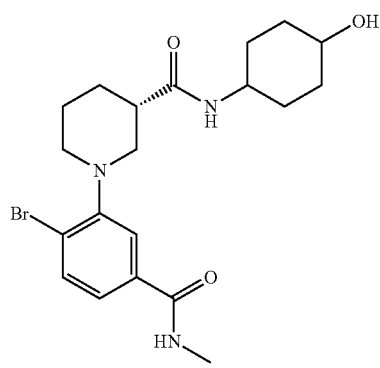

(3S)-1-{2-Bromo-5-[(methylamino)carbonyl]phenyl}-N-(4-hydroxycyclohexyl)piperidine-3-carboxamide This compound was prepared by using a procedure that was analogous to that described for the synthesis of example 128. LCMS: m/z 439.1 (M+H)$^+$.

Example 159

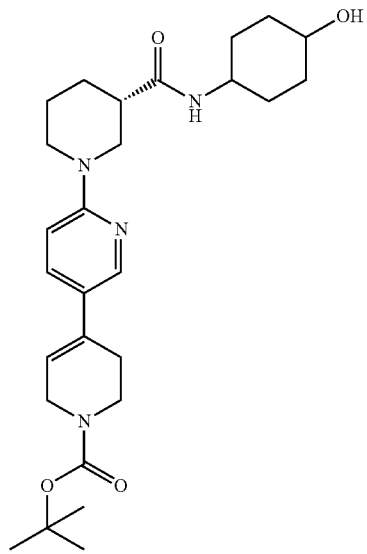

tert-Butyl 6-((3S)-3-{[(4-hydroxycyclohexyl)amino]carbonyl}piperidin-1-yl)-3',6'-dihydro-3,4'-bipyridine-1'(2'H)-carboxylate This compound was prepared by using a procedure that was analogous to that described for the synthesis of example 155. LCMS: m/z 485.3 (M+H)$^+$.

Example 160

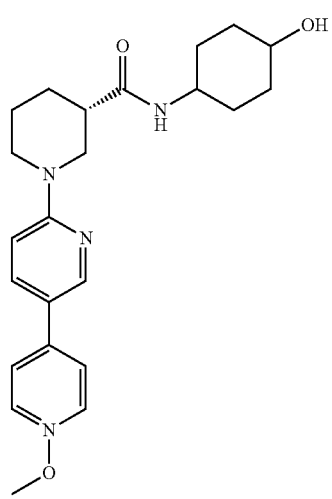

(3S)—N-(4-Hydroxycyclohexyl)-1-[5-(4-methoxyphenyl)pyridin-2-yl]piperidine-3-carboxamide This compound was prepared by using a procedure that was analogous to that described for the synthesis of example 155. LCMS: m/z 410.2 (M+H)$^+$.

Example 161

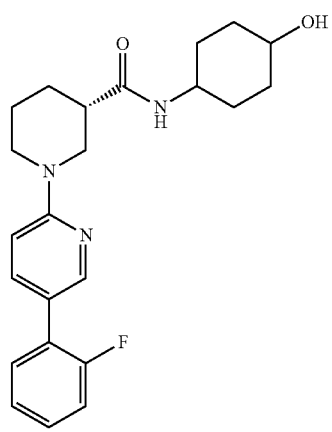

(3S)-1-[5-(2-Fluorophenyl)pyridin-2-yl]-N-(4-hydroxycyclohexyl)piperidine-3-carboxamide This compound was prepared by using a procedure that was analogous to that described for the synthesis of example 155. LCMS: m/z 398.2 (M+H)+.

Example 162

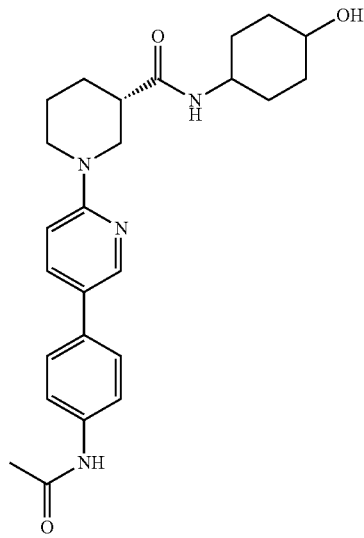

(3S)-1-{5-[4-(Acetylamino)phenyl]pyridin-2-yl}-N-(4-hydroxycyclohexyl)piperidine-3-carboxamide This compound was prepared by using a procedure that was analogous to that described for the synthesis of example 155. LCMS: m/z 437.2 (M+H)+.

Example 163

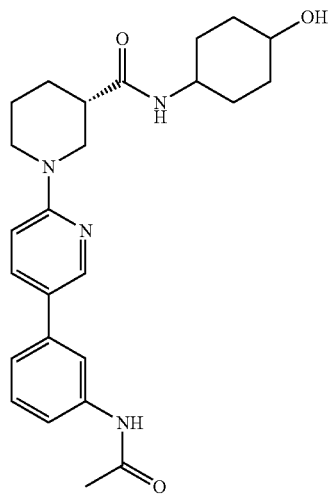

(3S)-1-{5-[3-(Acetylamino)phenyl]pyridin-2-yl}-N-(4-hydroxycyclohexyl)piperidine-3-carboxamide This compound was prepared by using a procedure that was analogous to that described for the synthesis of example 155. LCMS: m/z 437.2 (M+H)+.

Example 164

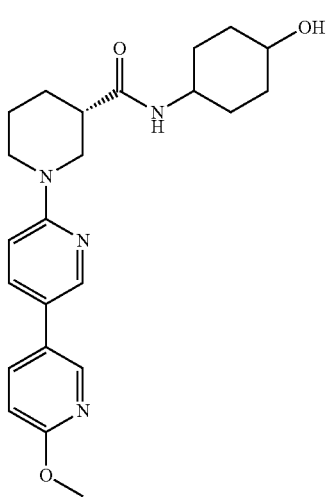

(3S)—N-(4-Hydroxycyclohexyl)-1-(6'-methoxy-3,3'-bipyridin-6-yl)piperidine-3-carboxamide This compound was prepared by using a procedure that was analogous to that described for the synthesis of example 155. LCMS: m/z 411.2 (M+H)+.

Example 165

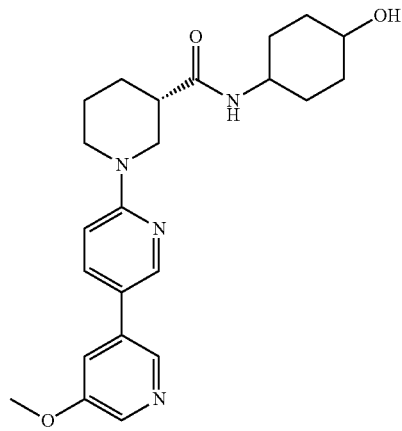

(3S)—N-(4-Hydroxycyclohexyl)-1-(5'-methoxy-3,3'-bipyridin-6-yl)piperidine-3-carboxamide This compound was prepared by using a procedure that was analogous to that described for the synthesis of example 155. LCMS: m/z 411.2 (M+H)$^+$.

Example 166

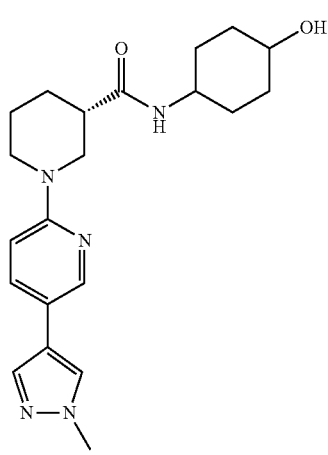

(3S)—N-(4-Hydroxycyclohexyl)-1-[5-(1-methyl-1H-pyrazol-4-yl)pyridin-2-yl]piperidine-3-carboxamide This compound was prepared by using a procedure that was analogous to that described for the synthesis of example 155. LCMS: m/z 384.2 (M+H)$^+$.

Example 167

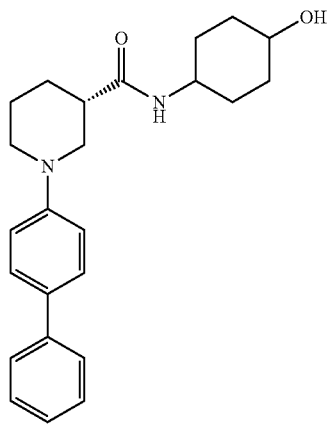

(3S)-1-Biphenyl-4-yl-N-(4-hydroxycyclohexyl)piperidine-3-carboxamide

This compound was prepared by using a procedure that was analogous to that described for the synthesis of example 155. LCMS: m/z 379.2 (M+H)$^+$.

Example 168

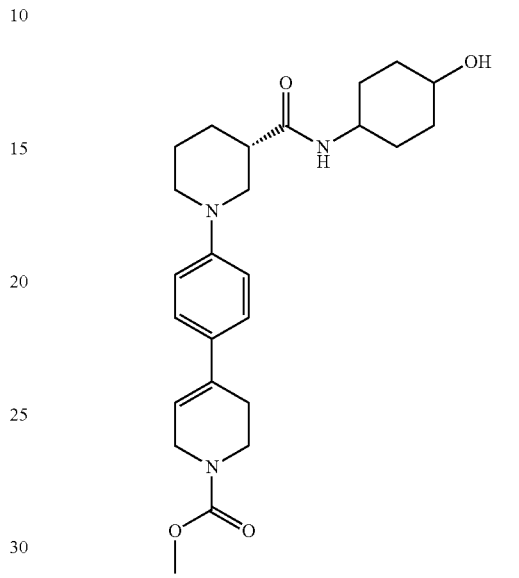

Methyl 4-[4-((3S)-3-{[(4-hydroxycyclohexyl)amino]carbonyl}piperidin-1-yl)phenyl]-3,6-dihydropyridine-1(2H)-carboxylate This compound was prepared by using a procedure that was analogous to that described for the synthesis of example 155. LCMS: m/z 442.2 (M+H)$^+$.

Example 169

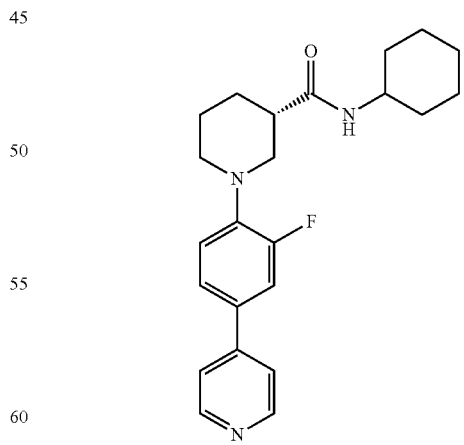

(3S)—N-cyclohexyl-1-(2-fluoro-4-pyridin-4-ylphenyl)piperidine-3-carboxamide

Step 1. 4-(4-Bromo-3-fluorophenyl)pyridine

Sodium carbonate (0.86 g, 0.0081 mol) in water (3.0 mL, 0.17 mol) was added to a mixture of 4-pyridinylboronic acid (0.5 g, 0.004 mol), 1-bromo-2-fluoro-4-iodobenzene (1.5 g, 0.0049 mol), and tetrakis(triphenylphosphine)palladium(0) (0.02 g, 0.00002 mol) in toluene (6.0 mL, 0.056 mol) and ethanol (3.0 mL, 0.051 mol). The resulting mixture was irradiated by microwave at 120° C. for 30 min. The reaction mixture was extracted with EtOAc and the combined organic layers were dried over $Na_2SO_4$, filtered, and concented in-vacuo. The residue was purified by CombiFlash (EtOAc in hexanes: 40%) to afford the desired product.

Step 2. Ethyl (3S)-1-(2-fluoro-4-pyridin-4-ylphenyl)piperidine-3-carboxylate

A mixture of 4-(4-bromo-3-fluorophenyl)pyridine (190 mg, 0.00075 mol), ethyl (3S)-piperidine-3-carboxylate hydrochloride (180 mg, 0.00090 mol), sodium tert-butoxide (140 mg, 0.0015, mol), palladium acetate (5 mg, 0.00002 mol) and 2-(di-tert-butylphosphino)biphenyl (7 mg, 0.00002 mol) was evacuated and charged with nitrogen and 1,4-dioxane (5 mL, 0.06 mol). The resulting mixture was refluxed overnight. After cooling to ambient temperature, the mixture was filtered and the filtrate was adjusted with TFA to pH=7.0 and purified by CombiFlash (ethyl acetate in hexanes: 60%) to afford the desired product. LCMS: m/z 329.2 (M+H)$^+$.

Step 3. (3S)-1-(2-Fluoro-4-pyridin-4-ylphenyl)piperidine-3-carboxylic acid

Lithium hydroxide, monohydrate (0.013 g, 0.00030 mol) was added to ethyl (3S)-1-(2-fluoro-4-pyridin-4-ylphenyl)piperidine-3-carboxylate (0.050 g, 0.00015 mol) in methanol (0.5 mL, 0.01 mol), tetrahydrofuran (0.5 mL, 0.006 mol) and water (0.5 mL, 0.03 mol). The mixture was irradiated under microwave at 100° C. for 30 min. The reaction mixture was diluted with water and adjusted to pH=5 by adding 1N HCl. The volatiles were removed in-vacuo to afford the desired product and LiCl, which was used as a mixture in the next step.

Step 4. (3S)—N-Cyclohexyl-1-(2-fluoro-4-pyridin-4-ylphenyl)piperidine-3-carboxamide The title compound was prepared by using a procedure that was analogous to that described for the synthesis of example 129, step 3. LCMS: m/z 382.2 (M+H)$^+$.

Example 170

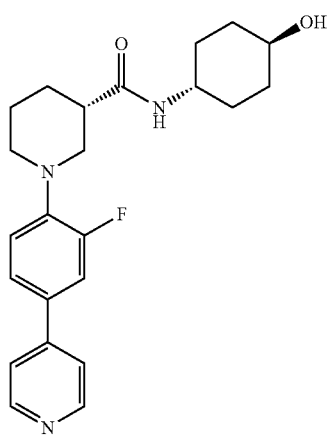

(3S)-1-(2-Fluoro-4-pyridin-4-ylphenyl)-N-(trans-4-hydroxycyclohexyl)piperidine-3-carboxamide This compound was prepared by using a procedure that was analogous to that described for the synthesis of example 169, steps 1-4. LCMS: m/z 398.2 (M+H)$^+$.

Example 171

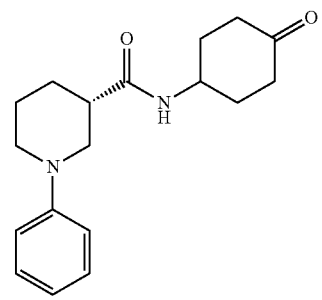

(3S)—N-(4-Oxocyclohexyl)-1-phenylpiperidine-3-carboxamide

A solution of ethyl (3S)-piperidine-3-carboxylate hydrochloride (0.1 g, 0.0005 mol), bromobenzene (0.16 g, 0.0010 mol) and potassium tert-butoxide (0.12 g, 0.0010 mol) in dimethyl sulfoxide (4 mL, 0.06 mol) was heated at 200° C. for 10 min. under microwave irradiation. The crude (3S)-1-phenylpiperidine-3-carboxylic acid was subjected to BOP-mediated coupling by using a procedure that was analogous to that described for the synthesis of example 129, step 3. LCMS: m/z 301.2 (M+H)$^+$.

Example 172

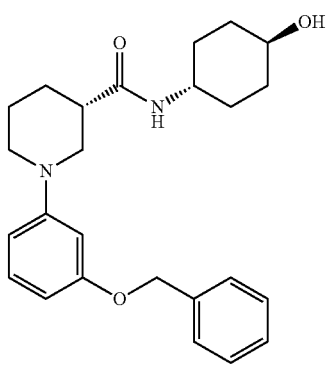

(3S)-1-[3-(Benzyloxy)phenyl]-N-(trans-4-hydroxy-cyclohexyl)piperidine-3-carboxamide This compound was prepared by using a procedure that was analogous to that described for the synthesis of example 128, steps 1 and 2. LCMS: m/z 409.2 (M+H)$^+$.

Example 173

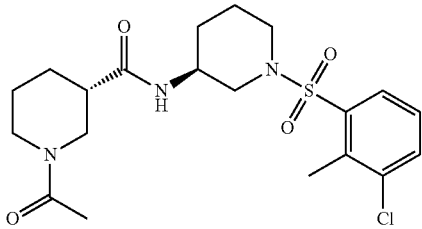

(3S)-1-Acetyl-N-(3S)-1-[(3-chloro-2-methylphenyl)sulfonyl]piperidin-3-ylpiperidine-3-carboxamide Step 1. tert-Butyl {(3S)-1-[3-chloro-2-methylphenyl)sulfonyl]piperidin-3-yl}carbamate A solution of 3-chloro-2-methylbenzenesulfonyl chloride (0.75 g, 0.0033 mol) in 5 mL of acetonitrile was added to a solution of tert-butyl (3S)-piperidin-3-ylcarbamate (0.67 g, 0.0033 mol) in 5 mL of acetonitrile at 0° C. After stirring at rt for 1.5 h the reaction mixture was filtered and concentrated to afford the desired product, which was used in the next step without further purification.

Step 2. tert-butyl (3S)-3-[({(3S)-1-[(3-chloro-2-methylphenyl)sulfonyl]piperidin-3-yl}amino) carbonyl]piperidine-1-carboxylate tert-Butyl {(3S)-1-[(3-chloro-2-methylphenyl)sulfonyl]piperidin-3-yl}carbamate (58.34 mg, 0.0001500 mol) was treated with 4.0 M of hydrogen chloride in 1,4-dioxane (1.0 mL) at rt for 30 min. The solvent was evaporated under reduced pressure and the residue was dissolved in DMF (1.0 mL) and to this was added benzotriazol-1-yloxytris(dimethylamino)phosphonium hexafluorophosphate (69.6 mg, 0.000157 mol), 4-methylmorpholine (100.0 uL, 0.0009096 mol), and (3S)-1-(tert-butoxycarbonyl)piperidine-3-carboxylic acid (34.4 mg, 0.000150 mol) at rt. After stirring for 1 h, the reaction mixture was diluted with ethyl acetate (5 mL) and washed with NaHCO$_3$ (7.5%, 3×2 mL) and brine (3×20 mL). The organic layer was dried over Na$_2$SO$_4$, filtered, and concentrated under reduced pressure to give the desired product which was used directly in the next step without further purification.

Step 3. (3S)-1-Acetyl-N-{(3S)-1-[(3-chloro-2-methylphenyl)sulfonyl]piperidin-3-yl}piperidine-3-carboxamide tert-Butyl (3S)-3-[((3S)-1-[(3-chloro-2-methylphenyl)sulfonyl]piperidin-3-ylamino)-carbonyl]piperidine-1-carboxylate (10.0 mg, 200 μmol) was treated with 4.0 M of hydrogen chloride in 1,4-dioxane (0.5 mL) at rt for 1 h. The volatiles were removed in-vacuo and the residue was dissolved in acetonitrile (0.8 mL) and was treated with diisopropylethylamine (20.0 μL) and acetyl chloride (5.0 μL). The crude reaction mixture was diluted with MeOH (1.3 mL) and was adjusted to a pH of 2 using TFA and was purified by prep-HPLC to give the desired product. LCMS: (M+H)$^+$=442.1/444.1.

Example 174

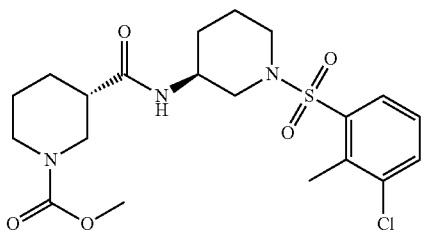

Methyl (3S)-3-[((3S)-1-[(3-chloro-2-methylphenyl)sulfonyl]piperidin-3-ylamino)carbonyl]piperidine-1-carboxylate This compound was prepared by using a procedure that was analogous to that described for the synthesis of example 173. LCMS: (M+H)$^+$=458.1/460.1.

Example 175

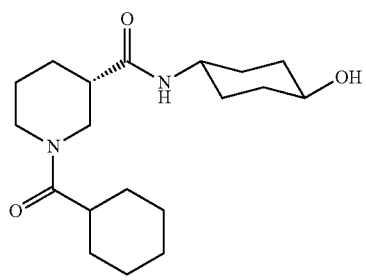

(3S)-1-(Cyclohexylcarbonyl)-N-(4-hydroxycyclohexyl)piperidine-3-carboxamide

This compound was prepared by using a procedure that was analogous to that described for the synthesis of example 1. LCMS: (M+H)$^+$=337.2; (M+Na)$^+$=359.2.

Example 176

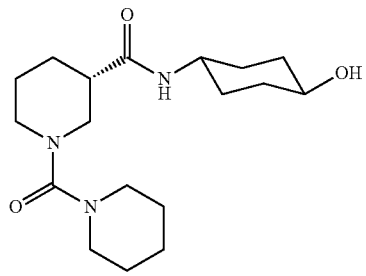

(3S)—N-(4-hydroxycyclohexyl)-1-(piperidin-1-yl-carbonyl)piperidine-3-carboxamide This compound was prepared by using a procedure that was analogous to that described for the synthesis of example 1. LCMS: (M+H)$^+$=338.1; (M+Na)$^+$=360.1.

Example 177

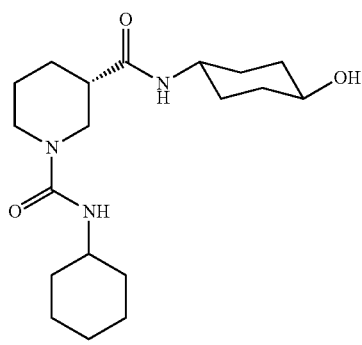

(3S)—N(1)-cyclohexyl-N(3)-(4-hydroxycyclohexyl)piperidine-1,3-dicarboxamide

This compound was prepared by using a procedure that was analogous to that described for the synthesis of example 1 starting from cyclohexylisocyantate and (3S)—N-(4-hydroxycyclohexyl)piperidine-3-carboxamide. LCMS: (M+H)$^+$=352.2; (M+Na)$^+$=374.2.

Example 178

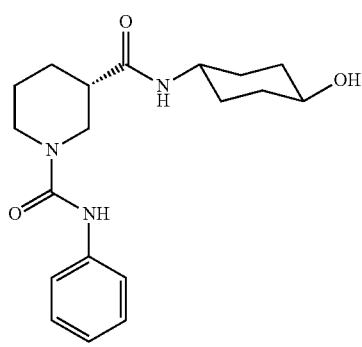

(3S)—N(3)-(4-Hydroxycyclohexyl)-N(1)-phenylpiperidine-1,3-dicarboxamide

This compound was prepared by using a procedure that was analogous to that described for the synthesis of example 177. LCMS: (M+H)$^+$=346.1; (M+Na)$^+$=368.1.

Example 179

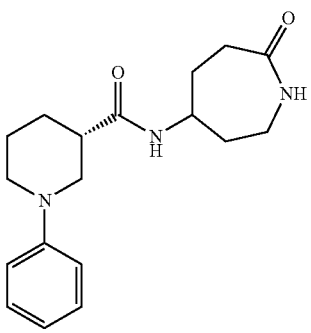

(3S)—N-(7-oxoazepan-4-yl)-1-phenylpiperidine-3-carboxamide

To a solution of (3S)—N-(4-oxocyclohexyl)-1-phenylpiperidine-3-carboxamide (10 mg, 0.00003 mol, prepared as example 171) in concentrated aqueous HCl (0.5 mL), was added sodium azide (2.27 mg, 0.0000350 mol) in small portions over 3 minutes with slow agitation. The temperature was slowly increased to 50° C. The reaction temperature was maintained at 50° C. for 8.5 h and then poured into 50 g of crushed ice and water. The solution was basified with cold 50% NaOH and the resulting solution was extracted with EtOAc(×3). The EtOAc extracts were combined, dried over MgSO$_4$, filtered and evaporated to yield the crude product, which was purified by prep-HPLC. LCMS: (M+H)$^+$=316.2.

Example 180

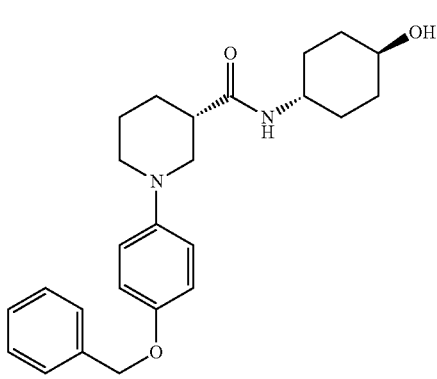

123

(3S)-1-[4-(Benzyloxy)phenyl]-N-(4-hydroxycyclohexyl)piperidine-3-carboxamide

This compound was prepared by using a procedure that was analogous to that described for the synthesis of example 128, steps 1 and 2. LCMS: m/z 409.2 (M+H)$^+$.

Example 181

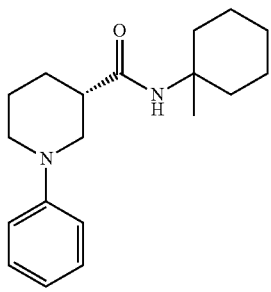

(3S)—N-(1-Methylcyclohexyl)-1-phenylpiperidine-3-carboxamide

This compound was prepared by using a procedure that was analogous to that described for the synthesis of example 128, steps 1 and 2. LCMS: m/z 301.1 (M+H)$^+$.

Example 182

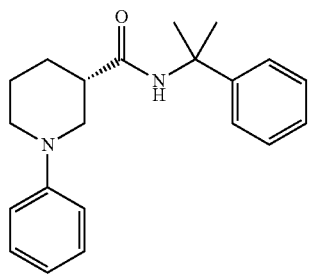

124

(3S)—N-(1-Methyl-1-phenylethyl)-1-phenylpiperidine-3-carboxamide

This compound was prepared by using a procedure that was analogous to that described for the synthesis of example 128, steps 1 and 2. LCMS: m/z 323.2 (M+H)$^+$.

Example 183

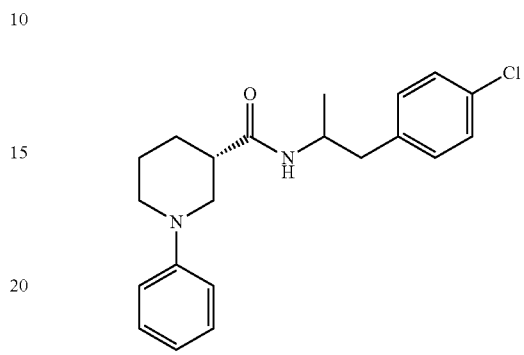

(3S)—N-[2-(4-Chlorophenyl)-1-methylethyl]-1-phenylpiperidine-3-carboxamide

This compound was prepared by using a procedure that was analogous to that described for the synthesis of example 128, steps 1 and 2. LCMS: m/z 357.2/359.2 (M+H)$^+$.

Example A

Enzymatic Assay of 11βHSD1

All in vitro assays were performed with clarified lysates as the source of 11βHSD1 activity. HEK-293 transient transfectants expressing an epitope-tagged version of full-length human 11βHSD1 were harvested by centrifugation. Roughly $2 \times 10^7$ cells were resuspended in 40 mL of lysis buffer (25 mM Tris-HCl, pH 7.5, 0.1M NaCl, 1 mM MgCl$_2$ and 250 mM sucrose) and lysed in a microfluidizer. Lysates were clarified by centrifugation and the supernatants were aliquoted and frozen.

Inhibition of 11βHSD1 by test compounds was assessed in vitro by a Scintillation Proximity Assay (SPA). Dry test compounds were dissolved at 5 mM in DMSO. These were diluted in DMSO to suitable concentrations for the SPA assay. 0.8 μL of 2-fold serial dilutions of compounds were dotted on 384 well plates in DMSO such that 3 logs of compound concentration were covered. 20 μL of clarified lysate was added to each well. Reactions were initiated by addition of 20 μL of substrate-cofactor mix in assay buffer (25 mM Tris-HCl, pH 7.5, 0.1M NaCl, 1 mM MgCl$_2$) to final concentrations of 400 μM NADPH, 25 nM $^3$H-cortisone and 0.007% Triton X-100. Plates were incubated at 37° C. for one hour. Reactions were quenched by addition of 40 μL of anti-mouse coated SPA beads that had been pre-incubated with 10 μM carbenoxolone and a cortisol-specific monoclonal antibody. Quenched plates were incubated for a minimum of 30 minutes at RT prior to reading on a Topcount scintillation counter. Controls with no lysate, inhibited lysate, and with no mAb were run routinely. Roughly 30% of input cortisone is reduced by 11βHSD1 in the uninhibited reaction under these conditions.

Test compounds having an IC$_{50}$ value less than about 20 μM according to this assay were considered active.

Example B

Cell-Based Assays for HSD Activity

Peripheral blood mononuclear cells (PBMCs) were isolated from normal human volunteers by Ficoll density centrifugation. Cells were plated at 4×10⁵ cells/well in 200 μL of AIM V (Gibco-BRL) media in 96 well plates. The cells were stimulated overnight with 50 ng/mL recombinant human IL-4 (R&D Systems). The following morning, 200 nM cortisone (Sigma) was added in the presence or absence of various concentrations of compound. The cells were incubated for 48 hours and then supernatants were harvested. Conversion of cortisone to cortisol was determined by a commercially available ELISA (Assay Design).

Test compounds having an $IC_{50}$ value less than about 20 μM according to this assay were considered active.

Example C

Cellular Assay to Evaluate MR Antagonism

Assays for MR antagonism were performed essentially as described (Jausons-Loffreda et al. J Biolumin and Chemilumin, 1994, 9: 217-221). Briefly, HEK293/MSR cells (Invitrogen Corp.) were co-transfected with three plasmids: 1) one designed to express a fusion protein of the GAL4 DNA binding domain and the mineralocorticoid receptor ligand binding domain, 2) one containing the GAL4 upstream activation sequence positioned upstream of a firefly luciferase reporter gene (pFR-LUC, Stratagene, Inc.), and 3) one containing the Renilla luciferase reporter gene cloned downstream of a thymidine kinase promoter (Promega). Transfections were performed using the FuGENE6 reagent (Roche). Transfected cells were ready for use in subsequent assays 24 hours post-transfection.

In order to evaluate a compound's ability to antagonize the MR, test compounds were diluted in cell culture medium (E-MEM, 10% charcoal-stripped FBS, 2 mM L-glutamine) supplemented with 1 nM aldosterone and applied to the transfected cells for 16-18 hours. After the incubation of the cells with the test compound and aldosterone, the activity of firefly luciferase (indicative of MR agonism by aldosterone) and Renilla luciferase (normalization control) were determined using the Dual-Glo Luciferae Assay System (Promega). Antagonism of the mineralocorticoid receptor was determined by monitoring the ability of a test compound to attenuate the aldosterone-induced firefly luciferase activity.

Compounds having an $IC_{50}$ of 100 μM or less were considered active.

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A compound of Formula I:

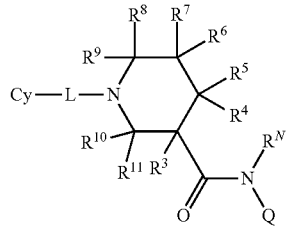

or a pharmaceutically acceptable salt thereof, wherein:

Cy is aryl, heteroaryl, cycloalkyl, or heterocycloalkyl, each optionally substituted with 1, 2, 3, 4 or 5 —W—X—Y—Z;

L is $SO_2$;

Q is cycloalkyl or heterocycloalkyl, each optionally substituted with 1, 2, 3, 4 or 5 —W'—X'—Y'—Z';

or Q is —$(CR^{1a}R^{1b})_m$-A;

A is aryl, heteroaryl, cycloalkyl, or heterocycloalkyl, each optionally substituted with 1, 2, 3, 4 or 5 —W'—X'—Y'—Z';

$R^{1a}$ and $R^{1b}$ are each, independently, H, halo, OH, $C_{1-4}$ alkyl, $C_{1-4}$ haloalkyl, $C_{1-4}$ hydroxylalkyl, $C_{1-4}$ alkoxy, $C_{1-4}$ haloalkoxy or $C_{1-4}$ hydroxylalkoxy;

wherein at least one of $R^{1a}$ and $R^{1b}$ is other than H;

m is 1, 2, 3 or 4;

$R^N$ is H, $C_{1-6}$ alkyl, aryl, heteroaryl, $C_{3-7}$ cycloalkyl, heterocycloalkyl, arylalkyl, heteroarylalkyl, ($C_{3-7}$ cycloalkyl)alkyl, or heterocycloalkylalkyl;

$R^3$, $R^4$, $R^5$, $R^6$, $R^7$, $R^8$, $R^9$, $R^{10}$ and $R^{11}$ are each, independently, H, $OC(O)R^{a'}$ $OC(O)OR^{b'}$, $C(O)OR^{b'}$, $OC(O)NR^{c'}R^{d'}$, $NR^{c'}R^{d'}$, $NR^{c'}C(O)R^{a'}$, $NR^{c'}C(O)OR^{b'}$, $S(O)R^{a'}$, $S(O)NR^{c'}R^{d'}$, $S(O)_2R^{a'}$, $S(O)_2NR^{c'}R^{d'}$, $OR^{b'}$, $SR^{b'}$, $C_{1-10}$ alkyl, $C_{1-10}$ haloalkyl, $C_{2-10}$ alkenyl, $C_{2-10}$ alkynyl, aryl, cycloalkyl, heteroaryl, heterocycloalkyl, arylalkyl, heteroarylalkyl, cycloalkylalkyl or heterocycloalkylalkyl, wherein said $C_{1-10}$ alkyl, $C_{1-10}$ haloalkyl, $C_{2-10}$ alkenyl, $C_{2-10}$ alkynyl, aryl, cycloalkyl, heteroaryl, heterocycloalkyl, arylalkyl, heteroarylalkyl, cycloalkylalkyl or heterocycloalkylalkyl is optionally substituted by $R^{14}$;

or $R^4$ and $R^5$ together with the carbon atom to which they are attached form a 3-14 membered cycloalkyl or heterocyloalkyl group which is optionally substituted by $R^{14}$;

or $R^6$ and $R^7$ together with the carbon atom to which they are attached form a 3-14 membered cycloalkyl or heterocyloalkyl group which is optionally substituted by $R^{14}$;

or $R^8$ and $R^9$ together with the carbon atom to which they are attached form a 3-14 membered cycloalkyl or heterocyloalkyl group which is optionally substituted by $R^{14}$;

or $R^{10}$ and $R^{11}$ together with the carbon atom to which they are attached form a 3-14 membered cycloalkyl or heterocyloalkyl group which is optionally substituted by $R^{14}$;

or $R^4$ and $R^6$ together with the carbon atom to which they are attached form a 3-7 membered fused cycloalkyl group or 3-7 membered fused heterocycloalkyl group which is optionally substituted by $R^{14}$;

or $R^6$ and $R^8$ together with the carbon atom to which they are attached form a 3-7 membered fused cycloalkyl group or 3-7 membered fused heterocycloalkyl group which is optionally substituted by $R^{14}$;

or $R^4$ and $R^9$ together form a $C_{1-3}$ alkylene bridge which is optionally substituted by $R^{14}$;

or $R^4$ and $R^{10}$ together form a $C_{1-3}$ alkylene bridge which is optionally substituted by $R^{14}$;

or $R^3$ and $R^7$ together form a $C_{1-3}$ alkylene bridge which is optionally substituted by $R^{14}$;

or $R^3$ and $R^9$ together form a $C_{1-3}$ alkylene bridge which is optionally substituted by $R^{14}$;

or $R^6$ and $R^{10}$ together form a $C_{1-3}$ alkylene bridge which is optionally substituted by $R^{14}$;

or $R^9$ and $R^{10}$ together form a $C_{1-3}$ alkylene bridge which is optionally substituted by $R^{14}$;

$R^{14}$ is halo, $C_{1-4}$ alkyl, $C_{1-4}$ haloalkyl, aryl, cycloalkyl, heteroaryl, heterocycloalkyl, CN, $NO_2$, $OR^{a'}$, $SR^{a'}$, $C(O)R^{b'}$, $C(O)NR^{c'}R^{d'}$, $C(O)OR^{a'}$, $OC(O)R^{b'}$, $OC(O)NR^{c'}R^{d'}$, $NR^{c'}R^{d'}$, $NR^{c'}C(O)R^{d'}$, $NR^{c'}C(O)OR^{a'}$, $S(O)R^{b'}$, $S(O)NR^{c'}R^{d'}$, $S(O)_2R^{b'}$, or $S(O)_2NR^{c'}R^{d'}$;

W, W' and W" are each, independently, absent, $C_{1-6}$ alkylenyl, $C_{2-6}$ alkenylenyl, $C_{2-6}$ alkynylenyl, O, S, $NR^e$, CO, COO, $CONR^e$, SO, $SO_2$, $SONR^e$, or $NR^eCONR^f$, wherein said $C_{1-6}$ alkylenyl, $C_{2-6}$ alkenylenyl, $C_{2-6}$ alkynylenyl are each optionally substituted by 1, 2 or 3 halo, OH, $C_{1-4}$ alkoxy, $C_{1-4}$ haloalkoxy, amino, $C_{1-4}$ alkylamino or $C_{2-8}$ dialkylamino;

X, X' and X" are each, independently, absent, $C_{1-6}$ alkylenyl, $C_{2-6}$ alkenylenyl, $C_{2-6}$ alkynylenyl, aryl, cycloalkyl, heteroaryl or heterocycloalkyl, wherein said $C_{1-6}$ alkylenyl, $C_{2-6}$ alkenylenyl, $C_{2-6}$ alkynylenyl, cycloalkyl, heteroaryl or heterocycloalkyl is optionally substituted by one or more halo, CN, $NO_2$, OH, $C_{1-4}$ alkoxy, $C_{1-4}$ haloalkoxy, amino, $C_{1-4}$ alkylamino or $C_{2-8}$ dialkylamino;

Y, Y' and Y" are each, independently, absent, $C_{1-6}$ alkylenyl, $C_{2-6}$ alkenylenyl, $C_{2-6}$ alkynylenyl, O, S, $NR^e$, CO, COO, $CONR^e$, SO, $SO_2$, $SONR^e$, or $NR^eCONR^f$, wherein said $C_{1-6}$ alkylenyl, $C_{2-6}$ alkenylenyl, $C_{2-6}$ alkynylenyl are each optionally substituted by 1, 2 or 3 halo, OH, $C_{1-4}$ alkoxy, $C_{1-4}$ haloalkoxy, amino, $C_{1-4}$ alkylamino or $C_{2-8}$ dialkylamino;

Z, Z' and Z" are each, independently, H, halo, CN, $NO_2$, OH, $C_{1-4}$ alkoxy, $C_{1-4}$ haloalkoxy, amino, $C_{1-4}$ alkylamino, $C_{2-8}$ dialkylamino, $C_{1-6}$ alkyl, $C_{2-6}$ alkenyl, $C_{2-6}$ alkynyl, aryl, cycloalkyl, heteroaryl or heterocycloalkyl, wherein said $C_{1-6}$ alkyl, $C_{2-6}$ alkenyl, $C_{2-6}$ alkynyl, aryl, cycloalkyl, heteroaryl or heterocycloalkyl is optionally substituted by 1, 2 or 3 halo, $C_{1-6}$ alkyl, $C_{2-6}$ alkenyl, $C_{2-6}$ alkynyl, $C_{1-4}$ haloalkyl, aryl, cycloalkyl, heteroaryl, heterocycloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^d$, $NR^cC(O)OR^a$, $S(O)R^b$, $S(O)NR^cR^d$, $S(O)_2R^b$, or $S(O)_2NR^cR^d$;

wherein two —W—X—Y—Z attached to the same atom optionally form a 3-14 membered cycloalkyl or heterocyloalkyl group, each optionally substituted by 1, 2 or 3 —W"—X"—Y"—Z";

wherein two —W'—X'—Y'—Z' attached to the same atom optionally form a 3-14 membered cycloalkyl or heterocyloalkyl group, each optionally substituted by 1, 2 or 3 —W"—X"—Y"—Z";

wherein —W—X—Y—Z is other than H;

wherein —W'—X'—Y'—Z' is other than H;

wherein —W"—X"—Y"—Z" is other than H;

$R^a$ and $R^{a'}$ are each, independently, H, $C_{1-6}$ alkyl, $C_{1-6}$ haloalkyl, $C_{2-6}$ alkenyl, $C_{2-6}$ alkynyl, aryl, cycloalkyl, heteroaryl or heterocycloalkyl, wherein said $C_{1-6}$ alkyl, $C_{1-6}$ haloalkyl, $C_{2-6}$ alkenyl, $C_{2-6}$ alkynyl, aryl, cycloalkyl, heteroaryl or heterocycloalkyl; heterocloalkyl, heterocycloalkylalkyl is optionally substituted with H, OH, amino, halo, $C_{1-6}$ alkyl, $C_{1-6}$ haloalkyl, aryl, arylalkyl, heteroaryl, heteroarylalkyl, cycloalkyl or heterocycloalkyl;

$R^b$ and $R^{b'}$ are each, independently, H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl, wherein said $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl is optionally substituted with H, OH, amino, halo, $C_{1-6}$ alkyl, $C_{1-6}$ haloalkyl, $C_{1-6}$ haloalkyl, aryl, arylalkyl, heteroaryl, heteroarylalkyl, cycloalkyl or heterocycloalkyl;

$R^c$ and $R^d$ are each, independently, H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with H, OH, amino, halo, $C_{1-6}$ alkyl, $C_{1-6}$ haloalkyl, $C_{1-6}$ haloalkyl, aryl, arylalkyl, heteroaryl, heteroarylalkyl, cycloalkyl or heterocycloalkyl;

or $R^c$ and $R^d$ together with the N atom to which they are attached form a 4-, 5-, 6- or 7-membered heterocycloalkyl group;

$R^{c'}$ and $R^{d'}$ are each, independently, H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with H, OH, amino, halo, $C_{1-6}$ alkyl, $C_{1-6}$ haloalkyl, $C_{1-6}$ haloalkyl, aryl, arylalkyl, heteroaryl, heteroarylalkyl, cycloalkyl or heterocycloalkyl;

or $R^{c'}$ and $R^{d'}$ together with the N atom to which they are attached form a 4-, 5-, 6- or 7-membered heterocycloalkyl group;

$R^e$ and $R^f$ are each, independently, H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with H, OH, amino, halo, $C_{1-6}$ alkyl, $C_{1-6}$ haloalkyl, $C_{1-6}$ haloalkyl, aryl, arylalkyl, heteroaryl, heteroarylalkyl, cycloalkyl or heterocycloalkyl; and or $R^e$ and $R^f$ together with the N atom to which they are attached form a 4-, 5-, 6- or 7-membered heterocycloalkyl group;

with the provisos:

a) when Q is unsubstituted $C_{3-8}$ cycloalkyl; adamantyl; 1,2,3,4-tetrahydro-1-naphthanenyl; bicyclo[2.2.1]hept-2-yl; 2-methylcyclohexyl; or 1-ethylnylcyclohexyl; at and least one of $R^3$, $R^4$, $R^5$, $R^6$, $R^7$, $R^8$, $R^9$, $R^{10}$ and $R^{11}$ is other than H; and b) when each of $R^3$, $R^4$, $R^5$, $R^6$, $R^7$, $R^8$, $R^9$, $R^{10}$ and $R^{11}$ is H, then Q is other than tetrahydrothienyl, S-oxo-tetrahydrothienyl, S,S-dioxo-tetrahydrothienyl, 2,2,6,6-tetramethyl-4-piperidinyl, N-substituted pyrrolidin-3-yl, N-substituted piperidin-4-yl, or 3,4,5,6-tetra-substituted tetrahydropyran-2-yl.

2. The compound of claim 1, or a pharmaceutically acceptable salt thereof, wherein Cy is aryl or heteroaryl, each optionally substituted with 1, 2, 3, 4 or 5 —W—X—Y—Z.

3. The compound of claim 1, or a pharmaceutically acceptable salt thereof, wherein Cy is aryl or heteroaryl, each optionally substituted with 1, 2, 3, 4 or 5 —W—X—Y—Z wherein W is O or absent, X is absent, and Y is absent.

4. The compound of claim 1, or a pharmaceutically acceptable salt thereof, wherein Cy is phenyl, naphthyl, pyridyl, pyrimidinyl, quinolinyl, benzoxazolyl, pyridazinyl, pyrazinyl, triazinyl, furanyl or thienyl, each optionally substituted with 1, 2, or 3 halo, CN, $C_{1-4}$ alkoxy, $C_{1-4}$ haloalkoxy, $C_{1-6}$ alkyl or aryl, wherein said $C_{1-6}$ alkyl or aryl is optionally substituted by 1, 2 or 3 halo, $C_{1-6}$ alkyl, $C_{1-4}$ haloalkyl, CN, $NO_2$, $OR^a$, or $SR^a$.

5. The compound of claim 1, or a pharmaceutically acceptable salt thereof, wherein Q is cycloalkyl or heterocycloalkyl, each substituted with 1, 2, 3, 4 or 5 —W'—X'—Y'—Z'.

6. The compound of claim 1, or a pharmaceutically acceptable salt thereof, wherein Q is cycloalkyl or heterocycloalkyl, each optionally substituted with 1, 2, 3, 4 or 5 OH, $C_{1-4}$ alkoxy, $NR^eCOO(C_{1-4}$ alkyl), $NR^eCO(C_{1-4}$ alkyl), $NR^eSO_2$ ($C_{1-4}$ alkyl), aryl, heteroaryl, —O-aryl, —O-heteroaryl, or —($C_{1-4}$ alkyl)-OH.

7. The compound of claim 1, or a pharmaceutically acceptable salt thereof, wherein Q is cycloalkyl or heterocycloalkyl, each substituted with at least two —W'—X'—Y'—Z', wherein two of said at least two —W'—X'—Y'—Z' are attached to the same atom and together with the atom to which they are attached form a 3-14 membered cycloalkyl or heterocyloalkyl group, each optionally substituted by 1, 2 or 3 —W"—X"—Y"—Z".

8. The compound of claim 1, or a pharmaceutically acceptable salt thereof, wherein Q is cycloalkyl or heterocycloalkyl, each substituted with at least two —W'—X'—Y'—Z', wherein two of said at least two —W'—X'—Y'—Z' are attached to the same atom and together with the atom to which they are attached form a 3-14 membered heterocyloalkyl group optionally substituted by 1, 2 or 3 —W"—X"—Y"—Z".

9. The compound of claim 1, or a pharmaceutically acceptable salt thereof, wherein Q is cyclopropyl, cyclobutyl, cyclopentyl, cyclohexyl, cycloheptyl, indanyl, or 1,2,3,4-tetrahydronaphthalen-2-yl, each optionally substituted with 1, 2, 3, 4 or 5 —W'—X'—Y'—Z'.

10. The compound of claim 1, or a pharmaceutically acceptable salt thereof, wherein Q is a 3-14 membered heterocycloalkyl group comprising at least one ring-forming O atom, wherein said 3-14 membered heterocycloalkyl group is optionally substituted with 1, 2, 3, 4 or 5 —W'—X'—Y'—Z'.

11. The compound of claim 1, or a pharmaceutically acceptable salt thereof, wherein Q is cyclohexyl substituted at the 4-position with at least one —W'—X'—Y'—Z'.

12. The compound of claim 1, or a pharmaceutically acceptable salt thereof, wherein Q is cyclohexyl substituted at the 4-position with at least one —OH.

13. The compound of claim 1, or a pharmaceutically acceptable salt thereof, wherein $R^N$ is H, $C_{1-6}$ alkyl, $C_{3-7}$ cycloalkyl, or ($C_{3-7}$ cycloalkyl)alkyl.

14. The compound of claim 1, or a pharmaceutically acceptable salt thereof, wherein $R^N$ is H.

15. The compound of claim 1, or a pharmaceutically acceptable salt thereof, wherein $R^3$, $R^4$, $R^5$, $R^6$, $R^7$, $R^8$, $R^9$, $R^{10}$ and $R^{11}$ n are each independently, H, $C_{1-10}$ alkyl or $C_{1-10}$ haloalkyl.

16. The compound of claim 1, or a pharmaceutically acceptable salt thereof, wherein $R^3$, $R^4$, $R^5$, $R^6$, $R^7$, $R^8$, $R^9$, $R^{10}$ and $R^{11}$ are each H.

17. The compound of claim 1, or a pharmaceutically acceptable salt thereof, wherein $R^3$ is $C_{1-10}$ alkyl.

18. A compound selected from:
N-Cyclohexyl-1-[(2-nitrophenyl)sulfonyl]piperidine-3-carboxamide;
N-Cyclohexyl-N-cyclopropyl-1-(phenylsulfonyl)piperidine-3-carboxamide;
N-[(1R)-1-Phenylethyl]-1-(phenylsulfonyl)piperidine-3-carboxamide;
N-(1-Methyl-3-phenylpropyl)-1-(phenylsulfonyl)piperidine-3-carboxamide;
N-(4-Hydroxycyclohexyl)-1-(phenylsulfonyl)piperidine-3-carboxamide;
(3R)—N-(4-Hydroxycyclohexyl)-1-(phenylsulfonyl)piperidine-3-carboxamide;
1-[(4-Chlorophenyl)sulfonyl]-N-cyclohexylpiperidine-3-carboxamide;
1-[(5-Chloro-2-fluorophenyl)sulfonyl]-N-cyclohexylpiperidine-3-carboxamide;
1-[(3-Chlorophenyl)sulfonyl]-N-cyclohexylpiperidine-3-carboxamide;
N-Cyclohexyl-1-[(2-fluorophenyl)sulfonyl]piperidine-3-carboxamide;
1-[(3-Chloro-2-methylphenyl)sulfonyl]-N-cyclohexylpiperidine-3-carboxamide;
N-Cyclohexyl-1-{[2-(trifluoromethyl)phenyl]sulfonyl}piperidine-3-carboxamide;
(3S)—N-Cyclohexyl-1-[(2-fluorophenyl)sulfonyl]piperidine-3-carboxamide;
(3S)—N-Cyclohexyl-1-[(2-methylphenyl)sulfonyl]piperidine-3-carboxamide;
(3S)—N-Cyclohexyl-1-[(4-fluoro-2-methylphenyl)sulfonyl]piperidine-3-carboxamide;
(3S)-1-[(2-Chlorophenyl)sulfonyl]-N-cyclohexylpiperidine-3-carboxamide'
(3S)—N-cyclohexyl-1-[(2,6-difluorophenyl)sulfonyl]piperidine-3-carboxamide;
(3S)-1-[(3-Chloro-4-fluorophenyl)sulfonyl]-N-cyclohexylpiperidine-3-carboxamide;
(3S)-1-[(3-Chloro-2-methylphenyl)sulfonyl]-N-cyclohexylpiperidine-3-carboxamide;
(3S)-1-[(5-Chloro-2-fluorophenyl)sulfonyl]-N-cyclohexylpiperidine-3-carboxamide;
(3S)-1-[(3-Chlorophenyl)sulfonyl]-N-cyclohexylpiperidine-3-carboxamide;
(3S)-1-[(3-Chloro-2-fluorophenyl)sulfonyl]-N-cyclohexylpiperidine-3-carboxamide;
N-[(1S)-1-phenylethyl]-1-(phenylsulfonyl)piperidine-3-carboxamide;
(3S)—N-cyclohexyl-1-(pyridin-3-ylsulfonyl)piperidine-3-carboxamide;
(3S)—N-cyclohexyl-1-[(3-phenoxyphenyl)sulfonyl]piperidine-3-carboxamide;
(3S)-1-[(2-cyanophenyl)sulfonyl]-N-cyclohexylpiperidine-3-carboxamide;
(3S)—N-cyclohexyl-1-[(2-phenoxyphenyl)sulfonyl]piperidine-3-carboxamide;
(3S)—N-cyclohexyl-1-{[3-(pyridin-4-yloxy)phenyl]sulfonyl}piperidine-3-carboxamide;

(3S)—N-cyclohexyl-1-[(4-phenoxypyridin-3-yl)sulfonyl]piperidine-3-carboxamide;
(3S)—N-cyclohexyl-1-{[3-(2-methylphenoxy)phenyl]sulfonyl}piperidine-3-carboxamide;
(3S)-1-{[3-(2-chlorophenoxy)phenyl]sulfonyl}-N-cyclohexylpiperidine-3-carboxamide;
(3S)-1-{[3-(4-chlorophenoxy)phenyl]sulfonyl}-N-cyclohexylpiperidine-3-carboxamide;
(3S)—N-cyclohexyl-1-[(3-methoxyphenyl)sulfonyl]piperidine-3-carboxamide;
(3S)-1-[(3-chloro-4-fluorophenyl)sulfonyl]-N-(trans-4-hydroxycyclohexyl)piperidine-3-carboxamide;
(3S)-1-[(2,6-difluorophenyl)sulfonyl]-N-(trans-4-hydroxycyclohexyl)piperidine-3-carboxamide;
(3S)-1-[(3-chloro-2-methylphenyl)sulfonyl]-N-(trans-4-hydroxycyclohexyl)piperidine-3-carboxamide;
(3S)-1-[(2-fluorophenyl)sulfonyl]-N-(trans-4-hydroxycyclohexyl)piperidine-3-carboxamide;
(3S)-1-[(5-chloro-2-fluorophenyl)sulfonyl]-N-(trans-4-hydroxycyclohexyl)piperidine-3-carboxamide;
(3S)-1-[(3-chlorophenyl)sulfonyl]-N-(trans-4-hydroxycyclohexyl)piperidine-3-carboxamide;
(3S)-1-[(3-chloro-2-fluorophenyl)sulfonyl]-N-(trans-4-hydroxycyclohexyl)piperidine-3-carboxamide;
(3S)—N-(trans-4-hydroxycyclohexyl)-1-[(2-methylphenyl)sulfonyl]piperidine-3-carboxamide;
(3S)-1-[(4-fluoro-2-methylphenyl)sulfonyl]-N-(trans-4-hydroxycyclohexyl)piperidine-3-carboxamide;
(3S)-1-[(2-chlorophenyl)sulfonyl]-N-(trans-4-hydroxycyclohexyl)piperidine-3-carboxamide;
(3S)-1-[(2-cyanophenyl)sulfonyl]-N-(trans-4-hydroxycyclohexyl)piperidine-3-carboxamide;
(3S)—N-(trans-4-hydroxycyclohexyl)-1-[(3-phenoxyphenyl)sulfonyl]piperidine-3-carboxamide;
(3S)—N-(trans-4-hydroxycyclohexyl)-1-{[4-(pyridin-3-yloxy)-phenyl]-sulfonyl}-piperidine-3-carboxamide;
(3S)—N-(trans-4-hydroxycyclohexyl)-1-{[3-(2-methylphenoxy)-phenyl]sulfonyl}-piperidine-3-carboxamide;
(3S)-1-{[3-(2-chlorophenoxy)-phenyl]sulfonyl}-N-(trans-4-hydroxycyclohexyl)-piperidine-3-carboxamide;
(3S)—N-(trans-4-hydroxycyclohexyl)-1-[(2-methoxyphenyl)sulfonyl]piperidine-3-carboxamide;
(3S)—N-(trans-4-hydroxycyclohexyl)-1-[(2-phenoxyphenyl)sulfonyl]piperidine-3-carboxamide;
(3S)—N-(trans-4-hydroxycyclohexyl)-1-[(6-phenoxypyridin-3-yl)sulfonyl]piperidine-3-carboxamide;
(3S)—N-(trans-4-hydroxycyclohexyl)-1-[(3-isopropylphenyl)sulfonyl]piperidine-3-carboxamide;
(3S)-1-[(3,4-dimethoxyphenyl)sulfonyl]-N-(trans-4-hydroxycyclohexyl)piperidine-3-carboxamide;
(3S)—N-(trans-4-hydroxycyclohexyl)-1-[(2-nitrophenyl)sulfonyl]piperidine-3-carboxamide;
(3S)—N-cyclopentyl-1-[(2,6-difluorophenyl)sulfonyl]piperidine-3-carboxamide;
(3S)-1-[(3-chloro-2-methylphenyl)sulfonyl]-N-cyclopentylpiperidine-3-carboxamide;
(3S)-1-[(3-chlorophenyl)sulfonyl]-N-cyclopentylpiperidine-3-carboxamide;
(3S)—N—[trans-4-(acetylamino)cyclohexyl]-1-(phenylsulfonyl)piperidine-3-carboxamide;
(3S)—N-{trans-4-[(methylsulfonyl)amino]cyclohexyl}-1-(phenylsulfonyl)piperidine-3-carboxamide;
Methyl[trans-4-({[(3S)-1-(phenylsulfonyl)piperidin-3-yl]carbonyl}amino)cyclohexyl]carbamate;
(3S)—N-(3-hydroxycyclohexyl)-1-(phenylsulfonyl)piperidine-3-carboxamide;
(3S)-1-[(2-fluorophenyl)sulfonyl]-N-(3-hydroxycyclohexyl)piperidine-3-carboxamide;
(3S)-1-[(5-chloro-2-fluorophenyl)sulfonyl]-N-(3-hydroxycyclohexyl)piperidine-3-carboxamide;
(3S)-1-[(3-chloro-2-methylphenyl)sulfonyl]-N-(3-hydroxycyclohexyl)piperidine-3-carboxamide;
(3S)—N-(3-hydroxycyclohexyl)-1-[(3-methoxyphenyl)sulfonyl]piperidine-3-carboxamide;
(3S)-1-[(3-chlorophenyl)sulfonyl]-N-(3-hydroxycyclohexyl)piperidine-3-carboxamide;
(3S)-1-[(2-bromophenyl) sulfonyl]-N-(3-hydroxycyclohexyl)piperidine-3-carboxamide;
(3S)—N-(3-hydroxycyclohexyl)-1-[(3-methylphenyl)sulfonyl]piperidine-3-carboxamide;
(3S)-1-[(3-fluorophenyl)sulfonyl]-N-(3-hydroxycyclohexyl)piperidine-3-carboxamide;
(3S)-1-[(2,6-dichlorophenyl)sulfonyl]-N-(3-hydroxycyclohexyl)piperidine-3-carboxamide;
(3S)-1-[(2,5-dimethylphenyl)sulfonyl]-N-(3-hydroxycyclohexyl)piperidine-3-carboxamide;
(3S)-1-[(3-bromophenyl)sulfonyl]-N-(3-hydroxycyclohexyl)piperidine-3-carboxamide;
(3S)-1-[(2,5-dichlorophenyl)sulfonyl]-N-(3-hydroxycyclohexyl)piperidine-3-carboxamide;
(3S)-1-[(2,4-difluorophenyl)sulfonyl]-N-(3-hydroxycyclohexyl)piperidine-3-carboxamide;
(3S)-1-[(3,5-dichlorophenyl)sulfonyl]-N-(3-hydroxycyclohexyl)piperidine-3-carboxamide;
(3S)-1-[(2,5-difluorophenyl)sulfonyl]-N-(3-hydroxycyclohexyl)piperidine-3-carboxamide;
(3S)-1-[(2-bromophenyl)sulfonyl]-N-(trans-4-hydroxycyclohexyl)piperidine-3-carboxamide;
(3S)—N-(trans-4-hydroxycyclohexyl)-1-[(3-methylphenyl)sulfonyl]piperidine-3-carboxamide;
(3S)-1-[(3-fluorophenyl)sulfonyl]-N-(trans-4-hydroxycyclohexyl)piperidine-3-carboxamide;
(3S)-1-[(2,6-dichlorophenyl)sulfonyl]-N-(trans-4-hydroxycyclohexyl)piperidine-3-carboxamide;
(3S)-1-[(2,5-dimethylphenyl)sulfonyl]-N-(trans-4-hydroxycyclohexyl)piperidine-3-carboxamide;
(3S)-1-[(3-bromophenyl)sulfonyl]-N-(trans-4-hydroxycyclohexyl)piperidine-3-carboxamide;
(3S)-1-[(2,5-dichlorophenyl)sulfonyl]-N-(trans-4-hydroxycyclohexyl)piperidine-3-carboxamide;
(3S)-1-[(2,4-difluorophenyl)sulfonyl]-N-(trans-4-hydroxycyclohexyl)piperidine-3-carboxamide;
(3S)-1-[(3,5-dichlorophenyesulfonyl]-N-(trans-4-hydroxycyclohexyl)piperidine-3-carboxamide;
(3S)-1-[(2,3-dichlorophenyl)sulfonyl]-N-(trans-4-hydroxycyclohexyl)piperidine-3-carboxamide;
(3S)-1-[(2,5-difluorophenyl)sulfonyl]-N-(trans-4-hydroxycyclohexyl)piperidine-3-carboxamide;
(3S)—N-(trans-4-hydroxycyclohexyl)-1-(2-thienylsulfonyl)piperidine-3-carboxamide;
(3S)-1-[(3-chloro-2-methylphenyl)sulfonyl]-N-cycloheptylpiperidine-3-carboxamide;
(3S)—N-cycloheptyl-1-[(2-fluorophenyl)sulfonyl]piperidine-3-carboxamide;
(3S)-1-[(2-bromophenyl)sulfonyl]-N-cycloheptylpiperidine-3-carboxamide;
(3S)-1-[(3-chlorophenyl)sulfonyl]-N-cycloheptylpiperidine-3-carboxamide;
(3S)—N-cycloheptyl-1-[(3-methylphenyl)sulfonyl]piperidine-3-carboxamide;

(3S)-1-(phenylsulfonyl)-N-(tetrahydro-2H-pyran-4-yl)piperidine-3-carboxamide;
(3S)-1-[(3-chloro-2-methylphenyl)sulfonyl]-N-(tetrahydro-2H-pyran-4-yl)piperidine-3-carboxamide;
(3S)-1-[(3-methoxyphenyl)sulfonyl]-N-(tetrahydro-2H-pyran-4-yl)piperidine-3-carboxamide;
(3S)-1-(phenylsulfonyl)-N-[4-(pyridin-4-yloxy)cyclohexyl]piperidine-3-carboxamide;
N-cyclohexyl-3-methyl-1-(phenylsulfonyl)piperidine-3-carboxamide;
(3S)-1-[(3-chloro-2-methylphenyl)sulfonyl]-N-(3-oxo-3H-spiro[2-benzofuran-1,1'-cyclohexan]-4'-yl)piperidine-3-carboxamide;
(3S)-1-[(2,6-dichlorophenyl)sulfonyl]-N-(3-oxo-3H-spiro[2-benzofuran-1,1'-cyclohexan]-4'-yl)piperidine-3-carboxamide;
(3S)-1-[(3-chloro-2-methylphenypsulfonyl]-N-(cyclopropylmethyl)-N-(trans-4-hydroxycyclohexyl)piperidine-3-carboxamide;
(3S)—N-cycloheptyl-1-[(2,6-dichlorophenyl)sulfonyl]piperidine-3-carboxamide;
(3S)-1-[(3-chloro-2-methylphenyl)sulfonyl]-N-[trans-4-(hydroxymethyl)cyclohexyl]piperidine-3-carboxamide;
(3S)—N-(trans-4-hydroxycyclohexyl)-1-(quinolin-8-ylsulfonyl)piperidine-3-carboxamide;
(3S)—N-(trans-4-hydroxycyclohexyl)-1-(1-naphthylsulfonyl)piperidine-3-carboxamide;
(3S)—N-(trans-4-hydroxycyclohexyl)-1-(2-naphthylsulfonyl)piperidine-3-carboxamide;
(3S)-1-[(3-chloro-2-methylphenyl)sulfonyl]-N-[(1R)-1,2,3,4-tetrahydronaphthalen-1-yl]piperidine-3-carboxamide;
(3S)-1-benzoyl-N-(4-hydroxycyclohexyl)piperidine-3-carboxamide;
(3S)-1-[(3-chloro-2-methylphenyl)sulfonyl]-N-(cis-4-hydroxycyclohexyl)piperidine-3-carboxamide;
(3S)-1-[(2-chlorophenyl)sulfonyl]-N-(cis-4-hydroxycyclohexyl)piperidine-3-carboxamide;
(3S)-1-(biphenyl-4-ylsulfonyl)-N-(trans-4-hydroxycyclohexyl)piperidine-3-carboxamide;
(3S)—N-(trans-4-hydroxycyclohexyl)-1-{[4-(trifluoromethyl)phenyl]sulfonyl}piperidine-3-carboxamide;
(3S)-1-{[3-(difluoromethoxy)phenyl]sulfonyl}-N-(trans-4-hydroxycyclohexyl)piperidine-3-carboxamide;
(3S)-1-{[3-(4-fluorophenoxy)phenyl]sulfonyl}-N-(trans-4-hydroxycyclohexyl)piperidine-3-carboxamide;
(3S)—N-(trans-4-hydroxycyclohexyl)-1-{[3-(trifluoromethoxy)phenyl]sulfonyl}piperidine-3-carboxamide;
(3S)-1-(biphenyl-3-ylsulfonyl)-N-(trans-4-hydroxycyclohexyl)piperidine-3-carboxamide;
(3S)-1-[(3-chloro-2-methylphenyl)sulfonyl]-N-(1,2,3,4-tetrahydronaphthalen-2-yl)piperidine-3-carboxamide;
(3S)-1-[(2,6-dichlorophenyl)sulfonyl]-N-(1,2,3,4-tetrahydronaphthalen-2-yl)piperidine-3-carboxamide;
(3S)-1-(phenylsulfonyl)-N-[trans-4-(pyridin-4-yloxy)cyclohexyl]piperidine-3-carboxamide;
(3S)-1-[(3-chloro-2-methylphenyl)sulfonyl]-N-[trans-4-(pyridin-4-yloxy)cyclohexyl]piperidine-3-carboxamide;
(3S)-1-acetyl-N-(3S)-1-[(3-chloro-2-methylphenyl)sulfonyl]piperidin-3-ylpiperidine-3-carboxamide;
methyl (3S)-3-[((3S)-1-[(3-chloro-2-methylphenyl)sulfonyl]piperidin-3-ylamino)carbonyl]piperidine-1-carboxylate;
and pharmaceutically acceptable salts thereof.

19. A composition comprising a compound of claim 1, or a pharmaceutically and a pharmaceutically acceptable carrier.

20. A method of treating a disease in a patient, wherein said disease is obesity, type 2 diabetes, glucose intolerance, insulin resistance, hyperglycemia, hypertension, hyperlipidemia, cognitive impairment, depression, dementia, glaucoma, cardiovascular disorders, osteoporosis, inflammation, a cardiovascular, renal or inflammatory disease, heart failure, atherosclerosis, arteriosclerosis, coronary artery disease, thrombosis, angina, peripheral vascular disease, vascular wall damage, stroke, dyslipidemia, hyperlipoproteinaemia, diabetic dyslipidemia, mixed dyslipidemia, hypercholesterolemia, hypertriglyceridemia, metabolic syndrome or general aldosterone-related target organ damage, comprising administering to said patient a therapeutically effective amount of a compound according to claim 1, or a pharmaceutically acceptable salt thereof.

21. A method of treating type 2 diabetes in a patient, comprising administering to said patient a therapeutically effective amount of a compound according to claim 1, or a pharmaceutically acceptable salt thereof.

* * * * *

UNITED STATES PATENT AND TRADEMARK OFFICE
CERTIFICATE OF CORRECTION

PATENT NO. : 8,288,417 B2
APPLICATION NO. : 13/279700
DATED : October 16, 2012
INVENTOR(S) : Wenqing Yao et al.

It is certified that error appears in the above-identified patent and that said Letters Patent is hereby corrected as shown below:

In the specification:

Col. 1, Line 8, delete "which is pending," and insert -- now U.S. Pat. No. 8,071,624, --.

In the claims:

Col. 126, Line 33, Claim 1, after "OC(O)R$^a$"" insert -- , --.

Col. 126, Line 45-46, Claim 1, delete "heterocyloalkyl" and insert -- heterocycloalkyl --.

Col. 126, Line 49-50, Claim 1, delete "heterocyloalkyl" and insert -- heterocycloalkyl --.

Col. 126, Line 53-54, Claim 1, delete "heterocyloalkyl" and insert -- heterocycloalkyl --.

Col. 126, Line 57-58, Claim 1, delete "heterocyloalkyl" and insert -- heterocycloalkyl --.

Col. 127, Line 53-54, Claim 1, delete "heterocyloalkyl" and insert -- heterocycloalkyl --.

Col. 127, Line 57-58, Claim 1, delete "heterocyloalkyl" and insert -- heterocycloalkyl --.

Col. 128, Line 14 (Approx.), Claim 1, before "aryl," delete "$C_{1-6}$ haloalkyl,".

Col. 128, Line 25, Claim 1, before "aryl," delete "$C_{1-6}$ haloalkyl,".

Col. 128, Line 39, Claim 1, before "aryl," delete "$C_{1-6}$ haloalkyl,".

Col. 128, Line 53, Claim 1, before "aryl," delete "$C_{1-6}$ haloalkyl,".

Col. 128, Line 55, Claim 1, after "heterocycloalkyl;" delete "and".

Col. 128, Line 61, Claim 1, delete "naphthanenyl;" and insert -- naphthalenyl; --.

Col. 128, Line 62, Claim 1, delete "ethylnylcyclohexyl;" and insert -- ethynylcyclohexyl; --.

Col. 128, Line 63, Claim 1, before "least" delete "and".

Col. 129, Line 34-35 (Approx.), Claim 7, delete "heterocyloalkyl" and insert -- heterocycloalkyl --.

Col. 129, Line 43, Claim 8, delete "heterocyloalkyl" and insert -- heterocycloalkyl --.

Col. 130, Line 3, Claim 15, before "are" delete "n".

Col. 130, Line 3, Claim 15, delete "each" and insert -- each, --.

Signed and Sealed this
Eleventh Day of August, 2015

Michelle K. Lee
*Director of the United States Patent and Trademark Office*

CERTIFICATE OF CORRECTION (continued)
U.S. Pat. No. 8,288,417 B2

Col. 130, Line 43, Claim 18, delete "carboxamide'" and insert -- carboxamide; --.

Col. 132, Line 14 (Approx.), Claim 18, delete "bromophenyl) sulfonyl]" and insert -- bromophenyl)sulfonyl] --.

Col. 132, Line 50, Claim 18, delete "dichlorophenyesulfonyl]" and insert -- dichlorophenyl)sulfonyl] --.

Col. 133, Line 17, Claim 18, delete "methylphenypsulfonyl]" and insert -- methylphenyl)sulfonyl] --.

Col. 134, Line 24, Claim 19, after "pharmaceutically" insert -- acceptable salt thereof, --.

Col. 134, Line 33, Claim 20, delete "hyperlipoproteinaemia," and insert -- hyperlipoproteinemia, --.